United States Patent [19]
Green et al.

[11] Patent Number: 5,645,209
[45] Date of Patent: Jul. 8, 1997

[54] SELF CONTAINED GAS POWERED SURGICAL APPARATUS

[75] Inventors: David T. Green, Westport; Mitchell J. Palmer, New Milford; Keith L. Milliman, Norwalk; Robert C. Savage, Stratford; Richard C. McClure, Monroe; Lisa W. Heaton, Norwalk, all of Conn.

[73] Assignee: United States Surgical Corporation, Norwalk, Conn.

[21] Appl. No.: 559,227

[22] Filed: Nov. 17, 1995

Related U.S. Application Data

[60] Division of Ser. No. 133,549, Oct. 8, 1993, Pat. No. 5,478,003, which is a continuation-in-part of Ser. No. 24,533, Mar. 1, 1993, Pat. No. 5,312,023, which is a continuation-in-part of Ser. No. 949,685, Sep. 23, 1992, Pat. No. 5,326,013, which is a continuation-in-part of Ser. No. 915,425, Jul. 17, 1992, abandoned, which is a continuation-in-part of Ser. No. 781,012, Oct. 18, 1991, abandoned.

[51] Int. Cl.$^6$ .................................................. A61B 17/068
[52] U.S. Cl. .................... 227/175.2; 227/19; 227/176.1; 227/179.1
[58] Field of Search ........................... 227/19, 175.2, 227/176.1, 178.1, 8, 179.1

[56] References Cited

U.S. PATENT DOCUMENTS

| Re. 28,932 | 8/1976 | Noiles et al. . |
|---|---|---|
| 2,448,741 | 9/1948 | Scott et al. . |
| 3,079,606 | 3/1963 | Bobrov et al. . |
| 3,490,675 | 1/1970 | Green et al. . |
| 3,499,591 | 3/1970 | Green . |
| 3,593,903 | 7/1971 | Astafiev et al. . |
| 3,618,842 | 11/1971 | Bryan . |
| 3,633,874 | 1/1972 | Chow et al. . |
| 3,643,851 | 2/1972 | Green et al. . |
| 3,662,939 | 5/1972 | Bryan . |

(List continued on next page.)

FOREIGN PATENT DOCUMENTS

| 0041022 | 12/1981 | European Pat. Off. . |
|---|---|---|
| 0216532 | 4/1987 | European Pat. Off. . |
| 0324166 | 7/1989 | European Pat. Off. . |
| 0324637 | 7/1989 | European Pat. Off. . |
| 0365153 | 4/1990 | European Pat. Off. . |
| 0373762 | 6/1990 | European Pat. Off. . |
| 0399701 | 11/1990 | European Pat. Off. . |
| 0552050 | 7/1993 | European Pat. Off. . |
| 0552423 | 7/1993 | European Pat. Off. . |
| 0593920 | 4/1994 | European Pat. Off. . |
| 0603472 | 6/1994 | European Pat. Off. . |
| 728848 | 5/1977 | U.S.S.R. . |
| 1352554 | 4/1971 | United Kingdom . |

OTHER PUBLICATIONS

Swain, C.P., Brown, G.J. and Mills, T.N., "Endoscopic Stapling Device; The Development of a New Flexible Endoscopically Controlled Device for Placing Multiple Transmural Staples in Gastrointestinal Tissue, " Gastrointestinal Endoscopy, 1989, vol. 35, No. 4, pp. 338–339.

*Primary Examiner*—Scott A. Smith

[57] ABSTRACT

A self contained gas powered endoscopic surgical apparatus is provided for placing lateral lines of surgical fasteners into body tissue. The apparatus includes a frame portion, an elongated portion extending from the frame portion, and an articulating fastener applying assembly associated with a distal end of the elongated portion. The fastener applying assembly includes a base portion, a staple cartridge housing, and an anvil member which has a forming surface thereon against which surgical fasteners are driven as they are ejected from the cartridge housing. A self contained pneumatic system is associated with the frame portion and is actuable to eject the surgical fasteners from the cartridge assembly. A first mechanism is provided for effectuating the rotation of the fastener applying assembly about an axis defined by the body portion, a second mechanism is provided for effectuating the articulation of the fastener applying assembly, and a third mechanism is provided for independently rotating the cartridge housing and anvil member relative to a longitudinal axis defined by the base position to increase the range of operability of the apparatus.

11 Claims, 61 Drawing Sheets

U.S. PATENT DOCUMENTS

| | | |
|---|---|---|
| 3,675,688 | 7/1972 | Bryan et al. . |
| 3,717,294 | 2/1973 | Green ................................ 227/136 X |
| 3,735,762 | 5/1973 | Bryan et al. . |
| 3,788,303 | 1/1974 | Hall . |
| 3,815,476 | 6/1974 | Green et al. . |
| 3,819,100 | 6/1974 | Noiles et al. . |
| 3,837,555 | 9/1974 | Green . |
| 3,892,228 | 7/1975 | Mitsui . |
| 3,949,924 | 4/1976 | Green . |
| 4,086,926 | 5/1978 | Green et al. . |
| 4,111,206 | 9/1978 | Vishnevsky et al. . |
| 4,169,476 | 10/1979 | Hiltebrandt . |
| 4,207,873 | 6/1980 | Kruy . |
| 4,273,129 | 6/1981 | Boebel . |
| 4,331,277 | 5/1982 | Green . |
| 4,349,028 | 9/1982 | Green ..................................... 227/19 |
| 4,383,634 | 5/1983 | Green . |
| 4,429,695 | 2/1984 | Green . |
| 4,520,817 | 6/1985 | Green . |
| 4,562,839 | 1/1986 | Blake, III et al. . |
| 4,566,620 | 1/1986 | Green et al. . |
| 4,573,468 | 3/1986 | Conta et al. . |
| 4,573,622 | 3/1986 | Green et al. . |
| 4,580,712 | 4/1986 | Green . |
| 4,606,343 | 8/1986 | Conta et al. . |
| 4,610,383 | 9/1986 | Rothfuss et al. . |
| 4,671,445 | 6/1987 | Barker et al. . |
| 4,688,555 | 8/1987 | Wardle . |
| 4,714,187 | 12/1987 | Green . |
| 4,715,520 | 12/1987 | Roehr, Jr. et al. . |
| 4,728,020 | 3/1988 | Green et al. . |
| 4,754,909 | 7/1988 | Barker et al. . |
| 4,763,669 | 8/1988 | Jaeger . |
| 4,784,137 | 11/1988 | Kulik et al. . |
| 4,819,853 | 4/1989 | Green . |
| 4,821,942 | 4/1989 | Richards et al. . |
| 4,848,637 | 7/1989 | Pruitt . |
| 4,880,015 | 11/1989 | Nierman . |
| 4,938,408 | 7/1990 | Bedi et al. ................................ 227/19 |
| 4,941,623 | 7/1990 | Pruitt . |
| 4,944,443 | 7/1990 | Oddsen et al. . |
| 4,955,959 | 9/1990 | Tompkins et al. . |
| 4,978,049 | 12/1990 | Green . |
| 5,018,657 | 5/1991 | Pedlick et al. . |
| 5,040,715 | 8/1991 | Green et al. ................................ 227/8 |
| 5,042,707 | 8/1991 | Taheri . |
| 5,047,038 | 9/1991 | Peters et al. . |
| 5,071,430 | 12/1991 | de Salis et al. . |
| 5,170,925 | 12/1992 | Madden et al. ........................... 227/19 |
| 5,219,111 | 6/1993 | Bilotti et al. ............................. 227/19 |
| 5,478,003 | 12/1995 | Green et al. . |

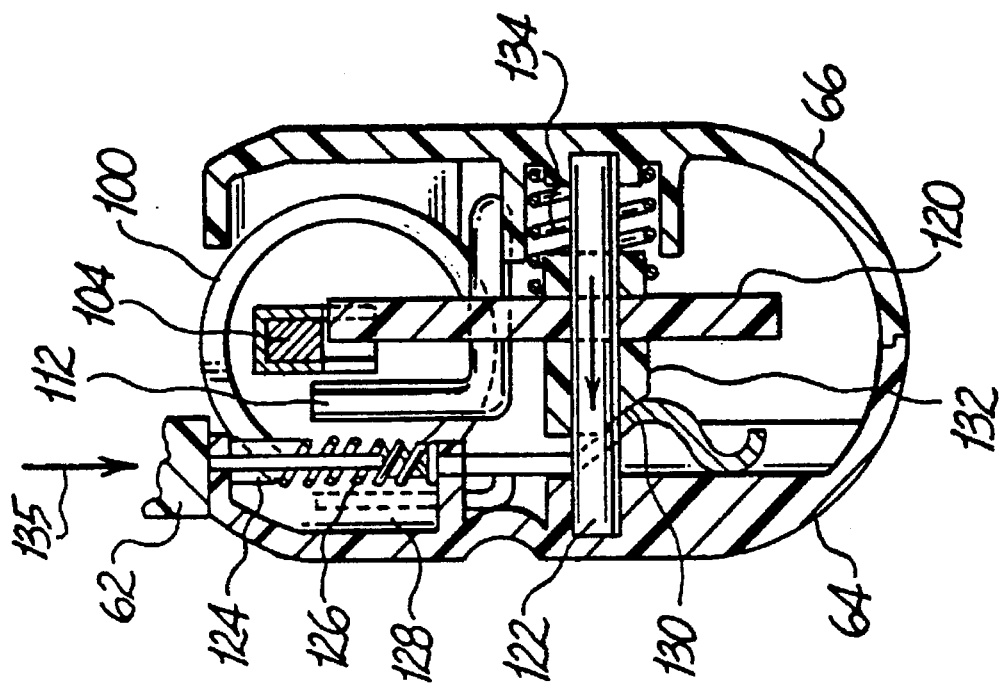
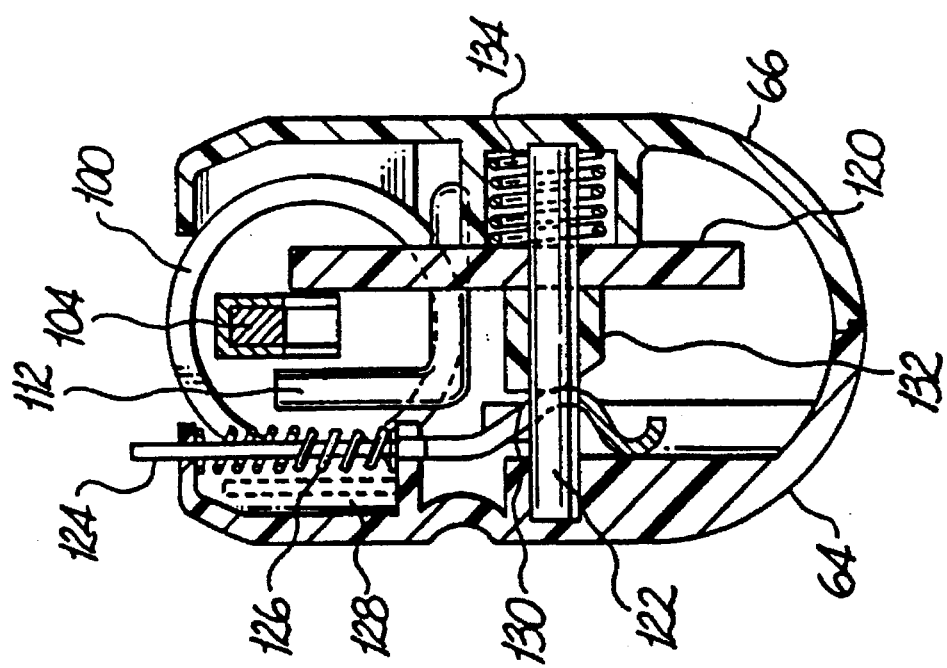

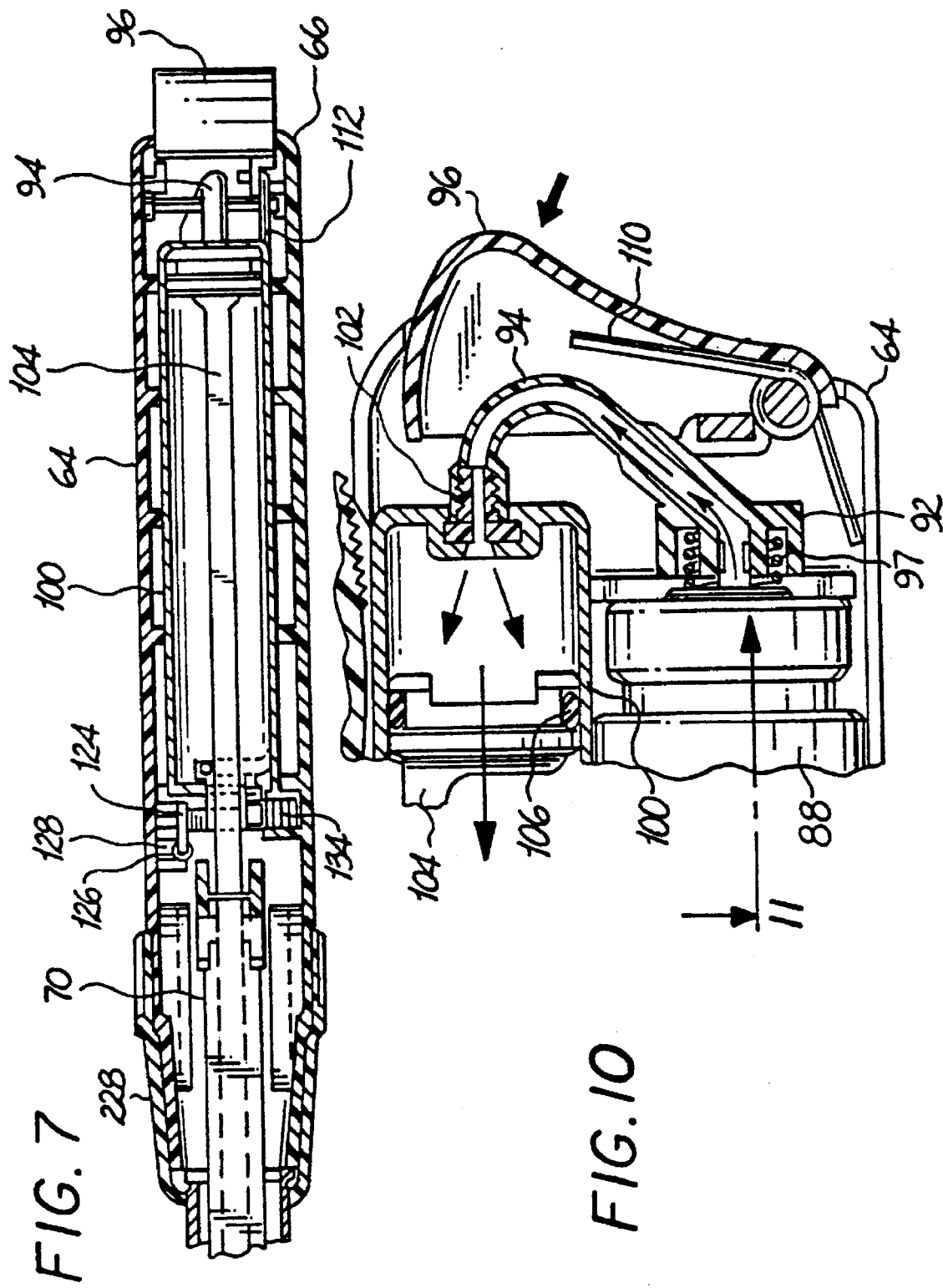

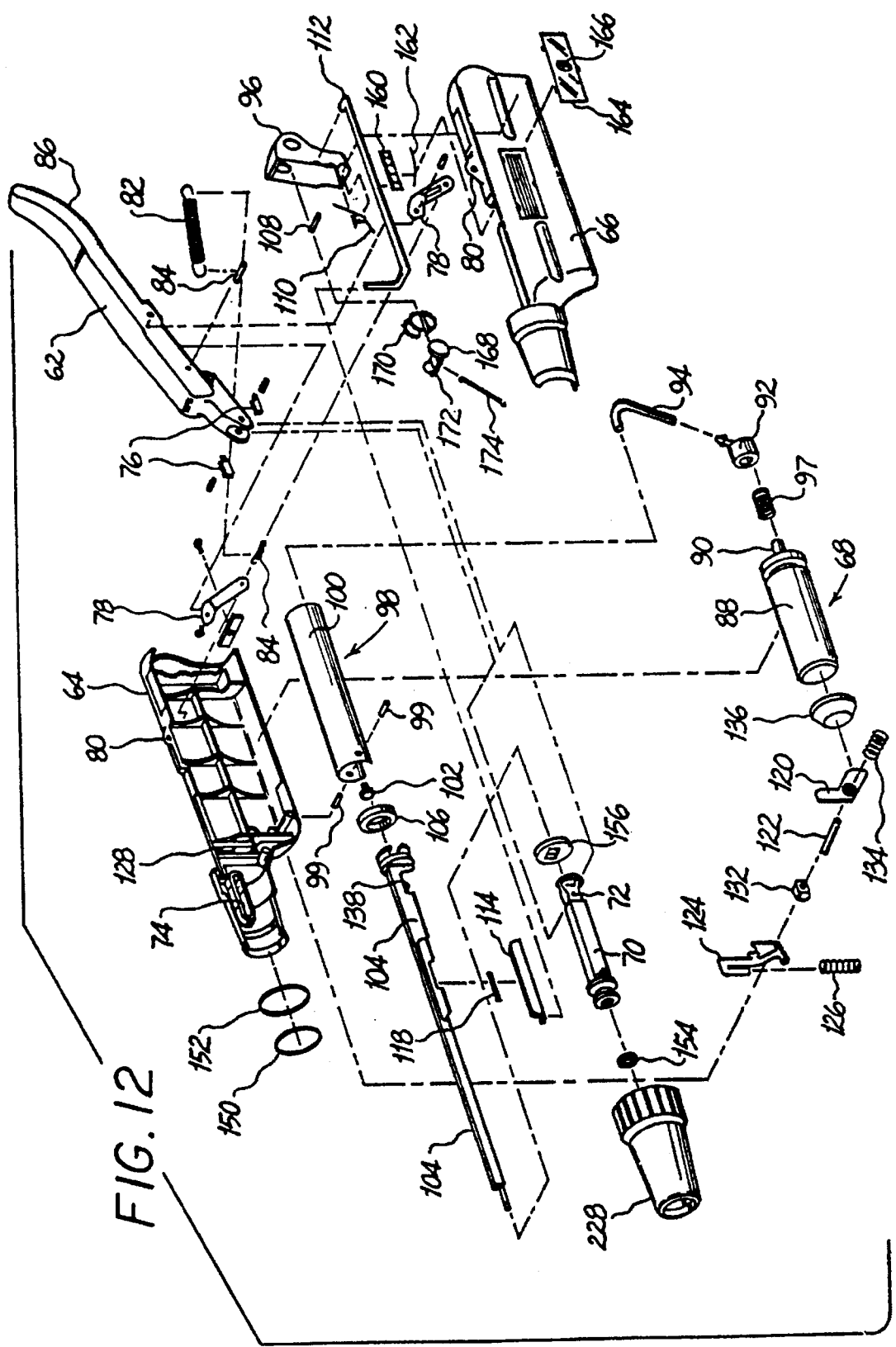

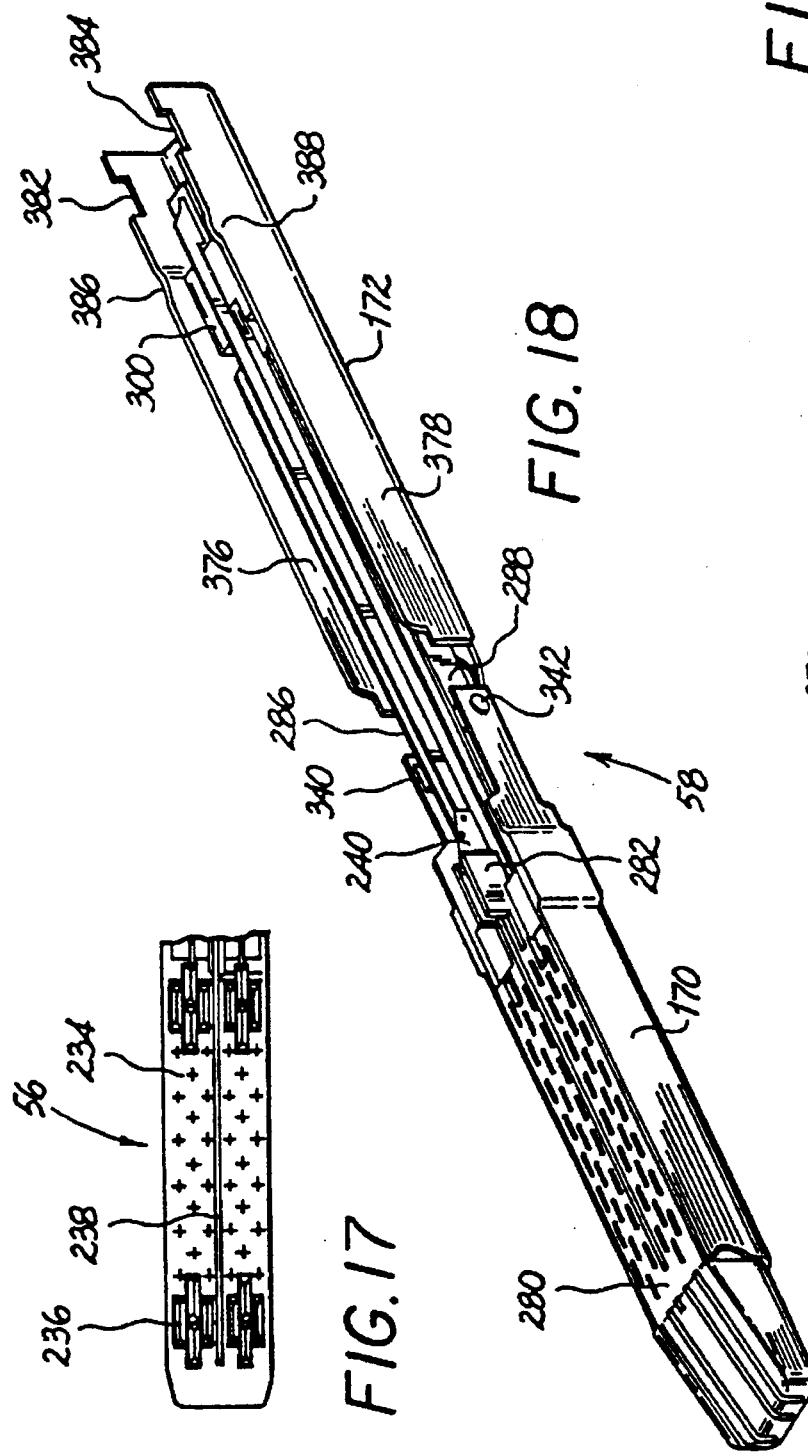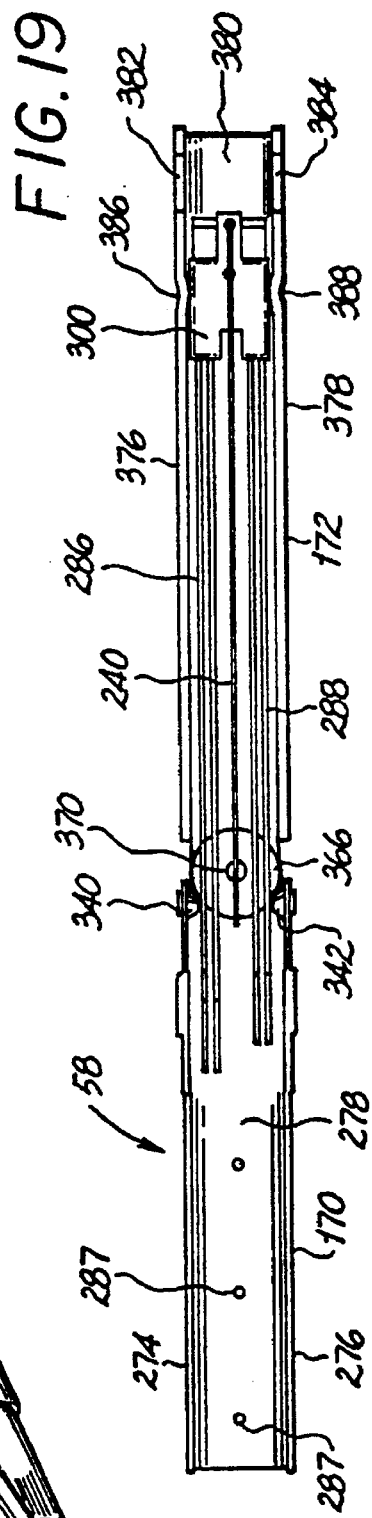

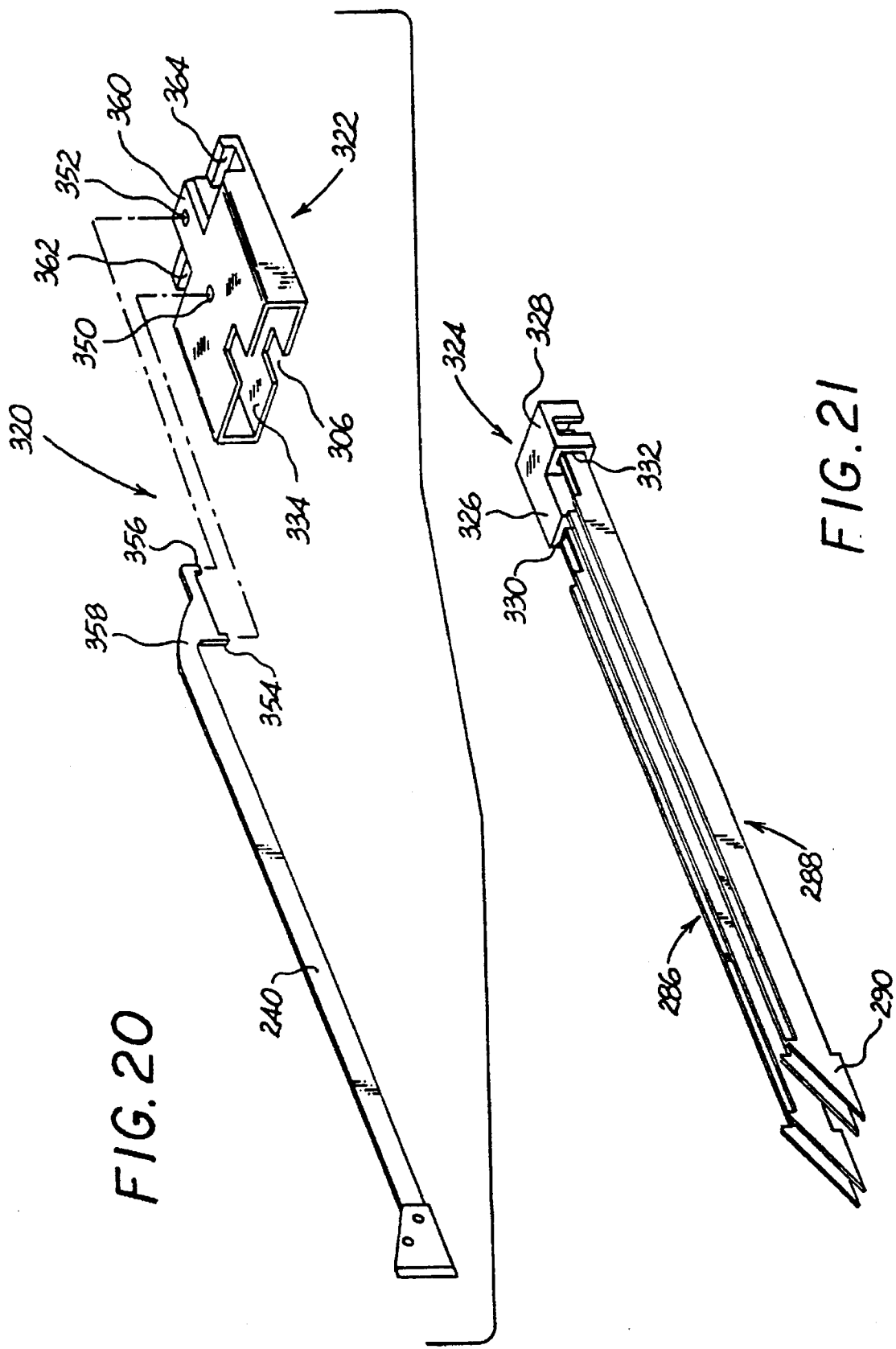

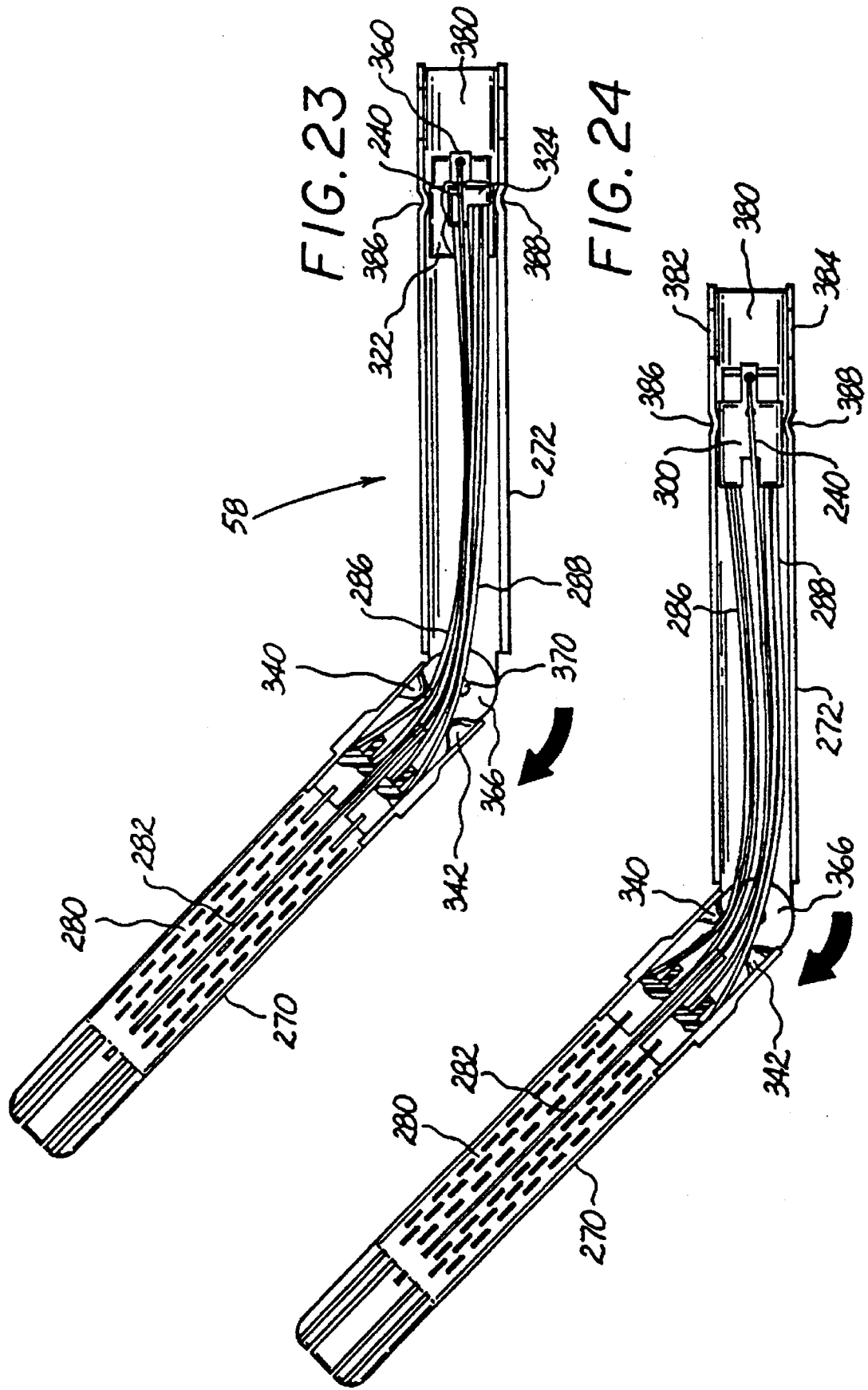

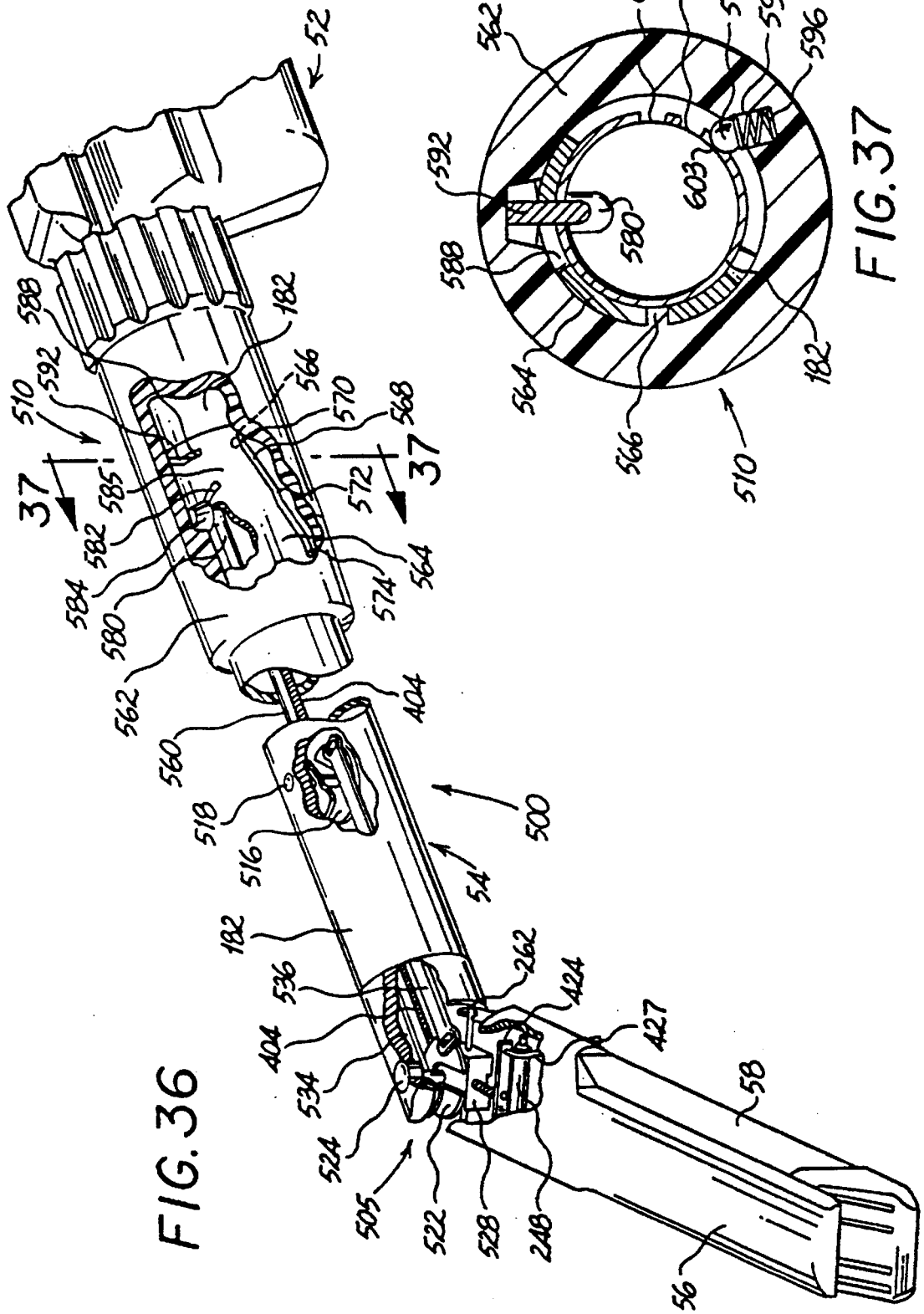

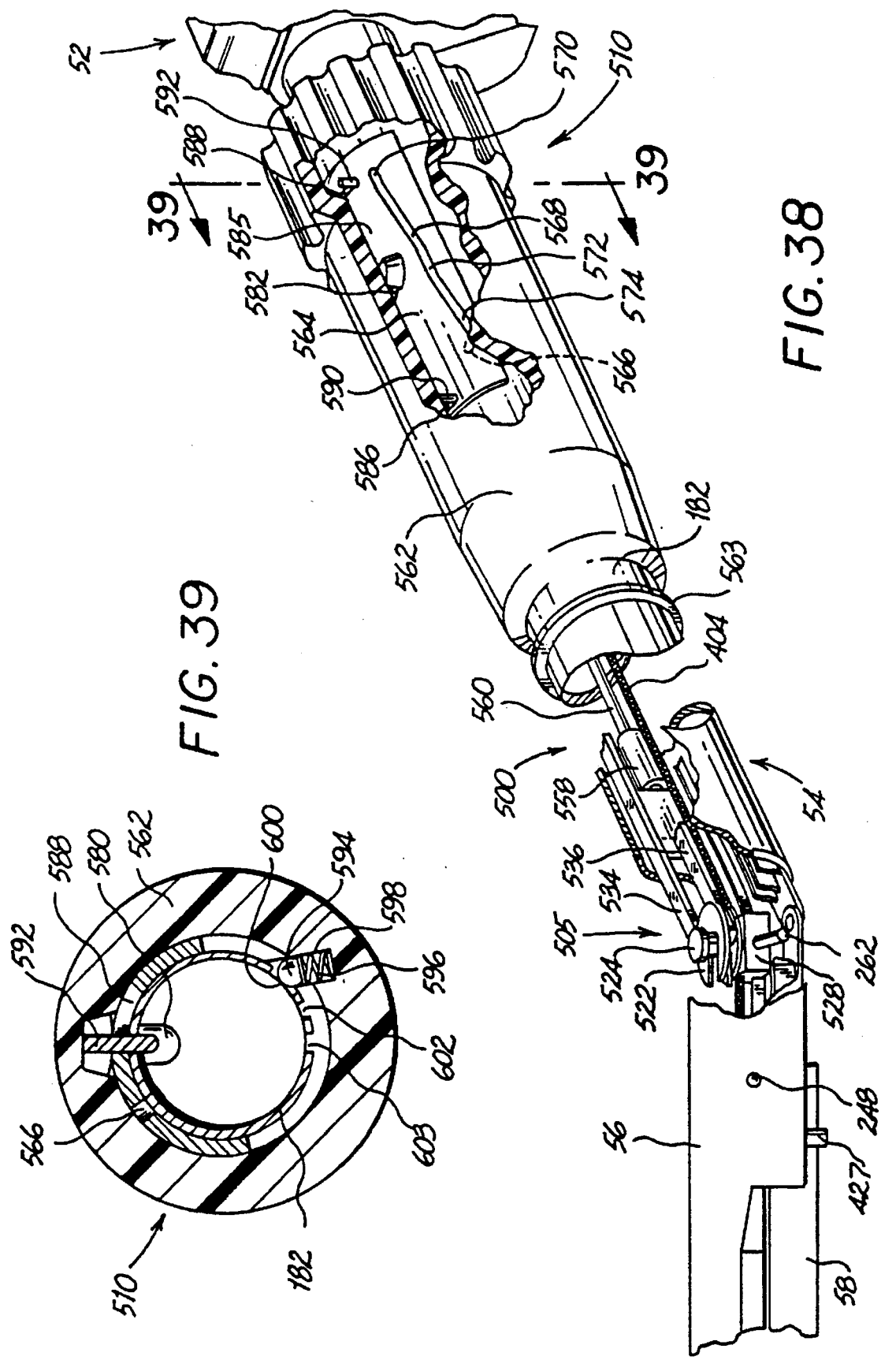

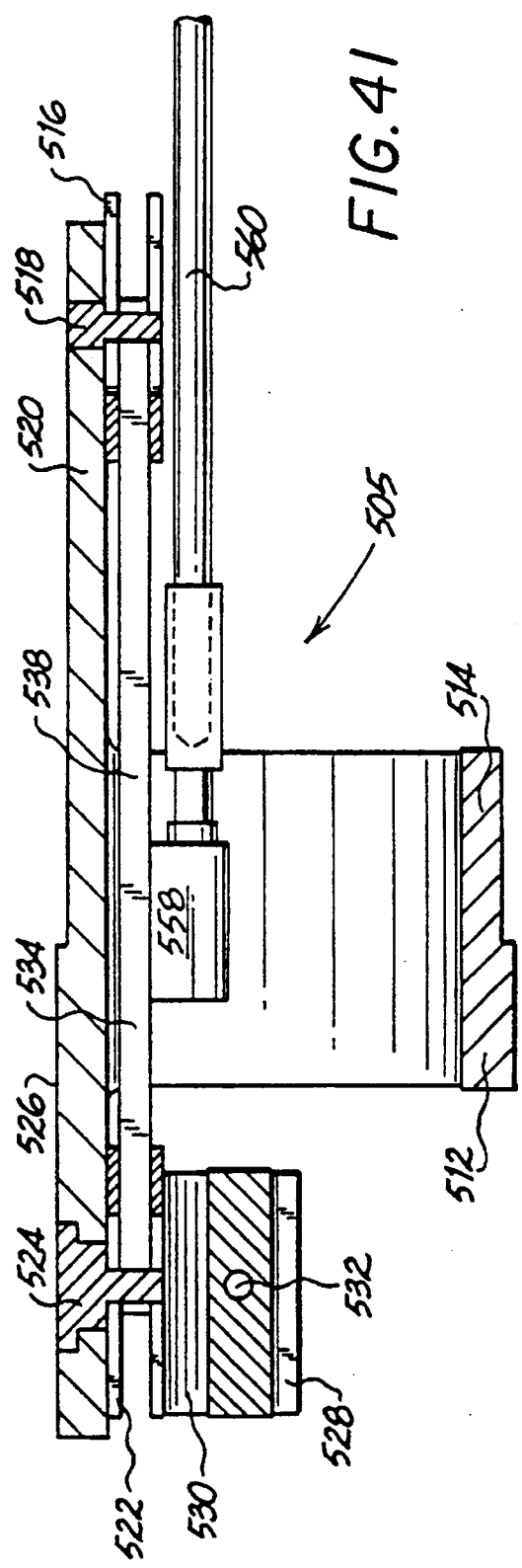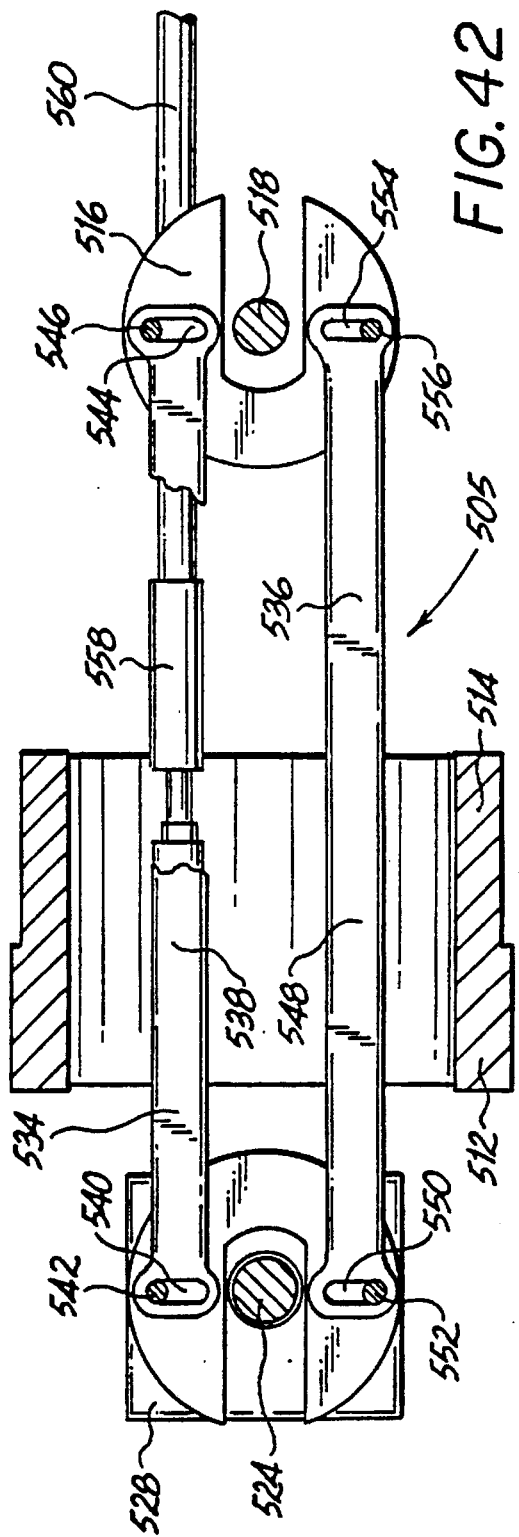

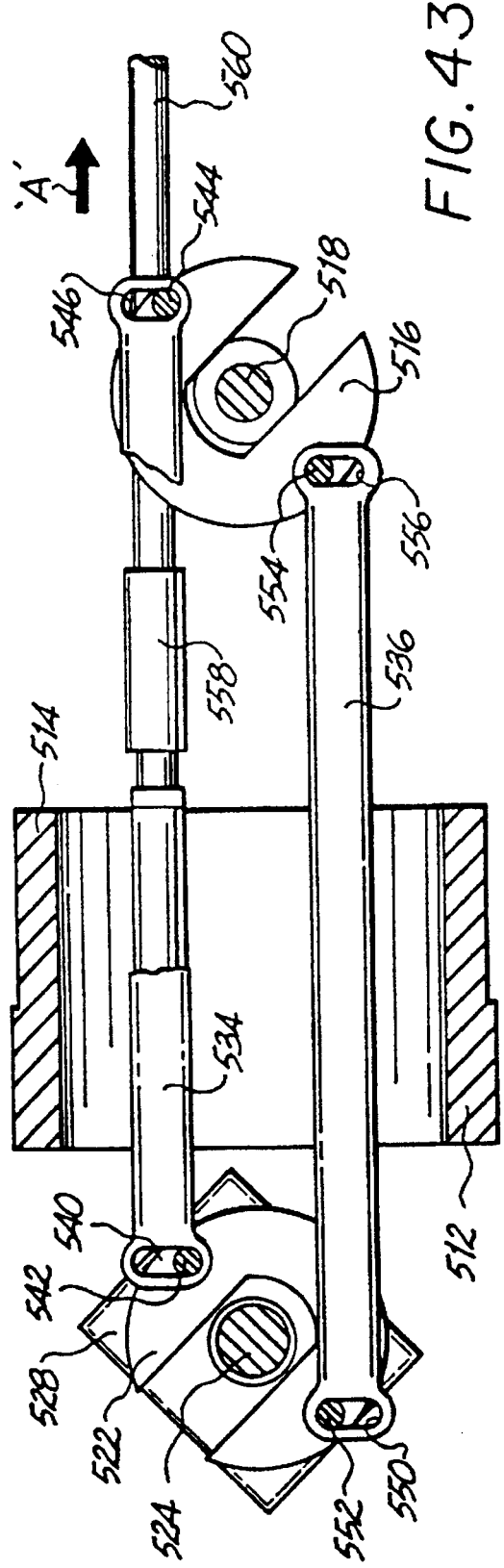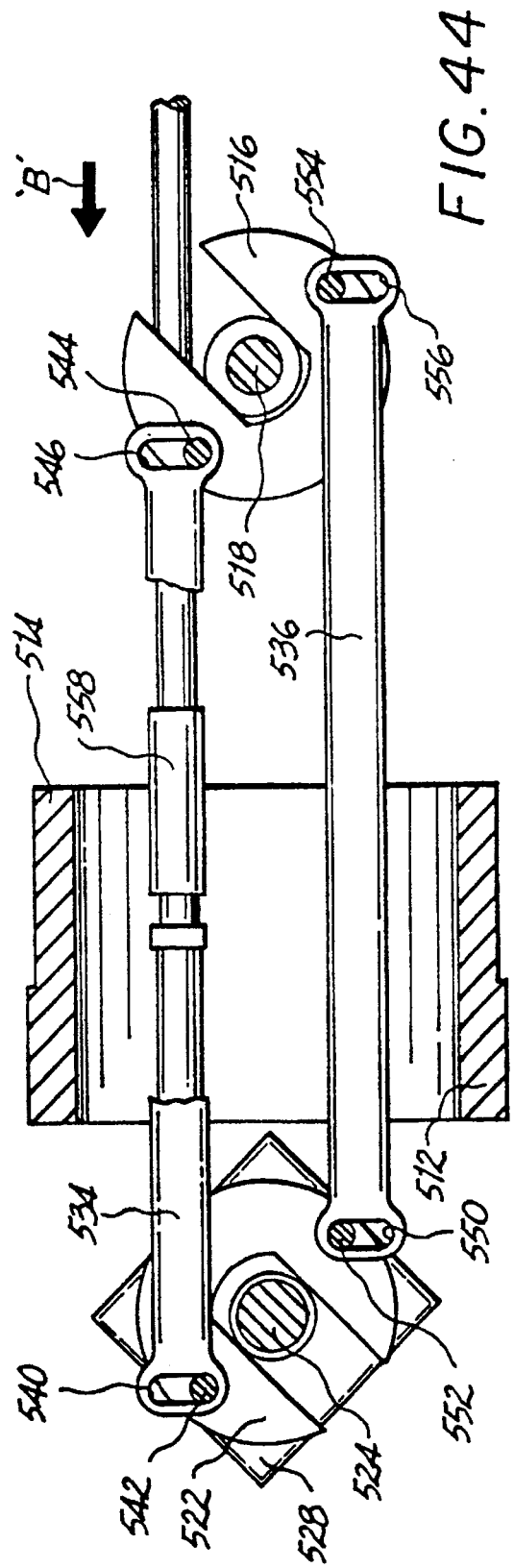

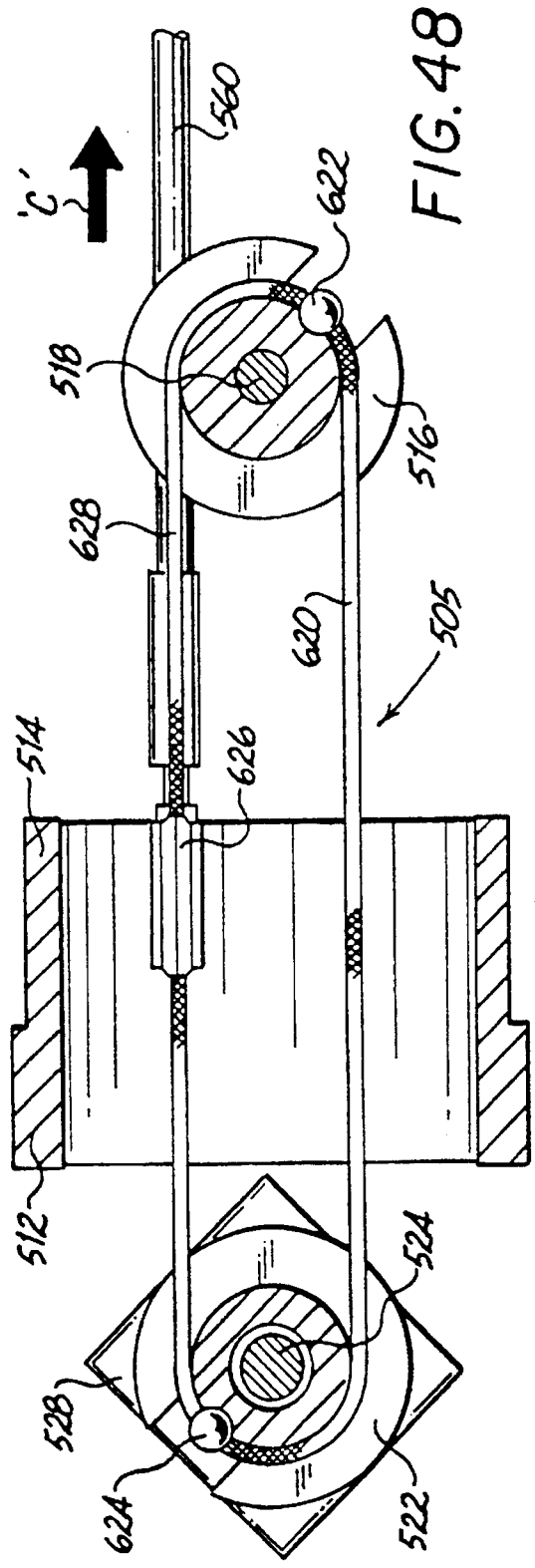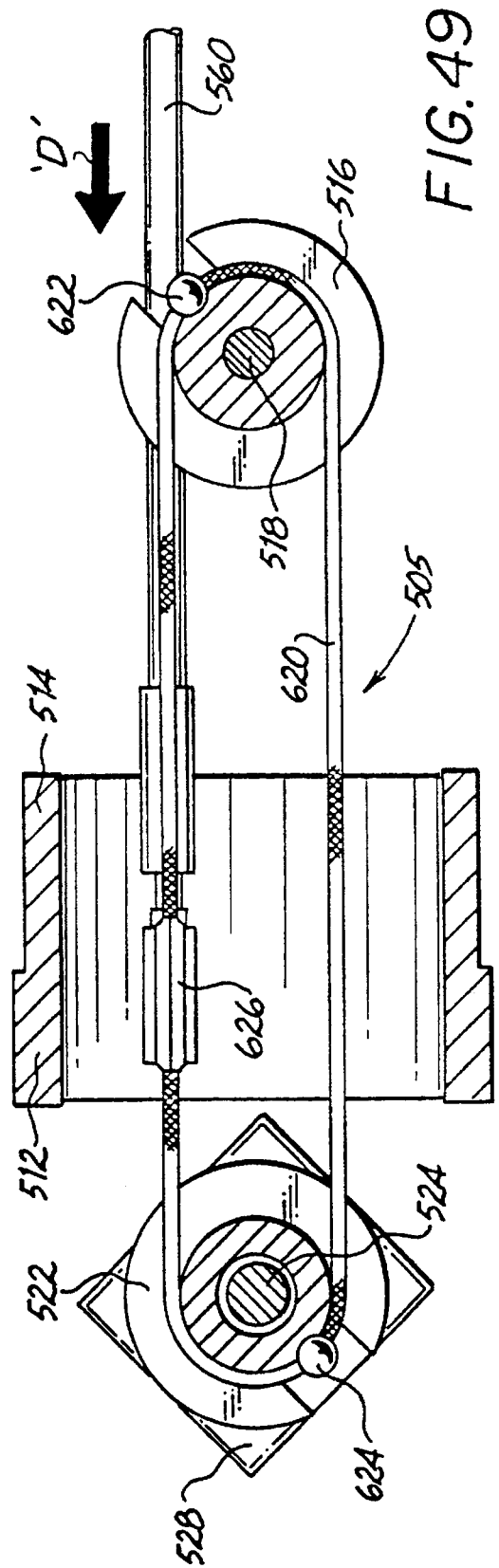

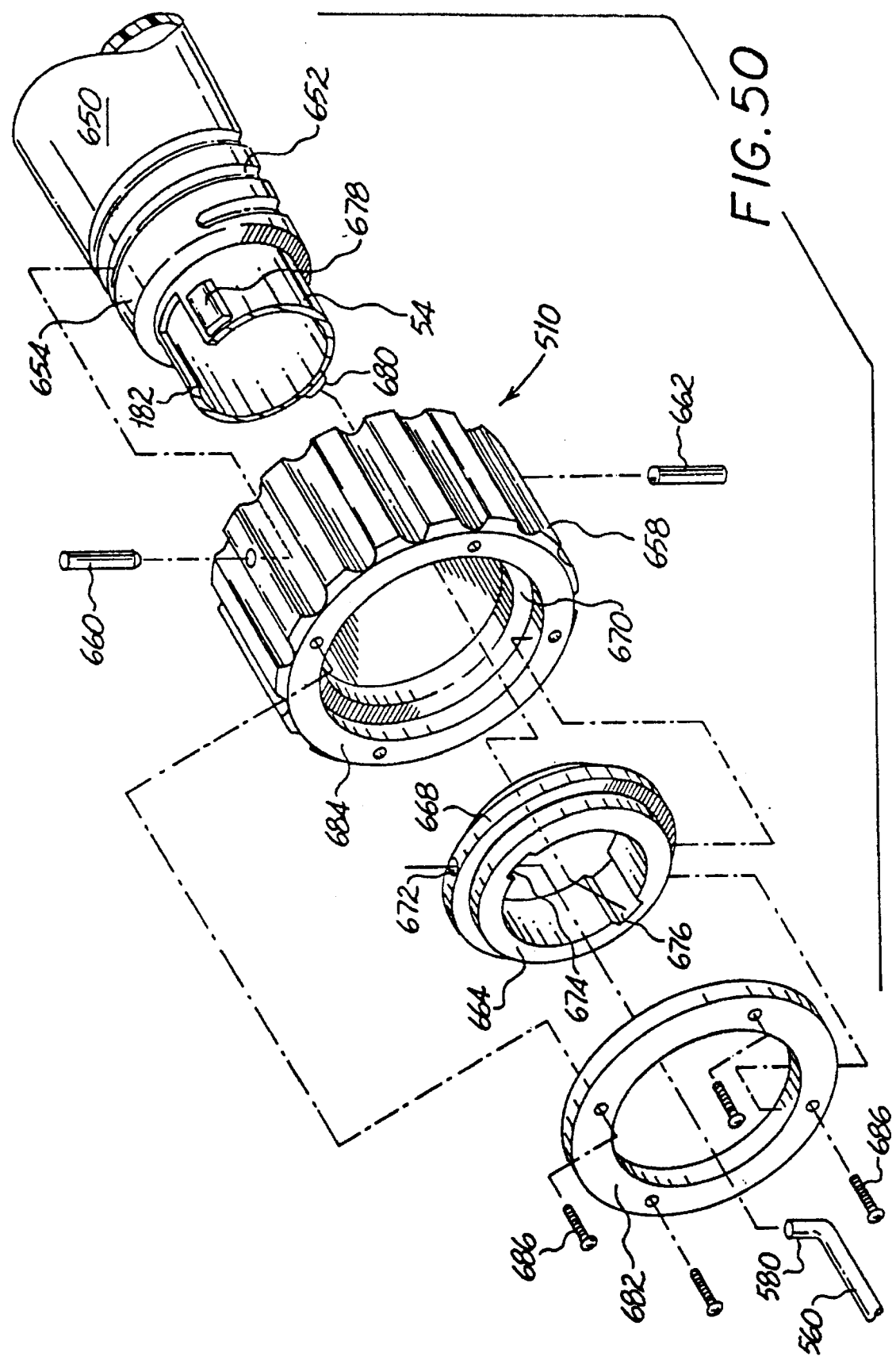

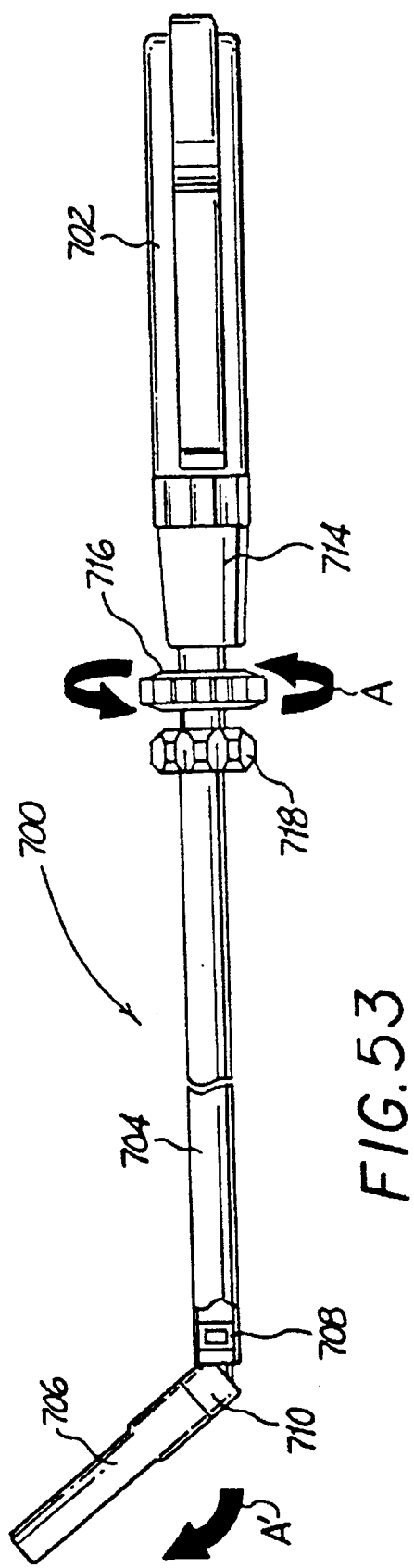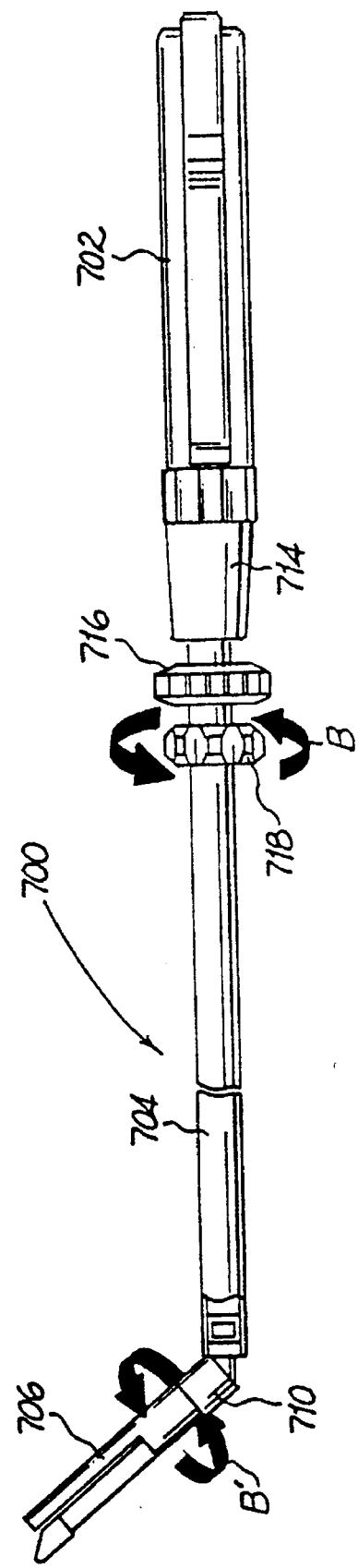
FIG. 53
FIG. 54

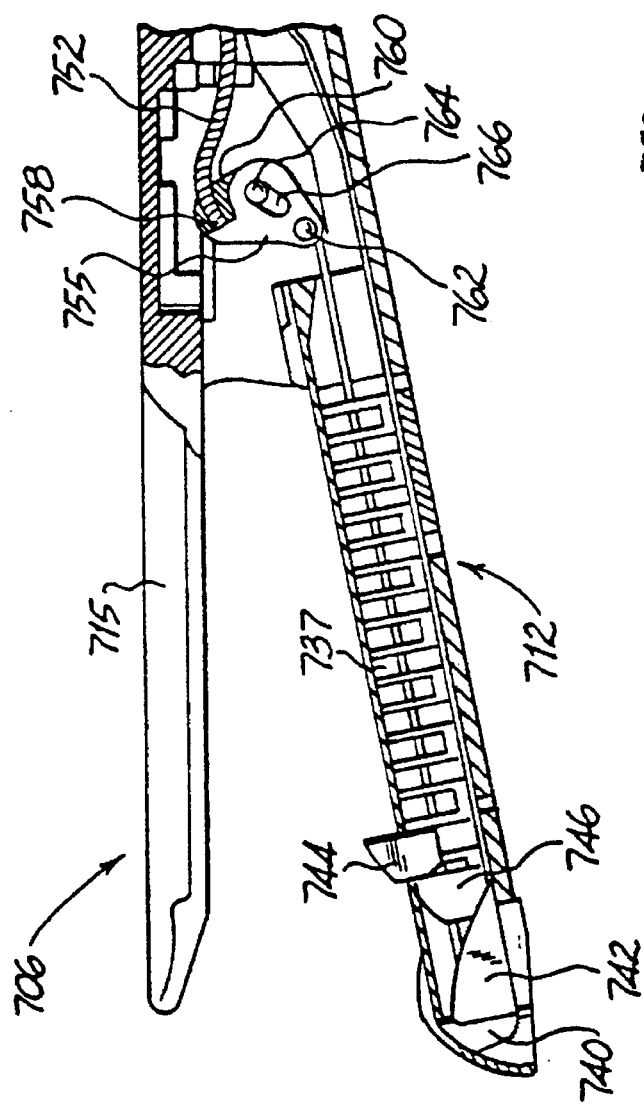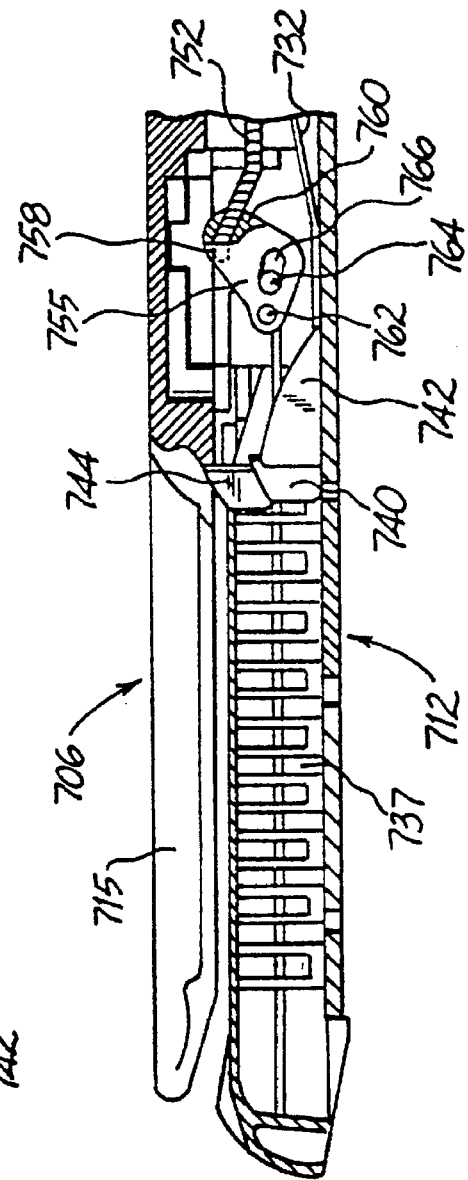

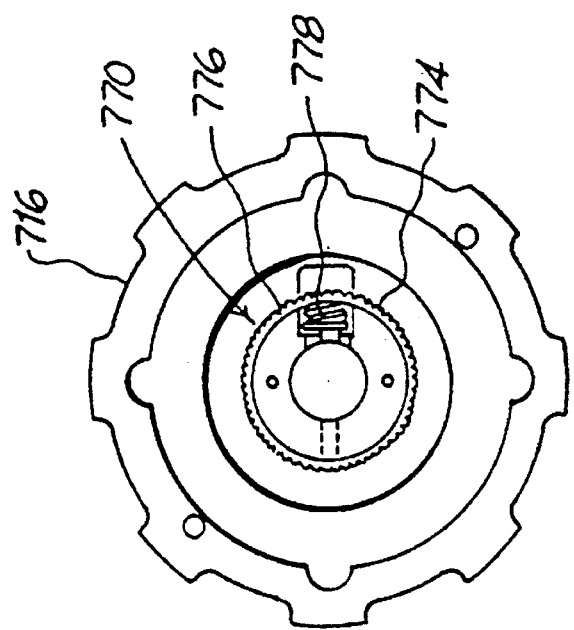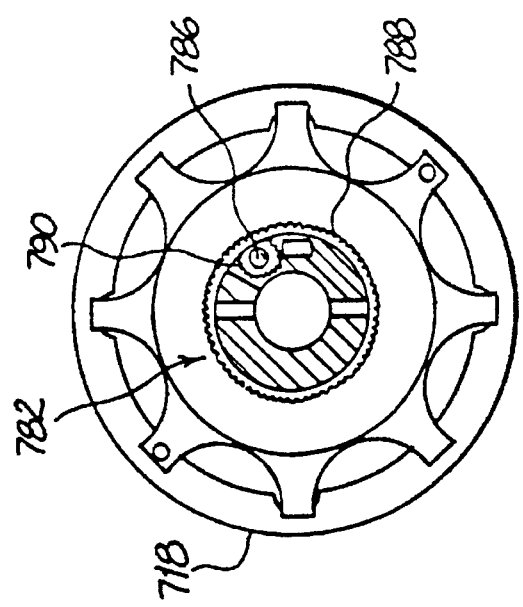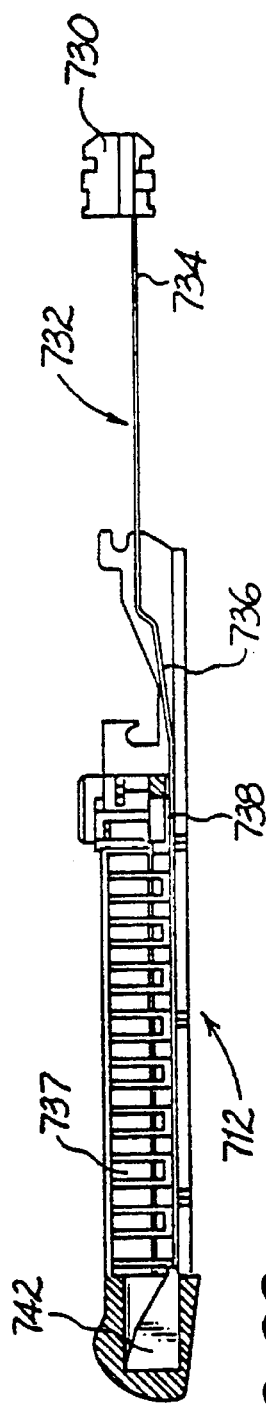

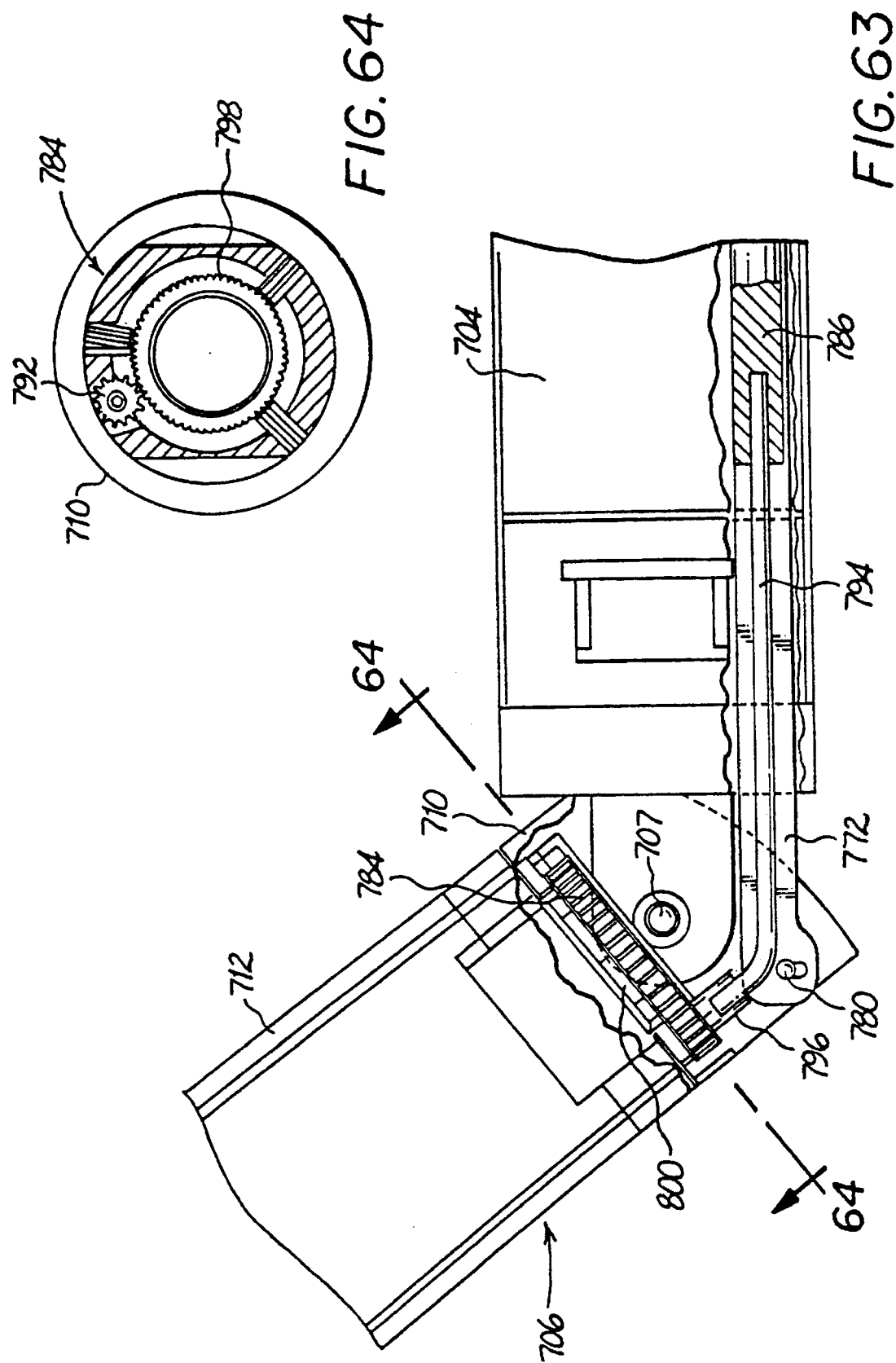

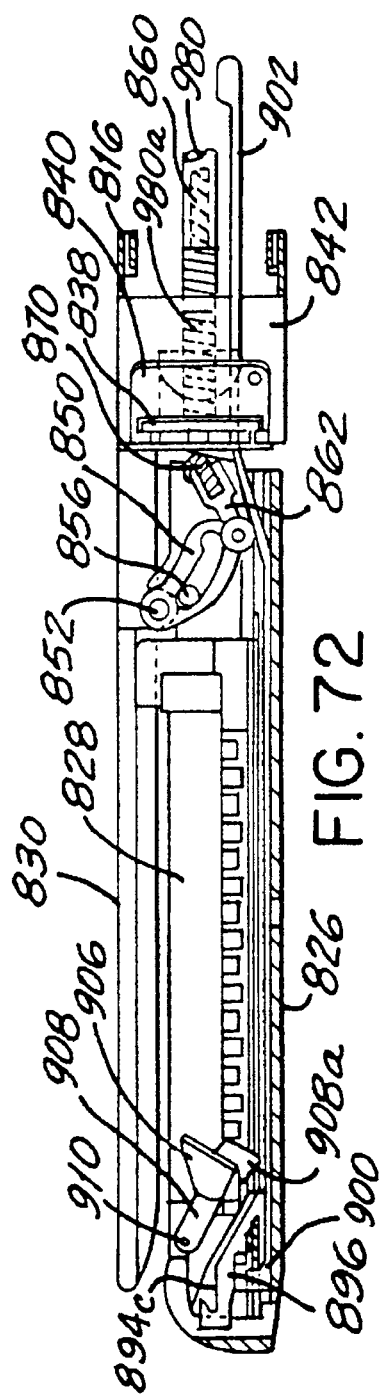
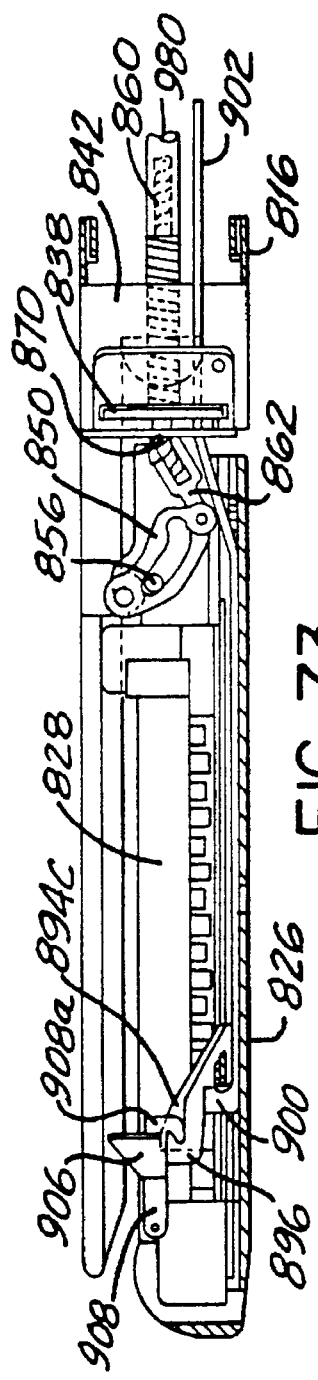
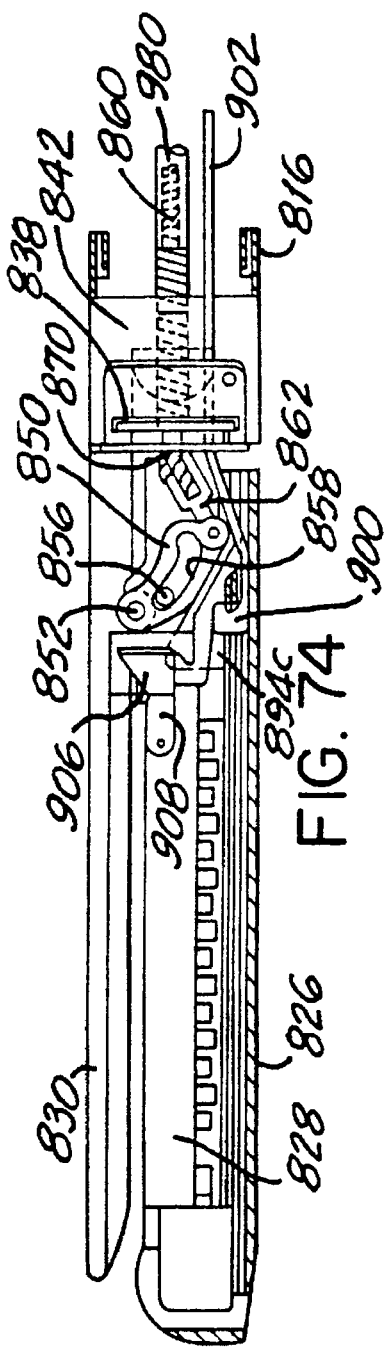

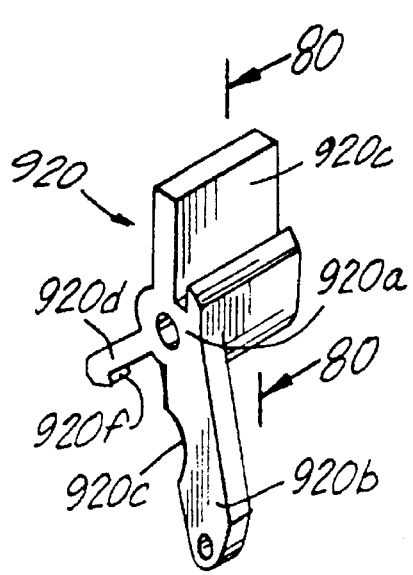
FIG. 78
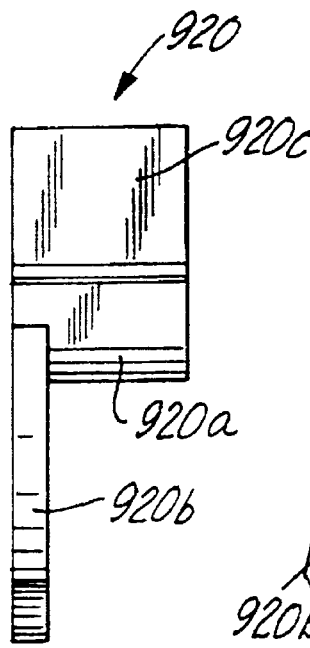
FIG. 79
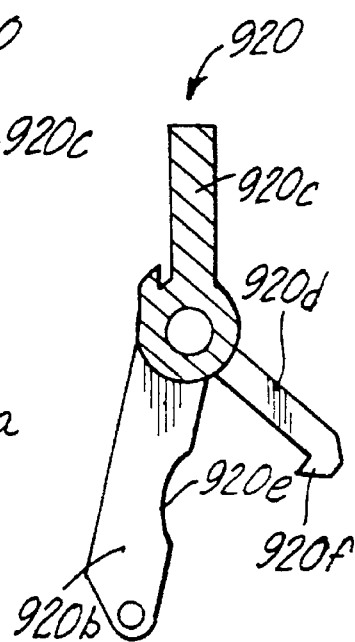
FIG. 80
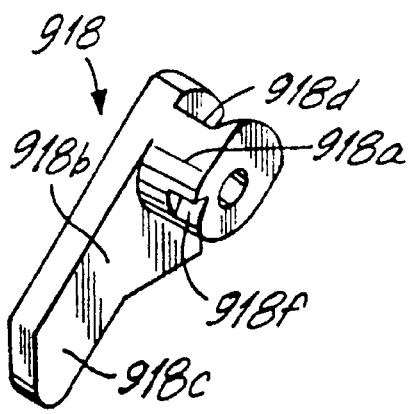
FIG. 81
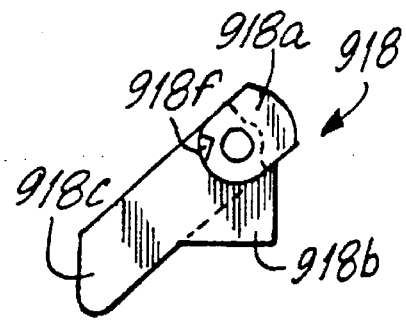
FIG. 83
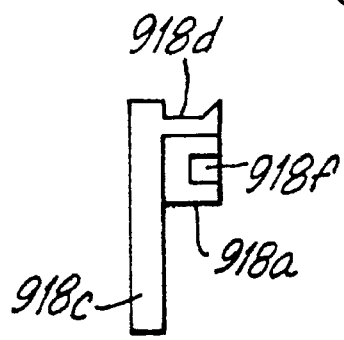
FIG. 82
FIG. 84

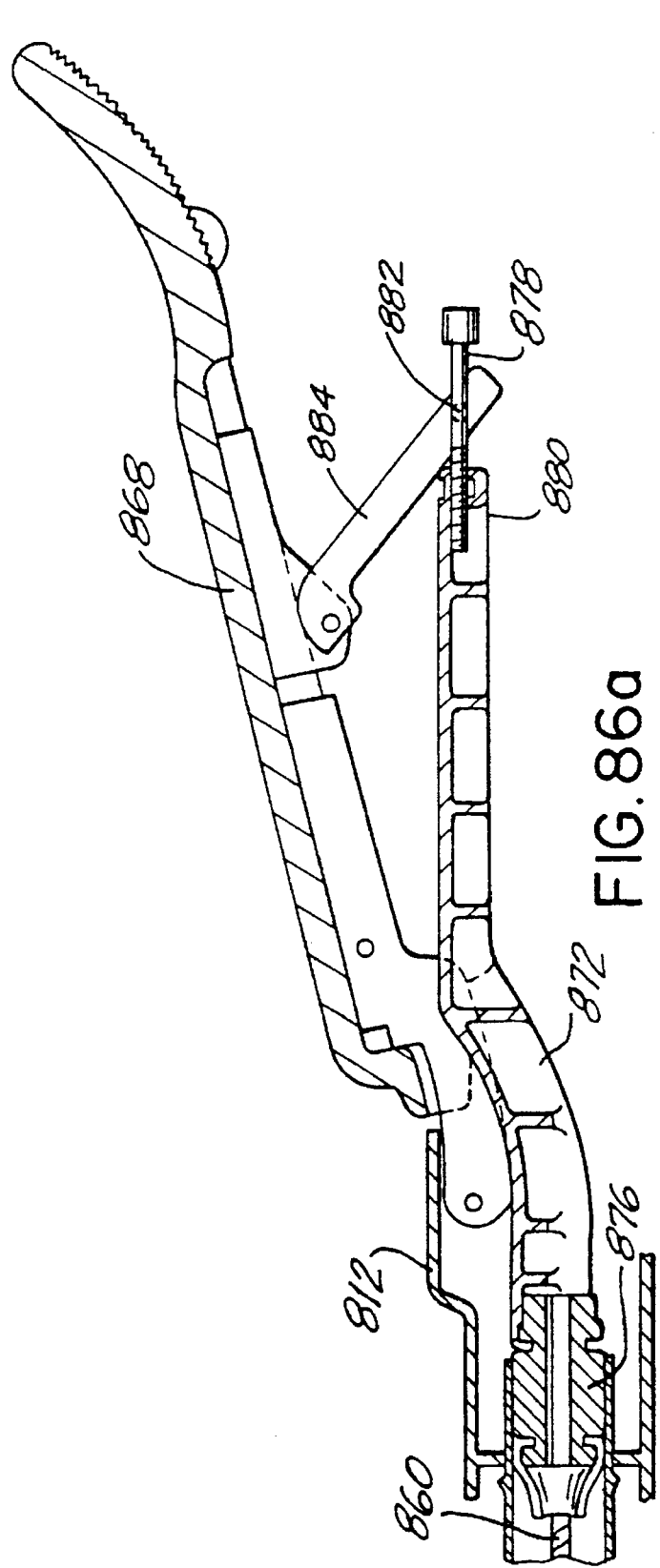
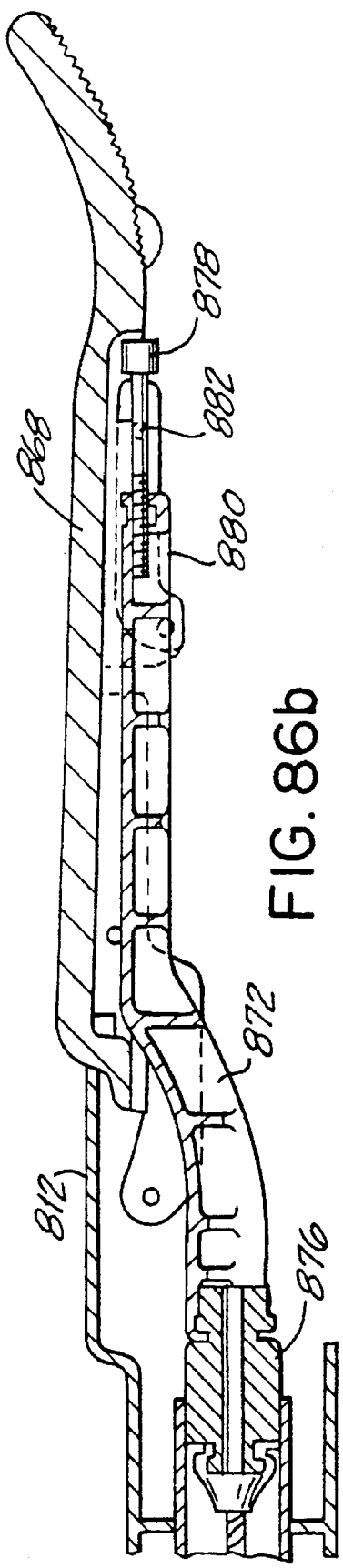
FIG. 86a
FIG. 86b

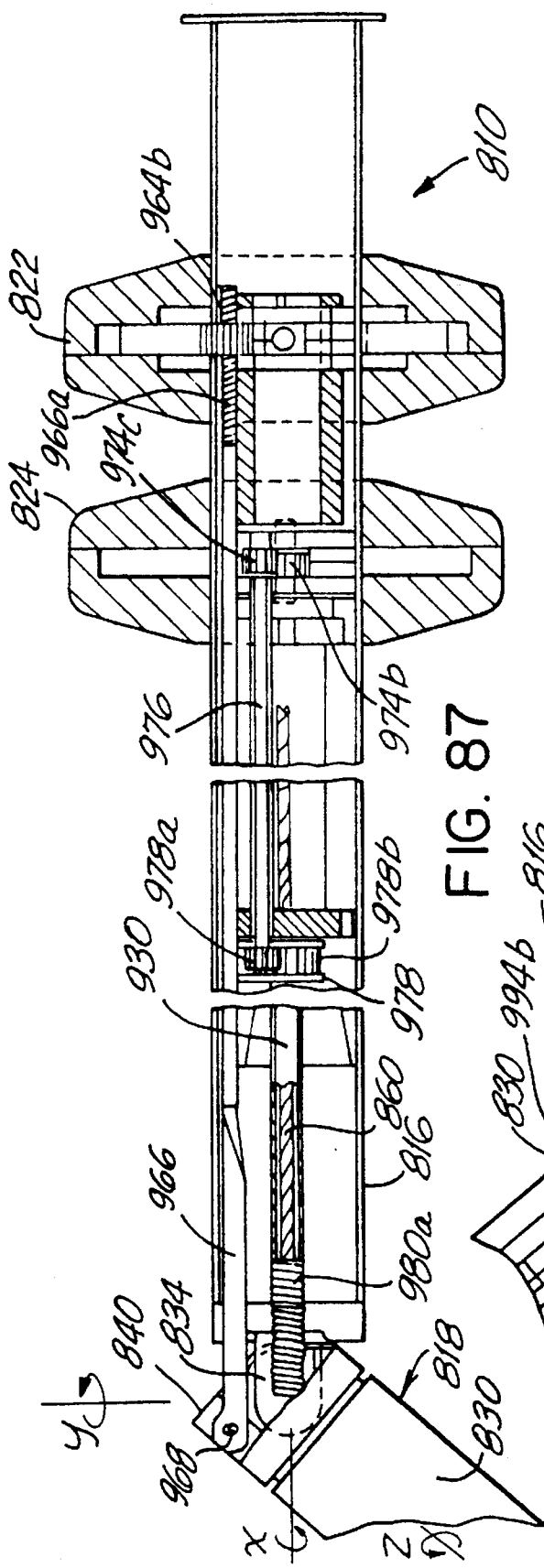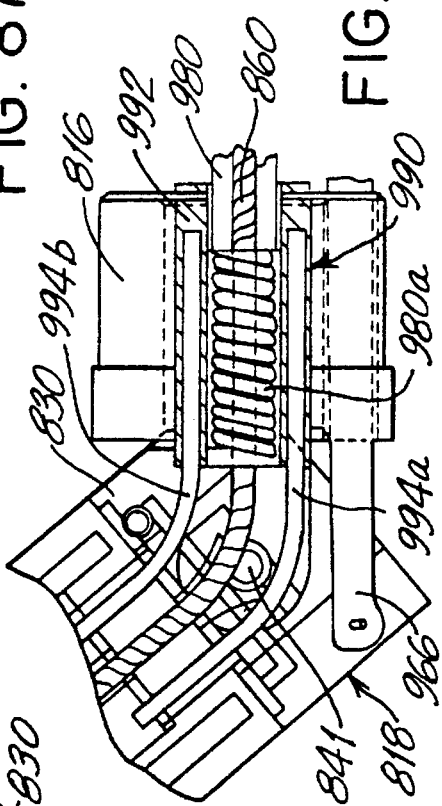

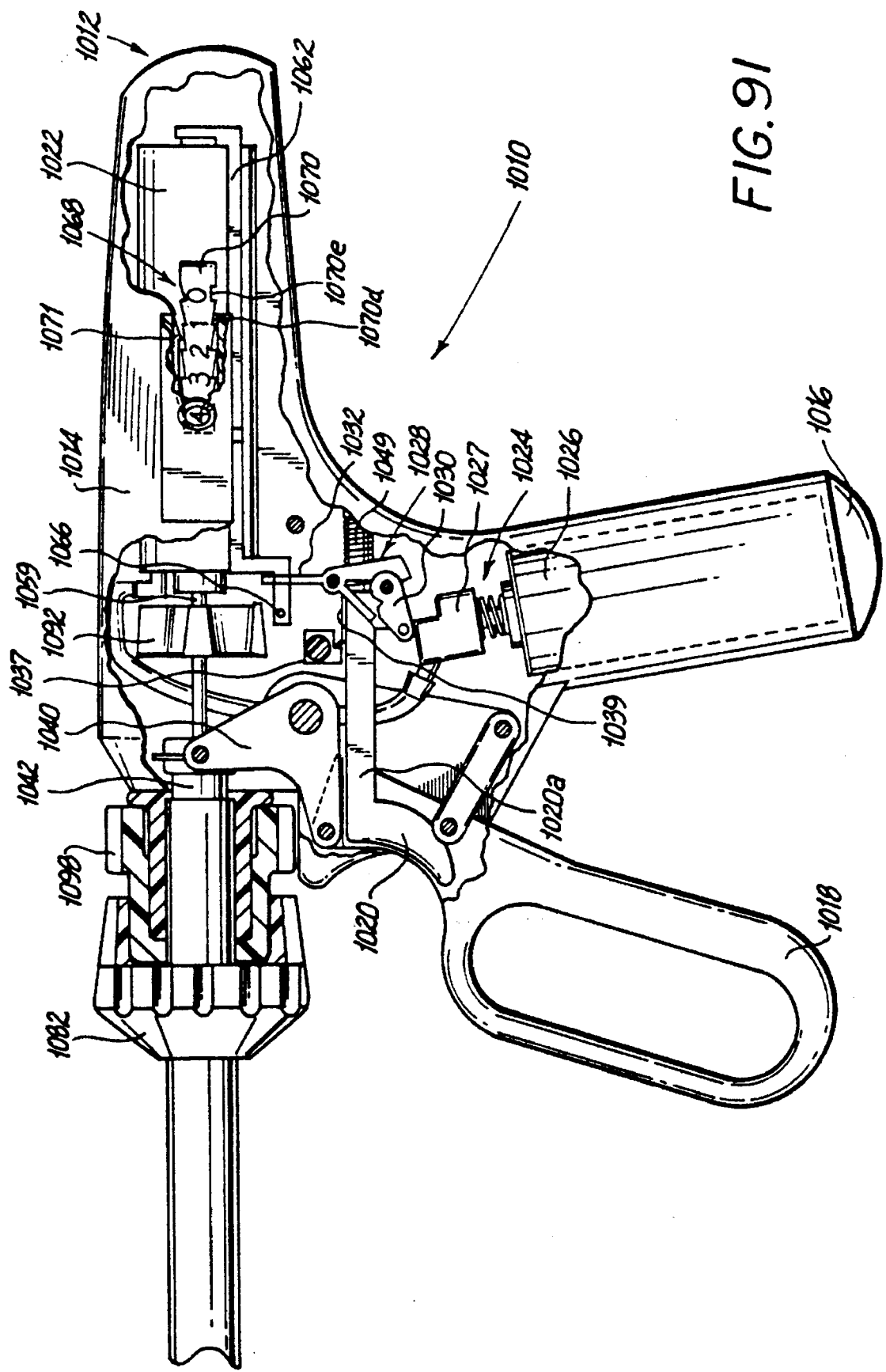

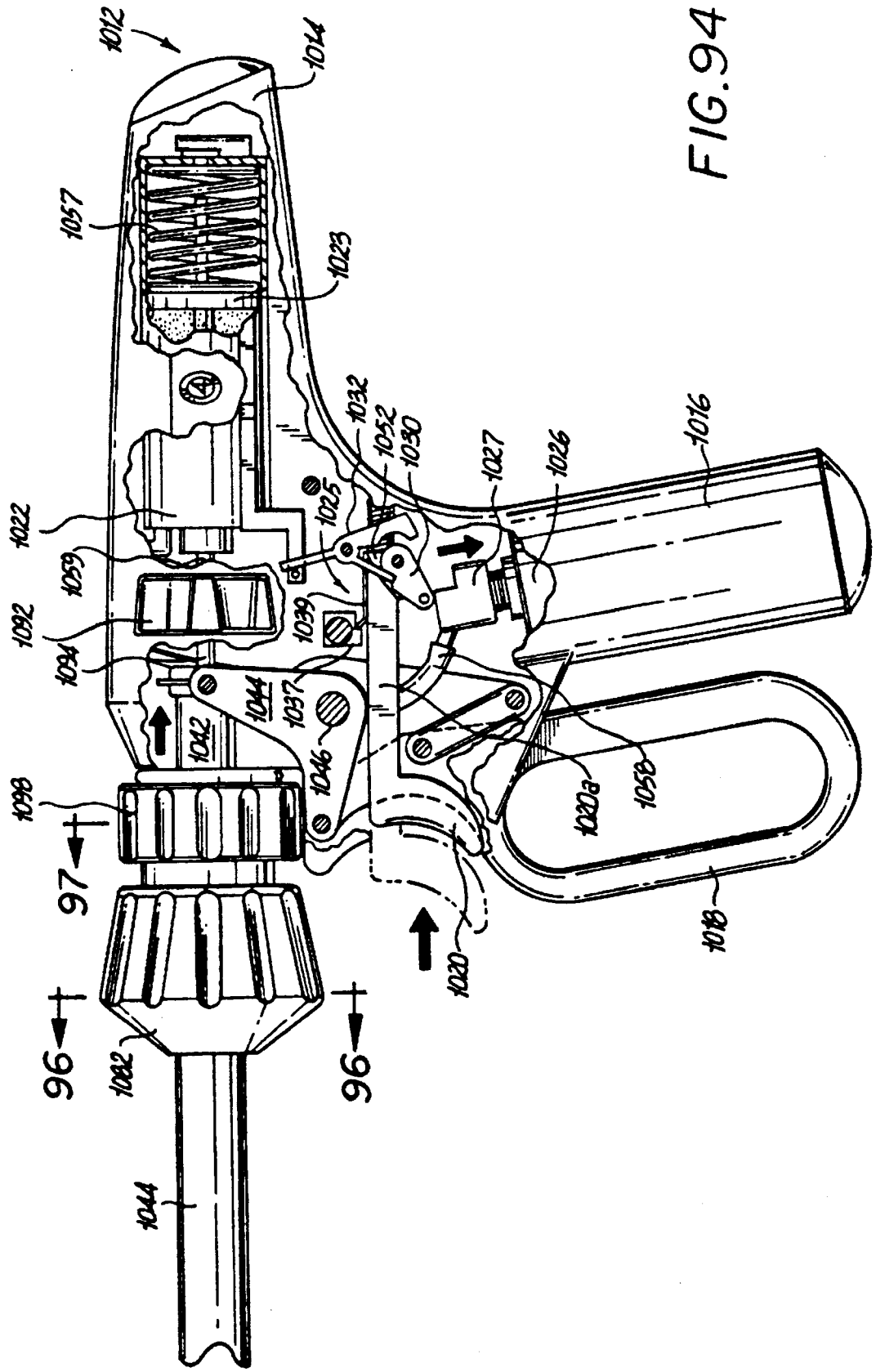

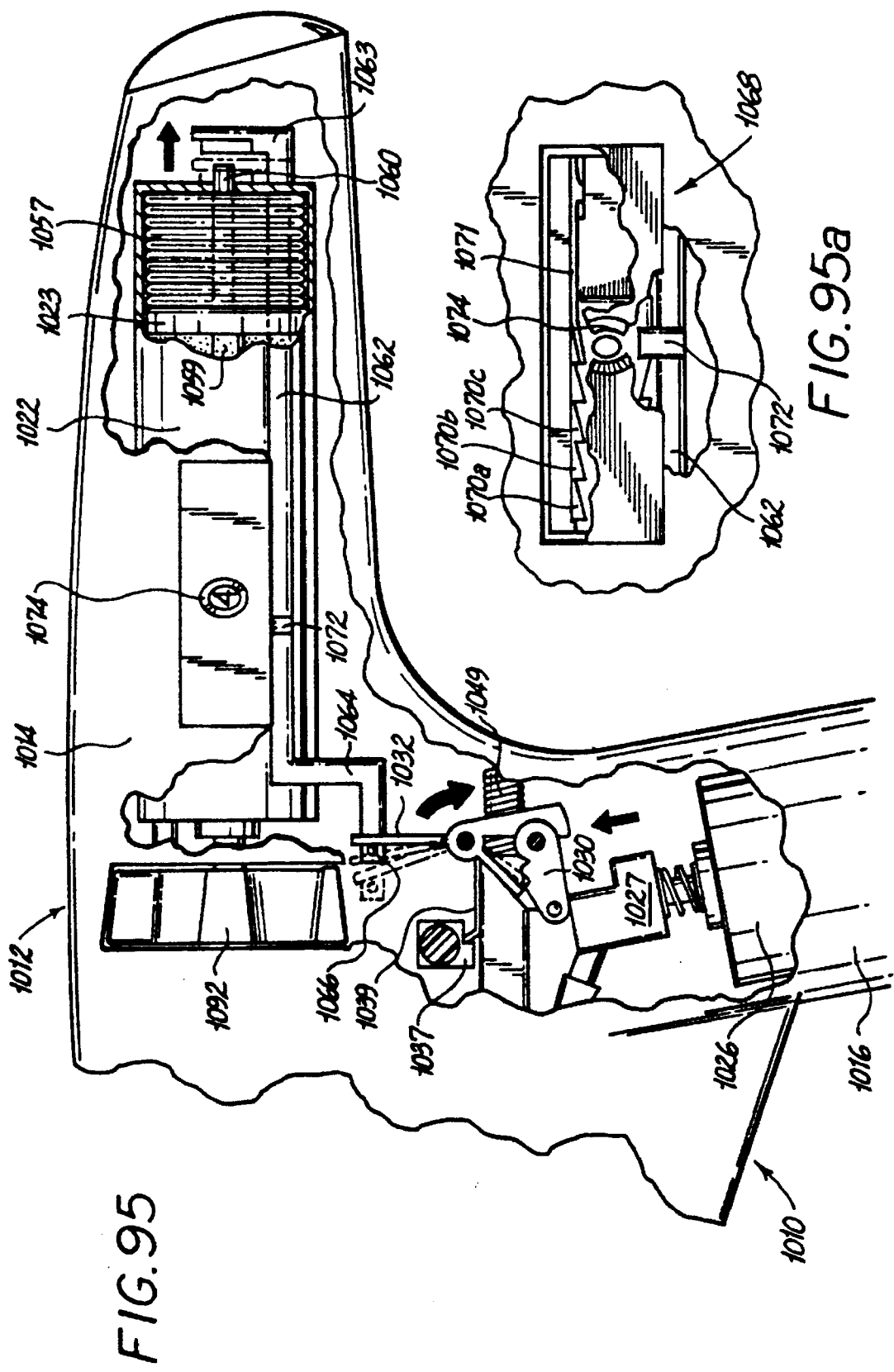

SELF CONTAINED GAS POWERED SURGICAL APPARATUS

CROSS REFERENCE TO RELATED APPLICATIONS

This is a divisional, of U.S. application Ser. No. 08/133,549 filed Oct. 8, 1993, now U.S. Pat. No. 5,478,003 which is a continuation-in-part of application Ser. No. 08/024,533, filed Mar. 1, 1993, now U.S. Pat. No. 5,312,023, which is a continuation-in-part of application Ser. No. 07/949,685, filed Sep. 23, 1992, now U.S. Pat. No. 5,326,013, which is a continuation-in-part of application Ser. No. 07/915,425, filed Jul. 17, 1992, now abandoned which is a continuation-in-part of application Ser. No. 07/781,012, filed Oct. 18, 1991, now abandoned.

BACKGROUND OF THE INVENTION

1. Field of the Invention

This invention relates to surgical stapling apparatus, and more particularly to surgical apparatus which are powered by serf contained relatively low pressure gas systems to perform sequential operations such as tissue clamping, staple forming and/or tissue cutting.

2. Description of Related Art

Surgical stapling apparatus is known wherein tissue is first grasped or clamped between opposing jaw structure and then fastened by means of fasteners. In some instruments a knife is provided to cut tissue which has been joined. The fasteners are typically in the form of surgical staples. However, two part polymeric type fasteners are also known.

Instruments for this purpose can comprise two elongated fingers which are respectively used to capture or clamp tissue. Typically, one of the fingers carries a disposable cartridge housing wherein a plurality of staples are arranged in at least two lateral rows while the other finger comprises an anvil for curling the staple legs into a hook-like configuration upon their being driven against the anvil. The stapling operation is effected by a pusher which travels longitudinally along the cartridge carrying finger, with the pusher acting upon the staples to place rows of staples in body tissue. A knife may be optionally positioned in such a manner so as to operate sequentially immediately behind the pusher, and laterally positioned between the staple rows to longitudinally cut and/or open the stapled tissue between the rows of staples. Such instruments are disclosed in Bobrov et al. (U.S. Pat. No. 3,079,606) and Green (U.S. Pat. No. 3,490,675). These instruments comprise apparatus for simultaneously making a longitudinal incision and applying a row of staples on both sides of the incision.

A later development disclosed in Green (U.S. Pat. No. 3,499,591) applies a double row of staples on each side of the incision. This is accomplished by a cartridge assembly wherein a cam member moves within a guide path between two sets of staggered staple carrying grooves. Staple drive members located within the grooves each have two staple pusher plates, and sloping surfaces disposed within the guide path so as to be contacted by the longitudinally moving cam and be driven along the groove to effect ejection of two staples.

The cartridge assemblies typically come in a plurality of sizes, each varying in both length and number of staples contained therein. Depending on the procedure to be performed, the surgeon must select the appropriate cartridge assembly. No provision is currently available to adjust the firing means of the instrument itself so that a wide variety of staple driving sequences may be accomplished using a single staple cartridge assembly.

The instruments described above were all designed to be used in surgical procedures wherein surgeons have direct manual access to the operation site. However, in endoscopic or laparoscopic procedures surgery is performed through a small incision or through narrow cannulae inserted through small entrance wounds in the skin. In order to address the specific needs of endoscopic and/or laparoscopic surgical procedures, an endoscopic surgical stapling apparatus such as that shown in Green et al. (U.S. Pat. No. 5,040,715) has been developed. This apparatus is well suited for such procedures and incorporates a distal end having an anvil and staple cartridge assembly and a manually operated handle assembly interconnected by an endoscopic portion which permits the instrument to be inserted into a cannula and be remotely operated by the surgeon.

The instruments discussed above all require some degree of manually applied force in order to clamp, fasten and/or cut tissue. This manual application can prove awkward or difficult depending upon the orientation of the instrument relative to the surgeon, the type of tissue being operated on or the ability of the surgeon to apply the necessary force. Furthermore, because of the difficulty and expense of cleaning and sterilizing surgical instruments between uses, them is increasing interest in and demand for instruments which are disposable after use in a single surgical procedure rather than permanent and reusable. Self contained gas powered surgical staplers are known, as shown, for example, in U.S. Pat. Nos. 3,618,842; 3,643,851; 3,662,939; 3,717,294; 3,815,476; and 3,837,555. Typically, these staplers include a replaceable cylinder which supplies gas (e.g., carbon dioxide or nitrogen) at relatively high pressure (e.g., 800 p.s.i.g.) for powering the instrument. The high pressure gas used in these staplers requires that the staplers be of relatively heavy construction in order to accommodate the high pressure involved. Because of their construction, these instruments are relatively expensive to manufacture and therefore often intended to be relatively permanent and reusable.

Use of a relatively low pressure gas is advantageous to enable a stapler to be made of lighter construction and less expensive materials. This is desirable to lower the cost and make the stapler economically disposable. The stapler must, however, be capable of generating the substantial forces required to form the staples. Typically, the staples are metal wire which is partially formed prior to use and which must be further formed (e.g., crimped against an anvil) by the stapler. To generate the relatively large forces required to form the staples with low pressure gas would ordinarily require a relatively large pneumatic actuator. This is undesirable because a large actuator makes the stapler bulky and difficult to work with. In addition, a large actuator unnecessarily consumes a large amount of gas during the portion of actuator motion when relatively large forces are not required, i.e., during the first part of the actuator stroke when the staple is merely being advanced to the staple forming position. The gas which is thus effectively wasted substantially reduces the number of stapling operations which can be performed by the stapler before its gas supply is exhausted. This substantially shortens the useful life of the stapler if the gas supply is not replaceable, and even if the gas supply is replaceable, it undesirably increases the frequency with which the gas supply must be replaced.

Although it may be desirable to perform functions of the stapling apparatus automatically using the self-powering elements in the apparatus, it may also be desirable for the initial function to be at least partly manual. For example, if the initial function is tissue clamping, it may be preferable to initiate such function manually so that it can be performed slowly and precisely and the results inspected and corrected if necessary before the automatic self-powered portion of the operating sequence begins. See, for example, U.S. Pat. Nos. 4,349,028 and 4,331,277 to Green.

Many of the instruments described above are limited in their range of operability. Improvements have been made in the art of surgical instruments to increase their range of operability. For example Nierman (U.S. Pat. No. 4,880,015) discloses a biopsy forceps designed for use through a flexible fiberoptic bronchoscope. The biopsy forceps includes a handle connected to a thin elongated flexible shaft with a distal portion thereof hinged to the shaft. A grasping tool or biopsy forceps is attached to the distal hinged portion. Control wires extend from the handle through the distal to the shaft for controlling the angular rotation of the distal portion of the instrument.

In accordance with these and other principles, it is an object of the present invention to provide a self contained gas powered surgical instrument for driving surgical fasteners into body tissue which instrument has an increased range of operability.

It is another object of the present invention to provide a self contained gas powered surgical apparatus insertable through a small incision or narrow robe for driving surgical fasteners into body tissue and cutting the body tissue between rows of staples.

It is still another object of the present invention is to provide a self contained gas powered surgical apparatus which is disposable after use.

Another object of the present invention is to provide a self contained gas powered surgical apparatus having a mechanism which will prevent clamping of tissue unless the cartridge has been properly inserted in the instrument.

Yet another object of the present invention is to provide a self contained gas powered surgical apparatus having sealing structure for inhibiting the escape of insufflation gas through the apparatus.

Another object of the present invention is to provide a self contained gas powered surgical apparatus having counter structure for displaying the number of times the instrument has been fired.

A further object of the present invention is to provide a self contained gas powered surgical apparatus with structure to disable the apparatus after a predetermined number of firings have occurred.

Another object of the present invention is to provide a surgical apparatus that provides a full range of remotely actuated movements to the distal working members of the apparatus to facilitate interaction with and manipulation of tissue.

Yet another object of the present invention is to provide a self contained gas powered surgical apparatus having a pistol-type handle assembly.

Another object of the present invention is to provide a self contained gas powered apparatus having a pneumatic actuation system including a movable valve member configured to interact with a stationary gas supply canister.

SUMMARY OF THE INVENTION

The objects of the invention are accomplished by providing a self contained endoscopic surgical instrument which is at least partially operable by means of a relatively low pressure pneumatic assembly. The surgical instrument in accordance with an embodiment of the present invention is a surgical stapling apparatus which is adapted for placing one or more longitudinal rows of staples. This apparatus may further include a knife for making an incision in body tissue between the rows of staples. The latter configuration may find particular use in adjoining two hollow organs or in removing an organ, such as the appendix, the gallbladder, etc.

In a preferred embodiment of the subject invention the endoscopic stapler comprises a frame portion, an elongated tubular body portion extending from the frame portion and adapted for receiving an articulating cartridge assembly. The articulating cartridge assembly includes a cartridge mounting portion removably maintained in a distal end portion of the tubular body portion and a cartridge housing portion which is pivotally connected to the cartridge mounting portion. A cable loop assembly is associated with the tubular body portion of the instrument for effectuating the articulation of the cartridge housing portion relative to the cartridge mounting portion of the cartridge assembly. The cable loop assembly includes a cable member, a pivot block member mounted for rotation in a distal end portion on the tubular body portion about an axis perpendicular to the longitudinal axis thereof, and a rotation control member operatively associated with the tubular body portion of the apparatus for manipulating the cable loop assembly. A cartridge element, which includes a plurality of surgical staples slidably mounted therein, and having a tissue engaging surface, is receivable within the cartridge housing portion of the cartridge assembly. An anvil member is also provided which has a staple forming surface formed thereon and which is mounted adjacent the cartridge housing portion of the cartridge assembly such that the anvil member is movable between an open position and a closed position wherein the staple forming surface is in close cooperative alignment with the tissue engaging surface of the cartridge element.

The apparatus further comprises means associated with the tubular body portion for moving the anvil member between the open and the closed positions, and means for ejecting the surgical staples from the cartridge element in such a manner so as to cause the staples to engage and form on the staple forming surface of the anvil member. The means for moving the anvil member comprises a linkage mechanism associated with the frame portion and extending into the tubular body portion to a cable mechanism. The cable mechanism includes a cable member mounted at a leading end thereof to the linkage mechanism and at a trailing end thereof to the cartridge housing portion of the cartridge assembly. The anvil member is operatively associated with the cable member intermediate the ends thereof. The means for ejecting the surgical fasteners comprises a plurality of pusher elements in abutment with the surgical fasteners, and at least one cam bar for actuating the pusher elements. The cam bar is mounted in an adapter which translates within the cartridge assembly. In one embodiment of the cartridge assembly, the cam bar is fixedly mounted in the adapter while in another embodiment the cam bar is freely movable within the adapter. The articulating cartridge assembly of the subject invention is also provided with bearing means for guiding the translation of the cam bars as they traverse the cartridge assembly at such times when the cartridge housing portion of the cartridge assembly is articulated relative to the cartridge mounting portion thereof.

The surgical apparatus of the subject invention includes a self contained pneumatic system which is disposed in the frame portion of the instrument and which includes a supply canister of relatively low pressure gas and a valve member.

The system is operatively connected to a pneumatic actuator mechanism which actuates the means for ejecting the surgical fasteners from the cartridge element. To expel gas from the canister, the system may be configured to accommodate either the movement of the canister relative to a fixed valve member or, the movement of the valve member relative to a fixed canister.

In another preferred embodiment of the surgical apparatus of the subject invention, the instrument includes a fastener applying assembly having an articulated base portion and fastener applying means which include a cartridge housing configured to retain a replaceable fastener cartridge and an anvil member against which fasteners are driven when ejected from the cartridge. Means are provided for effectuating the articulation of the fastener applying assembly between a first position generally in alignment with the longitudinal axis of the elongated body of the instrument and a second position angularly disposed with respect to the longitudinal axis of the elongated body. Means are provided for effectuating rotation of the fastener applying assembly about the longitudinal axis defined by the elongated body relative to the frame portion. Means are also provided for effectuating the independent rotation of the fastener applying means relative to the base portion of the fastener applying assembly to further increase the range of operability of the surgical apparatus of the subject invention. In a preferred embodiment of the subject invention, the fastener ejection means includes a camming sled which is movable through the staple cartridge from a distal end portion thereof toward a proximal end portion thereof. The camming sled is configured to interengage with the pneumatic actuator mechanism of the subject invention to effect the sequential ejection of fasteners from the cartridge.

In a preferred embodiment of the surgical apparatus of the subject invention, a counter mechanism is provided for indicating to a user the number of times the instrument has been operated or, alternatively, the number of remaining firings available. The counter mechanism is preferably operatively associated with the pneumatic actuation assembly and is configured to advantageously disable the pneumatic actuation system after the instrument has been operated a predetermined number of times. This prevents the apparatus from being operated beyond the capacity of the gas supply.

The surgical apparatus of the subject invention may further comprise sealing means associated with the tubular body portion of the instrument for prohibiting the egress of insufflation gas therethrough during surgical procedures. The instrument may be constructed either as a reusable unit or as a single use, disposable unit or, alternatively may be formed with a reusable handle portion and replaceable body portions and/or staple carrying cartridges. The handle portion of the surgical instrument may have a palm grip configuration or a pistol grip configuration depending upon the needs of the surgeon.

The present invention advantageously permits surgeons to perform internal surgical procedures including stapling and/or cutting simply by manually clamping the tissue to be manipulated and pneumatically actuating the fastener applying means. This results in greater convenience and ease of use of the instrument as well as more uniform actuation of the instrument mechanisms.

Further features of the invention, its nature, and various advantages will become more apparent from the accompanying drawings and the following detailed description of the invention.

BRIEF DESCRIPTION OF THE DRAWINGS

Preferred embodiments of the invention are described hereinbelow with reference to the drawings wherein:

FIG. 4 is a transverse view in cross section taken along line 4—4 of FIG. 3 oriented toward the proximal end of the instrument showing the frame and pneumatic assembly in the unclamped position;

FIG. 6 is a transverse view in cross section taken along line 6—6 of FIG. 5 oriented toward the proximal end of the instrument showing the frame and pneumatic assembly in the clamped and unfired position;

FIG. 7 is a top plan view in cross section taken along line 7—7 of FIG. 3 showing the frame and pneumatic assembly of the surgical instrument;

FIG. 10 a side cut away view in cross section showing the operation of the pneumatic assembly of the present invention as it is fired;

FIG. 12 is an exploded perspective view of another embodiment of the handle portion in accordance with the apparatus of FIG. 1;

FIG. 17 is a bottom plan view of the anvil member of the articulating cartridge assembly of FIG. 16;

FIG. 18 is a perspective view of the articulating cartridge assembly of the surgical instrument of FIG. 1;

FIG. 19 is a top plan view of the articulating cartridge assembly of FIG. 18 with the cartridge element removed therefrom;

FIG. 20 is an enlarged perspective view of the external portion of the cam bar adapter shown in FIG. 23;

FIG. 21 is an enlarged perspective view of the internal cam bar maintaining element of the cam bar adapter shown in FIG. 23;

FIG. 23 is a top plan view of the cartridge assembly of the FIG. 18 showing an adapter for freely maintaining the distal end portions of the cam bars;

FIG. 24 is a top plan view of the cartridge assembly of FIG. 18 showing an adapter for fixedly maintaining the distal end portions of the cam bars;

FIGS. 33-35 art top plan views of the cartridge assembly of the apparatus of FIG. 1 in an articulated option illustrating a complete firing sequence wherein:

FIG. 33 illustrates the prefiring position of the cam bar adapter;

FIG. 34 illustrates the cam bar adapter in the fully fired position;

FIG. 35 shows the return stroke of the cam bar adapter within the cartridge assembly;

FIG. 36 is an enlarged perspective view, partially cut-away, of another embodiment of the surgical instrument in accordance with the subject invention in a first articulated position;

FIG. 37 is a cross-sectional view taken along line 37—37 of FIG. 36;

FIG. 38 is an enlarged perspective view, partially cut-away, of the surgical instrument of FIG. 36 in a second articulated position;

FIG. 39 is a cross-sectional view taken along line 39—39 of FIG. 38;

FIG. 41 is a cross-sectional view taken along line 41—41 of FIG. 40;

FIG. 42 is a cross-sectional view taken along line 42—42 of FIG. 40;

FIG. 43 is a cross-sectional view taken along line 42—42 of FIG. 40, illustrating a first operational position of the mechanism of FIG. 40;

FIG. 44 is a cross-sectional view taken along line 42—42 of FIG. 40, illustrating a second operational position of the mechanism of FIG. 40;

FIG. 48 is a cross-sectional view taken along line 47—47 of FIG. 45, illustrating a first operational position of the mechanism of FIG. 45;

FIG. 49 is a cross-sectional view taken along line 47—47 of FIG. 45, illustrating a second operational position of the mechanism of FIG. 45;

FIG. 50 is an exploded perspective view of yet another embodiment of the actuation member associated with the mechanism for effectuating the articulation of the surgical instrument of FIG. 36;

FIG. 53 is a top plan view in partial cross-section of the surgical instrument of FIG. 52 with the distal end portion thereof in an articulated position relative to the elongated portion of the instrument;

FIG. 54 is a top plan view of the surgical instrument illustrated in FIG. 53 with the distal end portion thereof rotated about its own axis;

FIG. 58 is a side elevational view in cross-section of the fastener applying assembly of the surgical instrument of FIG. 52 in an open position;

FIG. 59 is a side elevational view in cross-section of the fastener applying assembly of the surgical instrument of FIG. 52 in a closed position;

FIG. 60 is a cross-sectional view of a planetary gear assembly taken along line 60—60 of FIG. 52;

FIG. 61 is a cross-sectional view of a planetary gear assembly taken along line 61—61 of FIG. 52;

FIG. 62 is a side elevational view in partial cross-section of the fastener cartridge removed from the base portion of fastener applying assembly of the surgical instrument of FIG. 52;

FIG. 63 is a top plan view in partial cross-section of the articulated joint at the distal end of the surgical instrument of FIG. 52;

FIG. 64 is a cross-sectional view of a planetary gear assembly taken along line 63—63 of FIG. 63;

FIG. 66a is a perspective view of another embodiment of the drive mechanism which defines a portion of the fastener applying assembly illustrated in FIG. 66;

FIG. 72 is a side elevational view in cross-section of the fastener applying assembly of the surgical apparatus illustrated in FIG. 65 with the cartridge assembly thereof disposed in a closed position;

FIG. 73 is a side elevational view in cross-section of the fastener applying assembly illustrated in FIG. 72 with the cam sled of FIG. 67 moved toward the proximal end portion of the cartridge as the apparatus is actuated;

FIG. 74 is a side elevational view in cross-section of the fastener applying assembly illustrated in FIG. 72 with the cam sled of FIG. 67 disposed adjacent the proximal end portion of the cartridge after the apparatus has been actuated;

FIGS. 78–80 are perspective, elevational, and cross-sectional views, respectively, of the latching link which defines a portion of the firing control linkage illustrated in FIG. 75;

FIGS 81–84 are perspective and elevational views, respectively, of the rocker link which defines a portion of the firing control linkage illustrated in FIG. 75;

FIGS. 86a and 86b are side elevational views in cross-section of another approximation shaft constructed in accordance with a preferred embodiment of the subject invention which includes a tensioning screw;

FIG. 87 is a side elevational view in cross-section of the body of the surgical apparatus of FIG. 65 illustrating the articulation control mechanism and the control mechanism for effecting the independent rotation of the fastener applying assembly and depicting the fastener applying assembly disposed in an articulated and rotated position;

FIG. 87a is an enlarged plan view in cross-section of the transition area between the body and the fastener applying assembly illustrating a rotation transmission mechanism;

FIG. 91 is a side elevational view in partial cross-section of the handle assembly of the surgical apparatus illustrated in FIG. 90 with the approximation handle thereof disposed in a neutral position prior to operation of the apparatus;

FIG. 94 s a side elevational view in partial cross-section of the handle assembly illustrated in FIG. 91 with the approximation handle thereof disposed in a compressed position and the pneumatic actuation system thereof actuated to drive the piston through the compression chamber;

FIG. 95 is a side elevational view in partial cross-section of a portion of the handle assembly illustrated in FIG. 91 with the piston disposed adjacent the proximal end of the compression chamber to disengage the firing control linkage;

FIG. 95a is a localized elevational view in partial cross-section of the counter mechanism of the gas powered surgical apparatus of the subject invention;

DETAILED DESCRIPTION OF THE PREFERRED EMBODIMENTS

Figure 1:
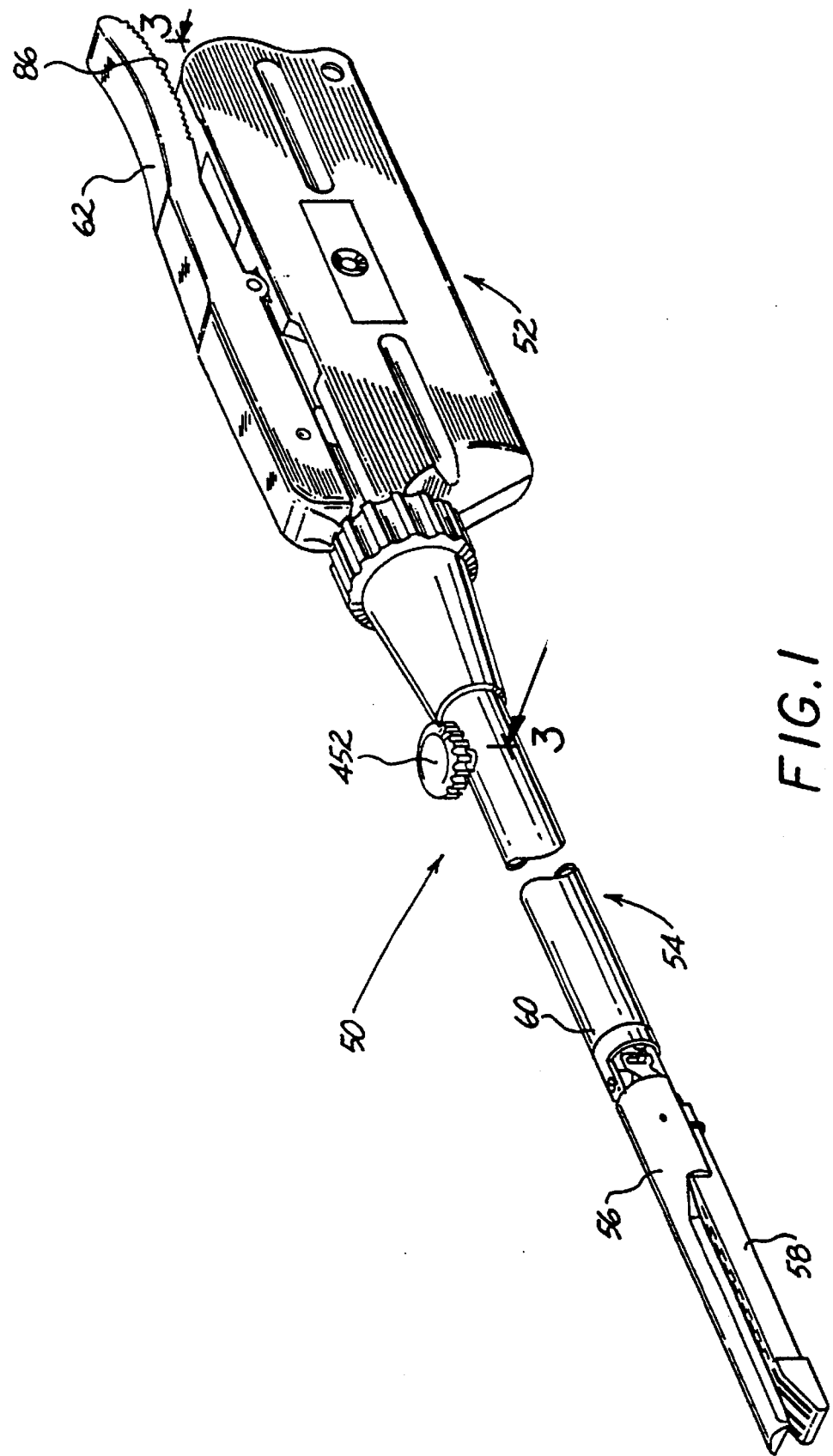
FIG. 1 is a perspective view of a self contained gas powered endoscopic surgical instrument in accordance with the present invention.

It is generally accepted that endoscopic procedures are more common than laparoscopic procedures. Accordingly, the present invention shall be discussed in terms of endoscopic procedures and apparatus. However, use herein of terms such as "endoscopic", "endoscopically" and "endoscopic portion", among others, should not be construed to limit the present invention to a stapling and cutting apparatus for use only in conjunction with an endoscopic tube. On the contrary, it is believed that the present invention may find use in any procedure where access is limited to a small incision, including but not limited to laparoscopic procedures. Also, as used herein the terms "fasteners" and "staples" shall be treated equivalently. Unless otherwise stated, the term "cartridge assembly" shall include at least the cartridge itself and staples or fasteners and staple drive members disposed therein.

In the drawings and the description which follows, as is customary, the term "proximal" refers to the end which is closest to the operator while the term "distal" will refer to the end which is furthest from the operator.

Figure 5:
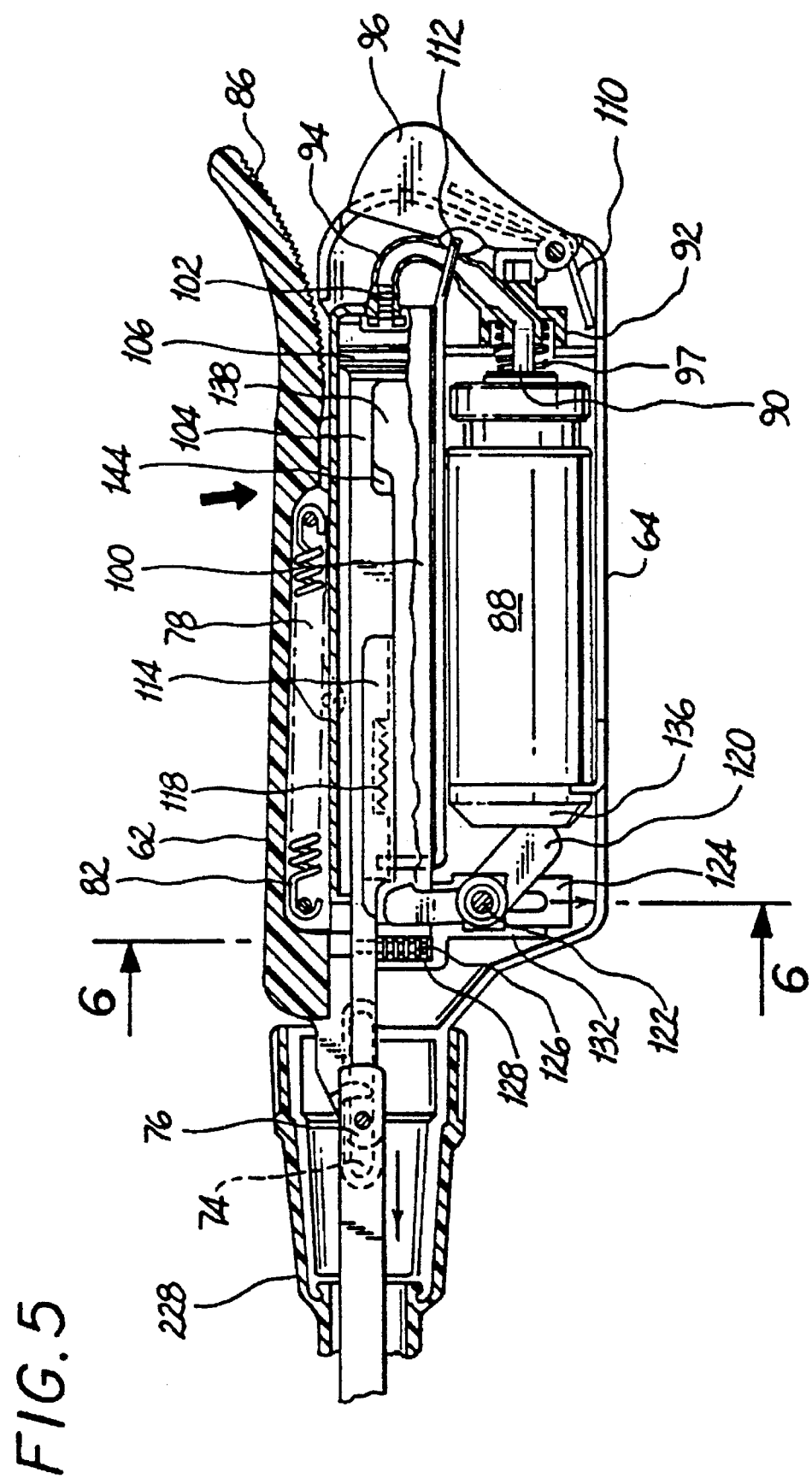
FIG. 5 is a side plan view in cross section showing the frame and pneumatic assembly in the clamped and unfired position.

Referring to FIG. 1, a self contained gas powered endoscopic surgical apparatus constructed in accordance with the principles of the present invention is illustrated and is designated generally by reference numeral 50. Surgical apparatus 50 essentially comprises a frame portion 52 and an elongated portion 54. An anvil member 56 and an articulating cartridge assembly 58 are preferably removably mounted in a distal end portion 60 of elongated portion 54. Anvil member 56 and cartridge assembly 58 are manually controlled by means of an articulating handle 62 associated with frame portion 52. More particularly, handle 62 interconnects with anvil member 56 by means of a linkage and cable assembly which is associated with the elongated portion 54 such that when handle 62 is articulated from an open position (see FIG. 3) to a closed position (see FIG. 5), anvil member 56 is moved into close approximation with the articulating cartridge assembly 58. This operation will be discussed in greater detail hereinbelow.

Figure 2:
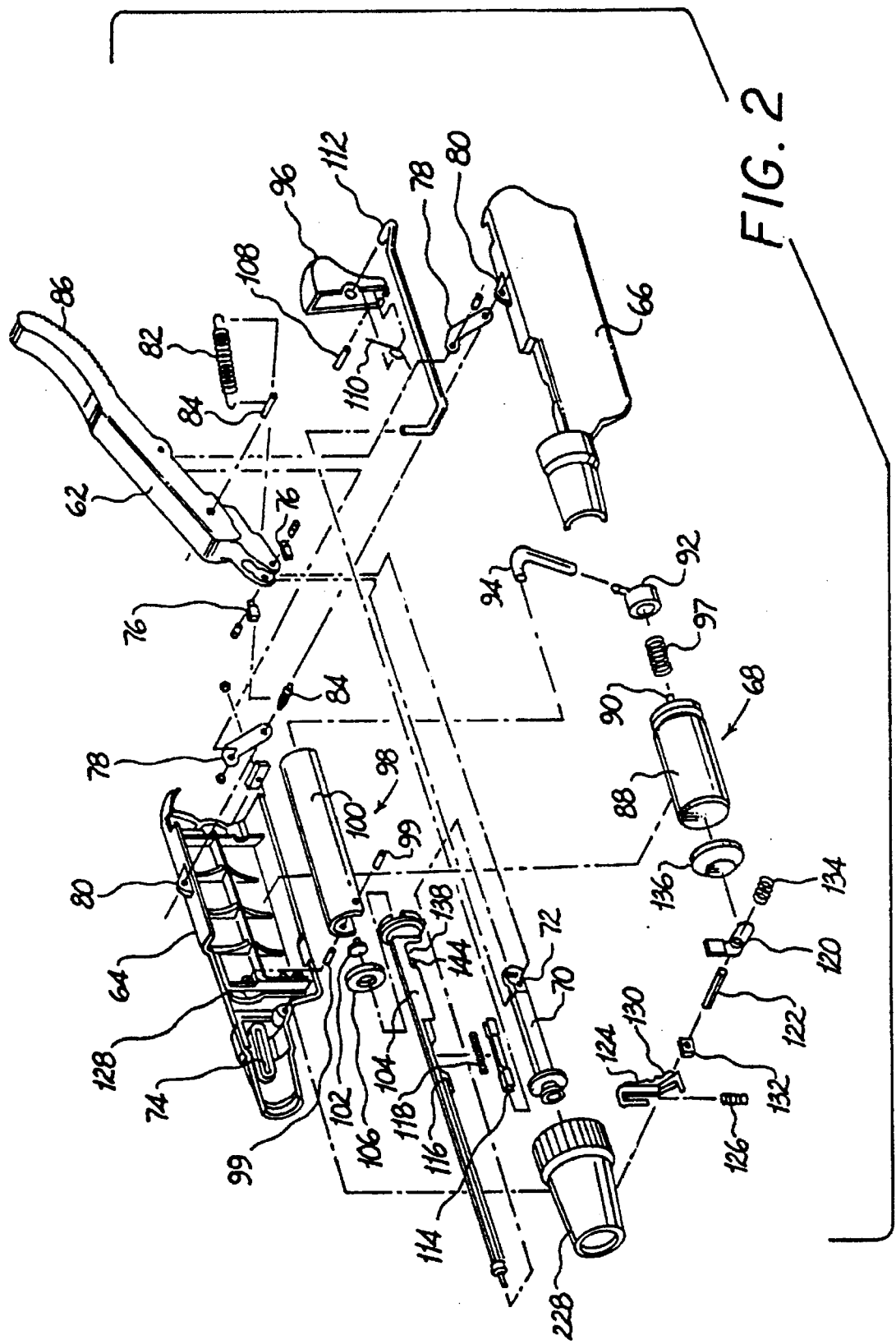
FIG. 2 is an exploded perspective view of the frame and pneumatic assembly of the surgical instrument of FIG. 1.

Turning now to FIG. 2, the frame portion 52 of surgical apparatus 50 includes opposed first and second housing members 64 and 66 which enclose a pneumatic system designated generally by reference numeral 68. The distal end portion of articulating handle member 62 is pivotally connected to a clamp tube 70 at a pivot point 72. Longitudinal grooves 74 are formed in the opposed first and second housing members 64 and 66 adjacent pivot point 72 for slidably receiving molded shuttles 76 which are attached to the articulating handle member 62 at pivot point 72. The molded shuttles 76 are pivotally connected to either side of the pivot point 72 on the distal end of handle 62 and function to guide the distal end thereof in a longitudinally distal direction as handle 62 is articulated.

A pair of articulating links 78 interconnect an intermediate portion of handle member 62 to a pair of projections 80 formed on an upper surface of housing members 64 and 66 respectively. A handle return spring 82 extends between handle 62 and housing members 64 and 66 by means of a pair of spring anchor pins 84, one of which is disposed in handle 62 and the other extending between projections 80. Anchor pins 84 also serve to pivotally connect articulating links 78 to projections 80. This spring 82 assists in returning handle 62 from its closed position to its open position.

The proximal end of articulating handle 62 is preferably diagonally formed away from housing members 64 and 66 so as to enable the surgeon to more easily release the handle 62 from its closed position. This is done by placing the hand under the proximal end of handle 62 and lifting. A texturized or serrated portion 86 may be advantageously formed on an under surface of the proximal end of handle 62 to enhance the gripping thereof.

Figure 11:
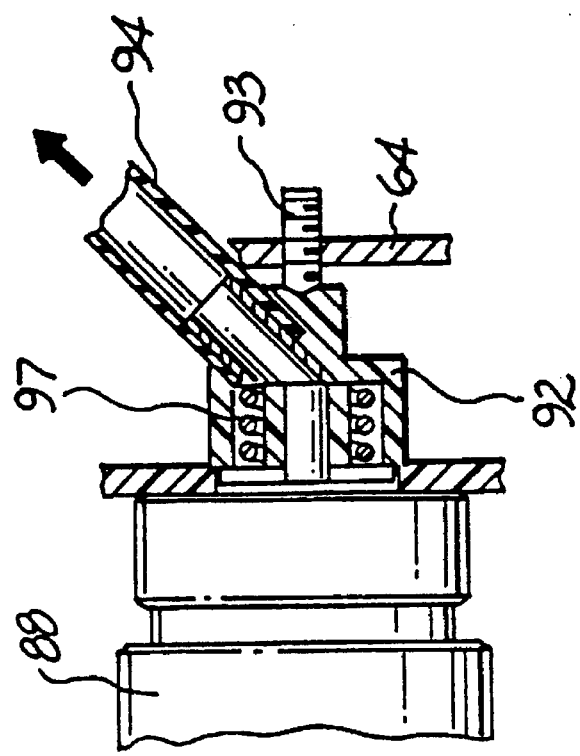
FIG. 11 is a side cut away view in cross section taken along line 11—11 of FIG. 10 showing the value and gas tube of the pneumatic assembly.
Figure 8:
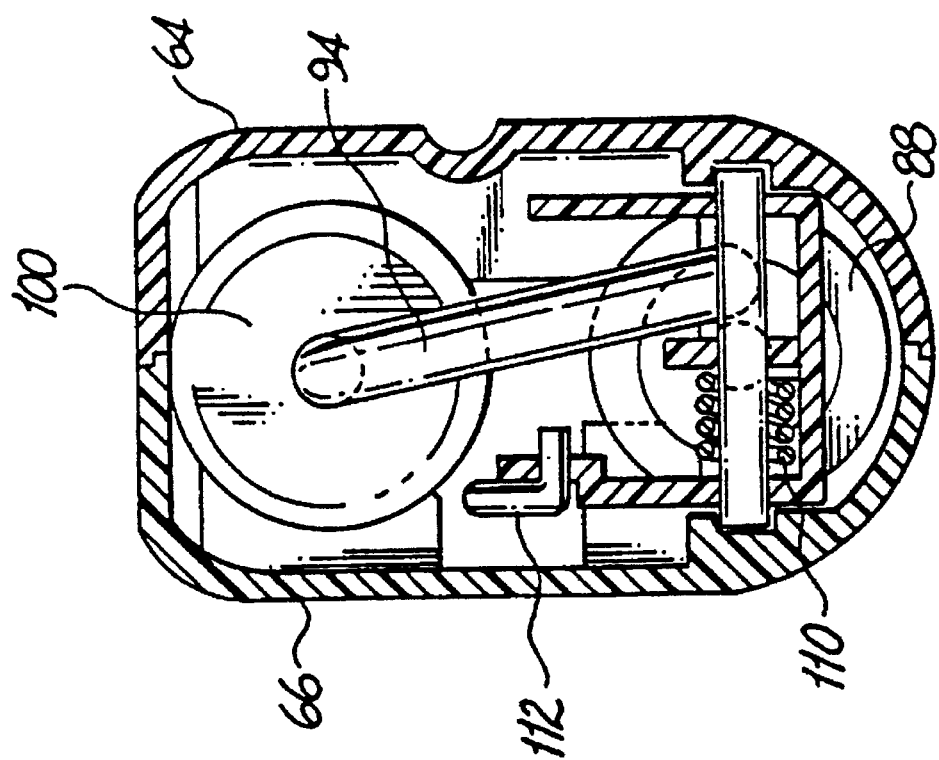
FIG. 8 is a transverse view in cross section taken along line 8—8 of FIG. 3 oriented toward the distal end of the instrument showing a portion of the frame and pneumatic assembly.
Figure 9:
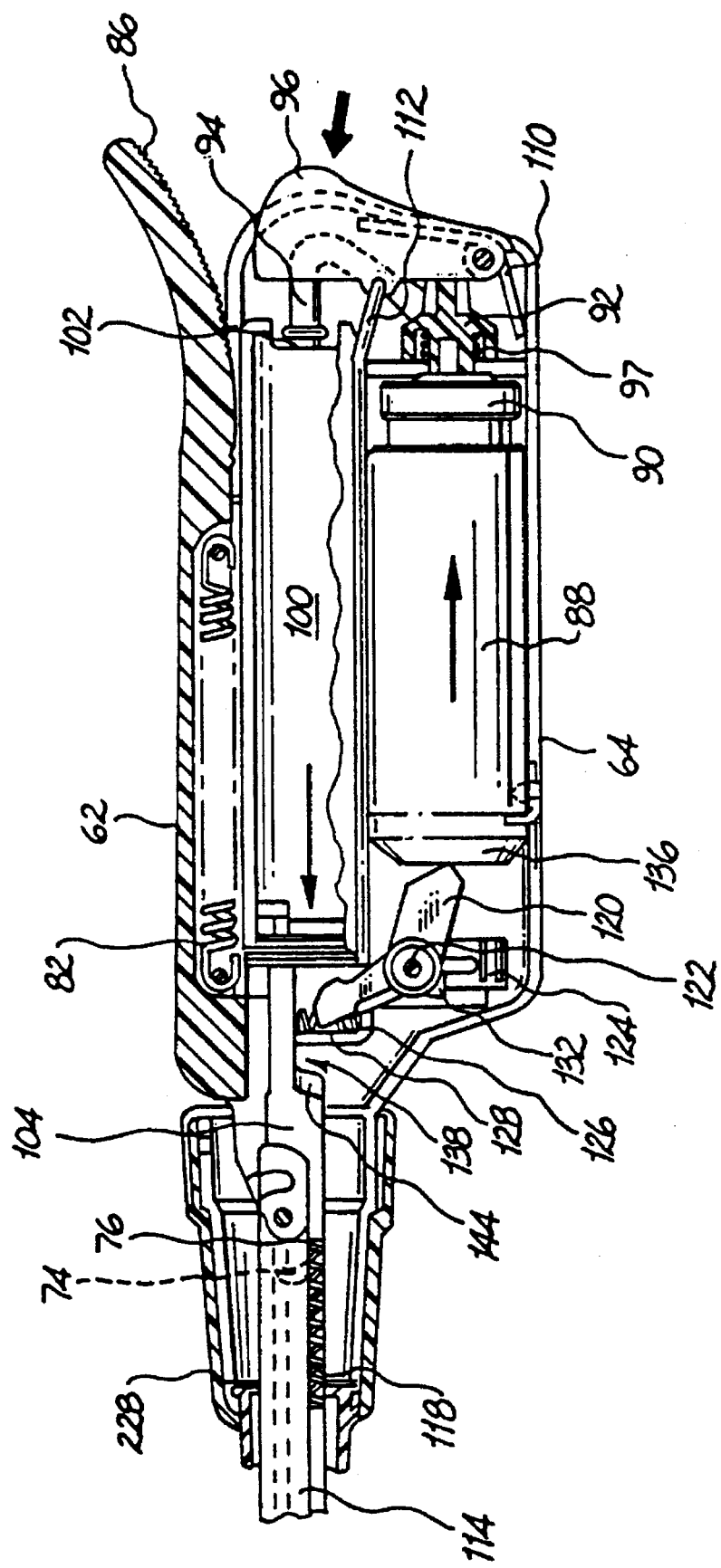
FIG. 9 is a side plan view in cross section showing the frame and pneumatic assembly of the present invention in the clamped and fired position.

Pneumatic system 68 is wholly contained within housing members 64 and 66 and includes a container 88 of relatively low pressure gas longitudinally slidably mounted therein. The pressure of the gas in container 88 during operation of the stapler is typically less than about 200 p.s.i.g. and preferably in the range from about 80 p.s.i.g. to about 160 p.s.i.g. Any suitable non-toxic gas can be used including but not limited to halogenated hydrocarbons which are gaseous at room temperature, e.g., fluorinated hydrocarbons such as Freon 12 or chlorinated hydrocarbons such as Freon 152A. Container 88 dispenses the relatively low pressure gas through stem 90, valve 92, and gas tube 94 when the firing trigger 96 is depressed. Spring 97 is positioned between container 88 and valve 92 and functions to hold the container 88 in a position spaced from valve 92. Valve 92 is fixed within housing members 64 and 66 and is longitudinally adjustable by means of set screw 93 (see FIG. 11). This feature permits the position of valve 92 to be longitudinally changed to compensate for manufacturers' variations in length among containers 88 between a distal end and the proximal end of stem 90. A pneumatic actuator 98 is disposed above container 88 within housing members 64 and 66. Actuator 98 includes a pneumatic cylinder 100 which is held in place by opposed pins 99. Cylinder 100 is substantially closed at the proximal end thereof but for a ferrule 102 extending therethrough and is open at its distal end, wherein a pneumatic piston 104 is mounted for reciprocal motion therein on an axis which is parallel to the longitudinal axis of elongated portion 54. Cylinder 100 is preferably circular in transverse cross-section, however, other configurations would function acceptably well.

Piston 104 is pneumatically sealed to cylinder 100 by an O-ring 106 molded of polyethylene or the like. Gas dispensed from container 88 is supplied to pneumatic actuator 98 via gas tube 94 which admits the gas to cylinder 100 through ferrule 102 behind piston 104 to drive piston 104 distally in the cylinder 100. The distal end of piston 104 is adapted to engage the firing mechanism of the surgical apparatus as will be described in greater detail below.

Referring to FIGS. 2–10, firing trigger 96 is pivotally mounted in a proximal end of housing members 64 and 66 by a pivot pin 108. A spring 110 is positioned adjacent pin 108 which serves to bias firing trigger 96 proximally into the prefiring position. A trigger rod 112 extends distally from firing trigger 96 in a longitudinal direction so as to engage a piston slide 114 which is positioned in a lower portion of piston 104. Piston slide 114 comprises a substantially U-shaped channel which fits into a corresponding groove 116 formed in piston 104. Piston slide 114 is spring loaded in a proximal direction by a spring 118 and includes a transverse projection 120 on a lower distal end thereof which engages the distal end of trigger rod 112.

Figure 3:
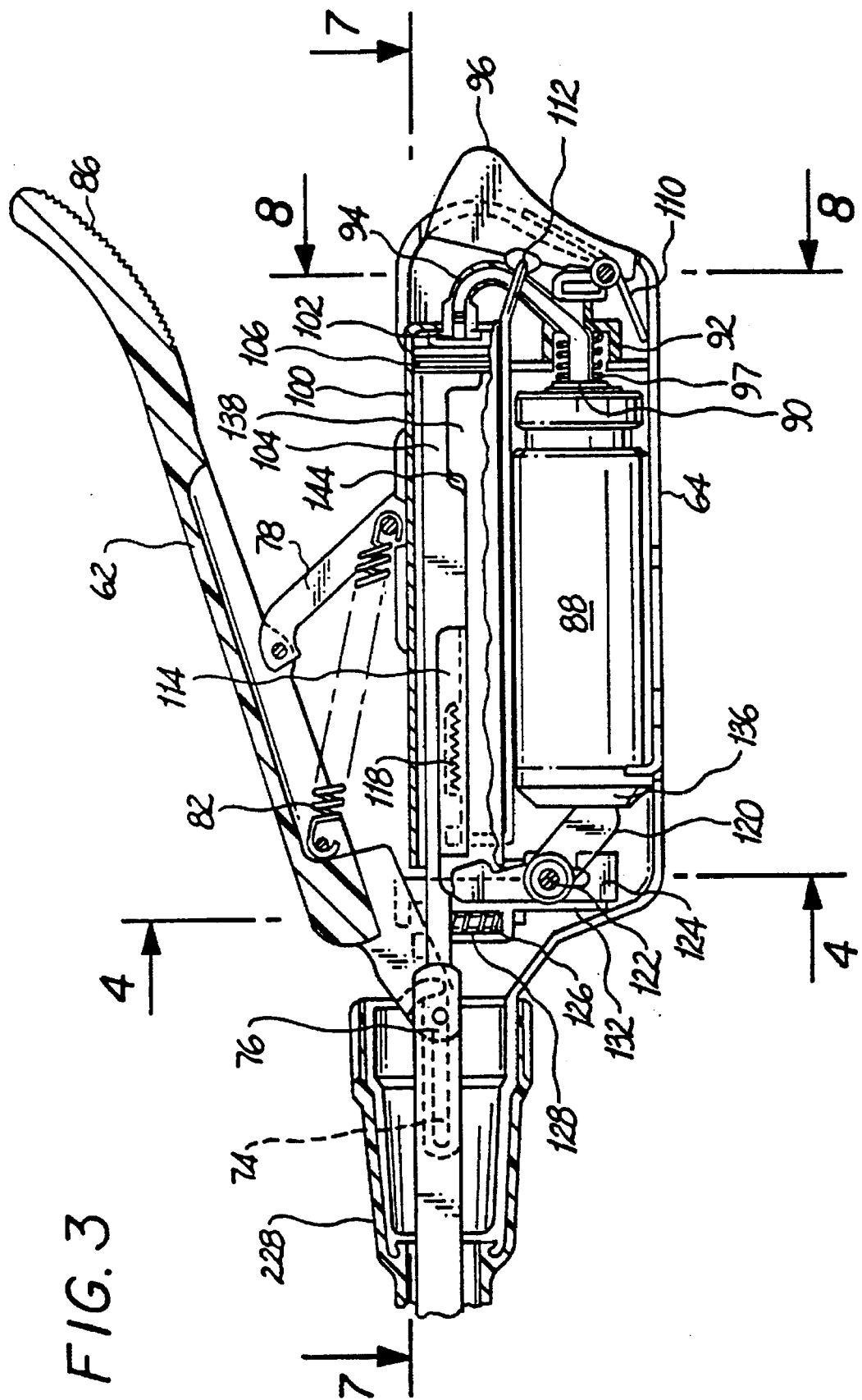
FIG. 3 is a side plan view in cross section taken along line 3—3 of FIG. 1 showing the frame and pneumatic assembly in the unclamped and unfired position.

A rocking lever 120 is pivotally mounted on a transverse slide pin 122 and is adapted for transverse movement relative to slide pin 122 between an engaged position prior to firing (see FIGS. 5–7) and a disengaged position when articulating handle 62 is open (see FIGS. 3 and 4). A cam slide 124 is vertically mounted in first housing member 64 for reciprocal movement between an upper position and lower position (see FIGS. 4 and 6, respectively). Cam slide 124 functions to move rocking lever 120 between the engaged position (FIG. 6) and the disengaged position (FIG. 4). Thus, until articulating handle member 62 is closed, causing cam slide 124 to move rocking lever 120 into the engaged position, surgical instrument 50 cannot be fired.

Cam slide 124 is normally biased in its upper disengaged position by a cam slide spring 126 which is mounted in vertical groove 128 formed in the first housing member 64 (see FIGS. 3 and 4). In this upper position, cam slide 124 extends upward beyond first housing member 64 to engage articulating handle member 62 as it is moved to a closed position (see FIGS. 5 and 6). Cam slide 124 further includes a camming surface 130 which contacts a corresponding camming surface of a camming block 132 which is mounted on slide pin 122. Camming block 132 is loaded against cam slide 124 by a slide spring 134 and moves rocking lever 120 transversely on slide pin 122 between an engaged position and a disengaged position. As articulating handle 62 is compressed toward housing members 64 and 66 in the direction of arrow 135 it contacts cam slide 124, moving it downward, and causing camming surface 130 to move camming block 132 and rocking lever 120 transversely into an engaged position in alignment with piston 104.

Turning to FIGS. 3, 5–7 and 9, once the articulating handle 62 has been fully compressed, rocking lever 120 is disposed in alignment with piston slide 114 and can be pivotally moved about transverse slide pin 122 to engage a pusher disk 136 disposed at the distal end of container 88. When the instrument is in the clamped configuration, depression of firing trigger 96 moves trigger rod 112 distally in the longitudinal direction causing piston slide 144 to engage and pivot rocking lever 120 which, in turn, engages pusher disk 136 and moves container 88 into contact with valve 92 to dispense gas and propel piston 104 in the distal direction (see FIGS. 9–11).

As piston 104 moves distally, rocking lever 120 remains in its pivoted firing position by contact with the bottom surface of piston 104. A gap 138 is formed in the bottom surface of piston 104 adjacent the proximal end thereof which effectively allows rocking lever 120 to disengage from piston 104 and return to a position wherein container 88 is released from engagement with valve 92, thereby stopping the flow of gas into pneumatic cylinder 100.

A pair of return springs 140 and 142 disposed in elongated portion 54 drive piston 104 back to its initial prefired position. A camming surface 144 is formed in a distal end of gap 138 which causes rocking lever 120 to move out of engagement with piston 104 as it returns and rocking lever 120 moves to its original prefired position (see FIG. 5).

Referring to FIG. 12, another embodiment of frame portion 52 is illustrated which includes annular rings 150 and 152 both of which are provided between the distal end of frame 52 and the proximal end of elongated portion 54. In addition to the reduction in egress of insufflation gas resulting from the close tolerances and interfitting of structural elements within frame portion 52 and/or elongated portion 54, these rings 150,152 further inhibit the escape of insufflation gas from the operative site. Additionally, rings 154 and 156 are positioned adjacent the proximal and distal ends, respectively, of clamp tube 70 to effectively seal off insufflation gas from the area of piston 104.

This embodiment of frame portion 52 further comprises a counter mechanism including a counter ratchet 160 attached to trigger rod 112, and a leaf spring 162 which is mounted in housing 66 so as to engage teeth formed on the bottom surface of counter ratchet 160. Numerical indicators are disposed in longitudinal spaced apart relationship on an outer surface of the counter ratchet 160 and correspond to the number of times apparatus 50 has been fired. An access plate 164 having a viewing window 166 therein is positioned in the outside surface of housing member 66 to facilitate observation of the counter mechanism.

In operation, each time the instrument is fired the leaf spring 162 engages a respective proximally located tooth of the counter ratchet 160, effectively sliding the counter ratchet 160 distally to align the next lower number in viewing window 166. The counter mechanism of this embodiment further includes a locking feature whereby the trigger button 96 is retained in the firm position when the leaf spring 162 engages the most proximal surface of the counter ratchet 160 and prevents the firing rod 112 from returning to its proximal unfired position.

This embodiment of frame portion 52 further includes an integral trigger button rotary safety mechanism comprising a rotary safety shaft 168 disposed within a roller 170. The rotary safety mechanism is rotatably positioned in trigger button 96 with the roller 170 extending out beyond the plane of the back surface of trigger button 96. Projections 172 are eccentrically formed on both sides of rotary safety shaft 168 and extend out beyond the plane of the side surfaces of the trigger button 96. A spring 174 functions to bias the rotary safety mechanism such that projections 172 are disposed in their distalmost orientation.

Figure 13:
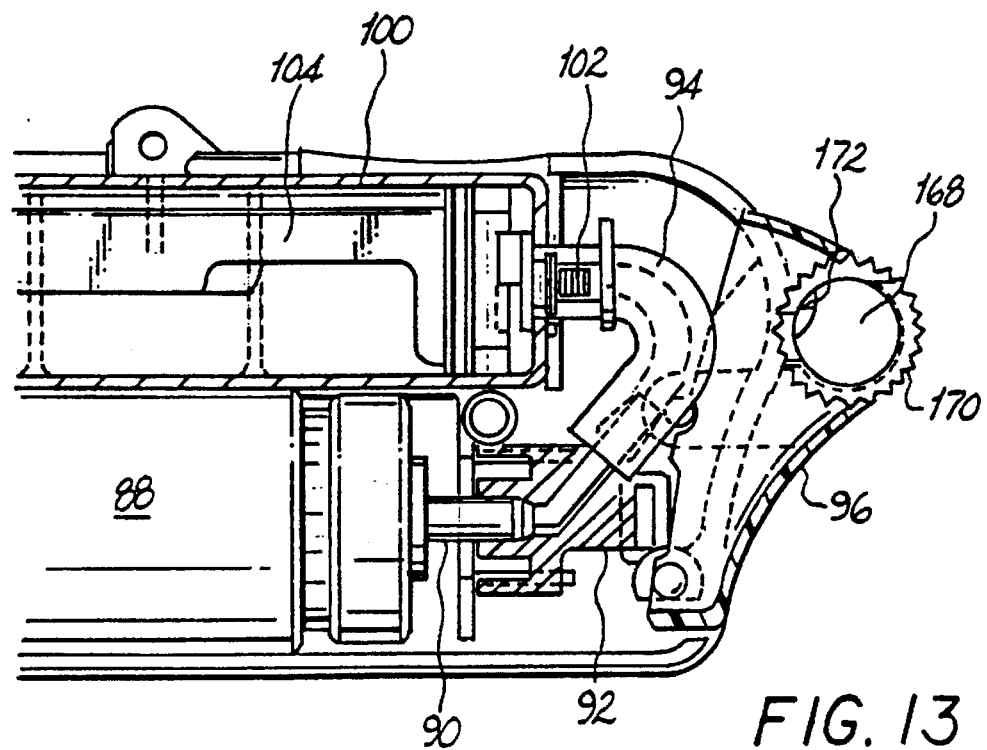
FIGS. 13 and 14 are side cross-sectional views of the firing trigger with integrated lockout structure in the unfired and fired positions respectively.
Figure 14:
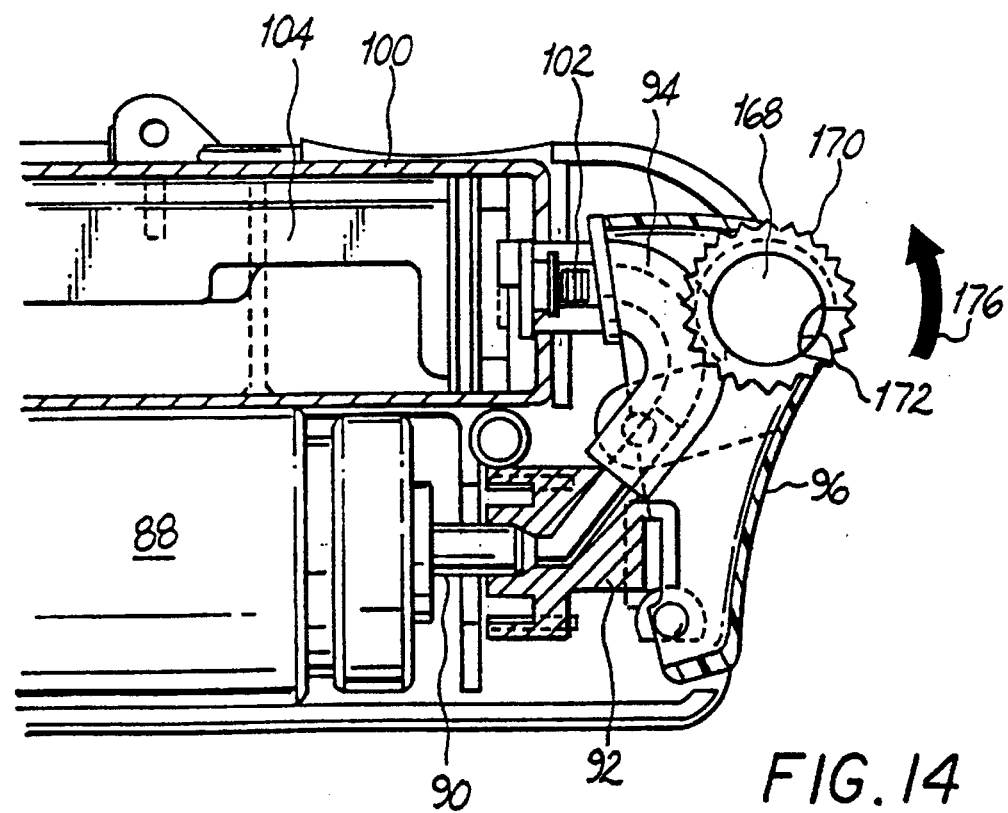

Referring now to FIGS. 13 and 14, in the instrument's unfired position projections 172 are in their distalmost position and are disposed in direct alignment with the proximal ends of the housing members 64 and 66. In this position, trigger button 96 cannot be accidentally depressed to fire the instrument In order to disengage the safety mechanism, the roller 170 is moved in the direction of arrow 176 so as to rotate projections 172 from their distalmost position to their proximal most position effectively allowing trigger button 96 to be depressed to fire the instrument. As soon as roller 170 is released, spring 174 returns the safety mechanism to its normal position so as to prevent subsequent accidental firings.

Figure 15:
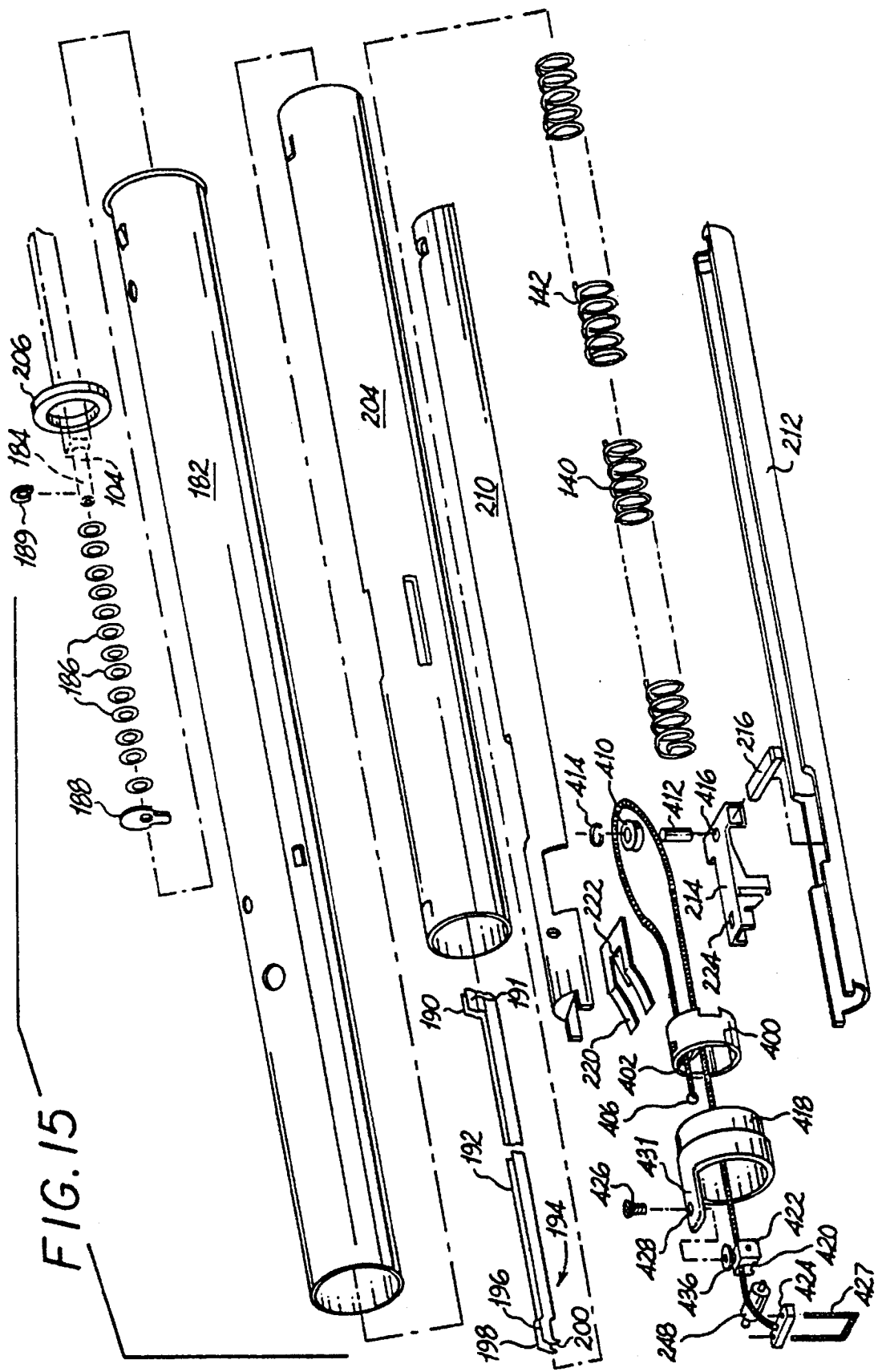
FIG. 15 is an exploded perspective view of the elongated portion of the surgical instrument of FIG. 1.

Turning to FIG. 15, the elongated portion 54 of surgical apparatus 50 is illustrated in exploded detail. At a proximal end of elongated portion 54, piston 104 extends through clamp tube 70 (FIG. 12) and into the proximal end of a cover tube 182. Piston 104 is adapted for reciprocal movement within clamp tube 70 in response to actuation of pneumatic system 68. The distal end of piston 104 is provided with an attachment flange 184 for mounting a plurality of pusher washers 186 of the type which are well suited for high loads in small spaces. A spring support washer 188 is positioned on flange 184 for engaging the proximal ends of inner and outer return springs 140 and 142. A lock washer 189 maintains the pusher washers 186 in a desired position on flange 184. Attachment flange 184 has a chamfered distal tip and is configured and dimensioned to be received between the proximal opposed fingers 190 and 191 of a channel member 192.

As shown in FIG. 15, channel member 192 is defined by an elongated structure which is slidably mounted in elongated portion 54 for reciprocal longitudinal motion therein. As mentioned above, channel 192 has opposed fingers 190 and 191 at a proximal end thereof to receive attachment flange 184 of piston 104. A forked portion 194 is provided at a distal end portion of channel 192 defining a slot 196 therebetween. Forked portion 194 has a pair of opposed ramping surfaces 198 and 200, the function of which will be described in greater detail below.

An extension sleeve 204 is disposed within cover tube 182 and is fixed on a proximal end thereof to clamp tube 70. A sealing member 206 is mounted adjacent clamp tube 70 for sealably isolating frame portion 52 of instrument 50 from elongated portion 54 thereof. Inner and outer return springs, 142 and 140 respectively, are contained within upper extension spacer 210 and lower extension spacer 212 which are, in turn, combined and fixed within the extension sleeve 204. Spring support washer 188 abuts the proximal ends of inner and outer return springs 142 and 140 and, when instrument 50 is fired, transits the energy of the compressed springs 142 and 140 to the piston 104, returning it to its prefired position.

A support structure 214 is also disposed within extension spacers 210 and 212 adjacent the distal end thereof which functions to releasably receive cartridge assemblies in instrument 50. Support structure 214 is retained in place within combined extension spacers 210, 212 by a transverse support key 216. A clamp lockout structure is incorporated into support structure 214 and upper extension spacer 210. The clamp lockout structure comprises a leaf spring 220 having a diagonally downwardly extending projection 222 attached thereto. A slot 224 is formed through the top surface of support structure 214 and is adapted to engage and receive projection 222 whenever the support structure is not longitudinally aligned. This clamp lockout structure is designed and configured to prevent the instrument jaws from closing on tissue unless the cartridge and/or jaw elements are properly emplaced within the elongated portion 54 of apparatus 50.

Figure 16:
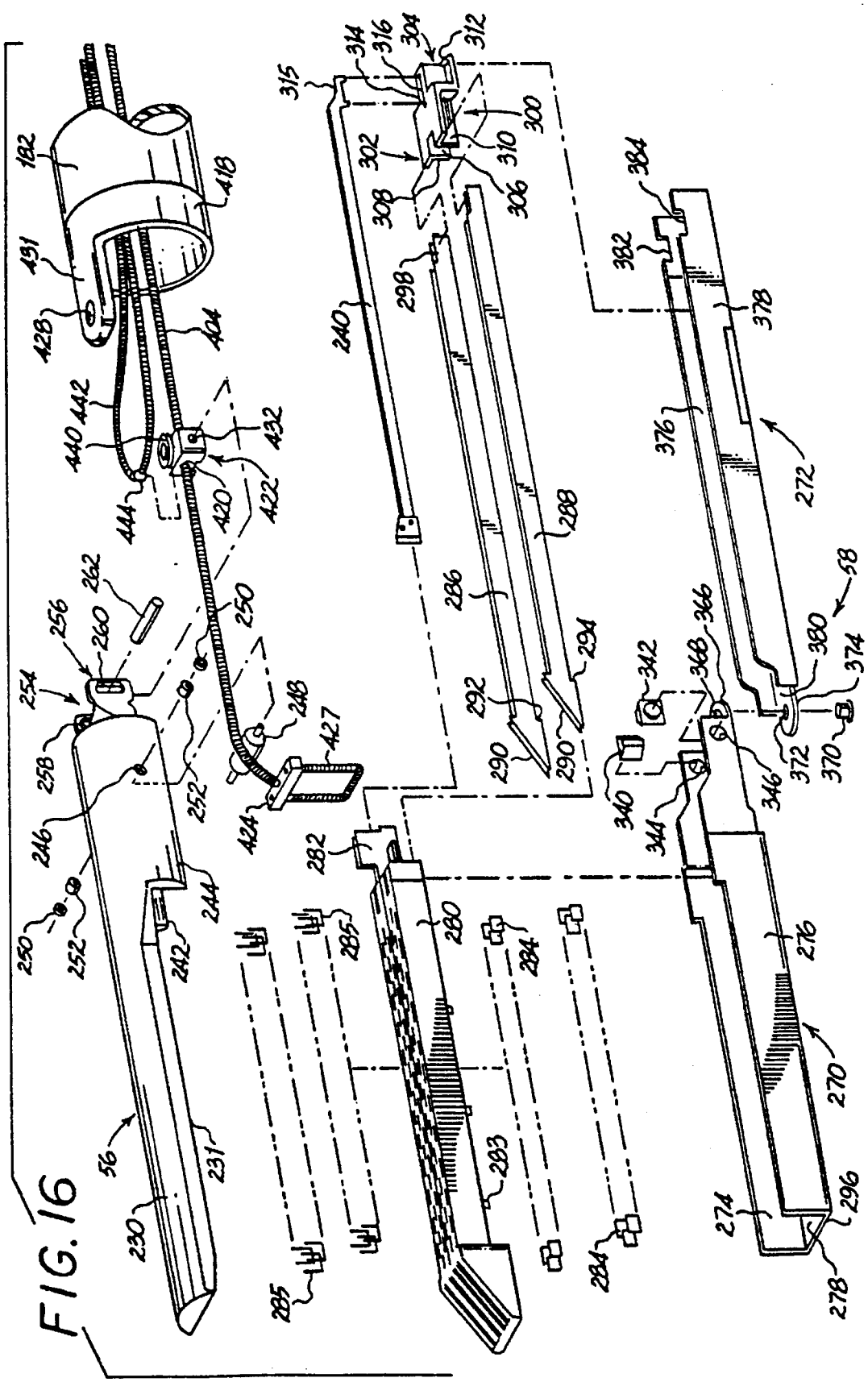
FIG. 16 is an exploded perspective view of the articulating cartridge assembly of the surgical instrument of FIG. 1.

Referring now to FIG. 16 and 17, anvil member 56 of surgical apparatus 50 comprises an elongated distal body portion 230 and a proximal mounting shroud 232. Body portion 230 defines a staple forming plate 234 (see FIG. 17) having a plurality of staple forming depressions 236 provided therein into which staples are driven so as to be formed. A longitudinal center groove 238 is also provided in staple forming plate 234 to facilitate the guided passage of a surgical knife 240 during a firing sequence of apparatus 50. Mounting shroud portion 232 is defined by opposed side walls 242 and 244 which are dimensioned to fit cooperatively upon a portion of cartridge assembly 58. Apertures 246 are included in the opposed side walls 242 and 244 for mounting a cylindrical pulley 248. Pulley 248 is maintained within shroud portion 232 by opposed fastener ring pairs 250 and 252 and functions in cooperation with a mechanism for moving anvil member 56 between an open position and a closed position. A pair of opposed spaced apart arms 254 and 256 extend longitudinally from the proximal end of shroud portion 232 and have vertical mounting slots 258 and 260 provided therein, respectively, for receiving a mounting pin 262. Mounting slots 256 and 258 enable anvil member 56 to adjust its position upon engaging tissue against forming plate 234. More particularly, slots 256 and 258 permit adjustment of the spacing between forming plate 234 and cartridge assembly 58.

The articulating cartridge assembly 58 of the subject invention comprises a forward housing portion 270 and a rearward housing portion 272. Forward housing 270 is defined by a channel structure of substantially rectangular cross-section having opposed side walls 274 and 276 and a bottom wall 278. This channel structure constitutes the cartridge receiving portion and is dimensioned to receive a cartridge 280. A longitudinal groove structure 282 is defined in cartridge 280 for receiving and guiding knife 240 therethrough. A plurality of stems 283 extend downwardly from the undersurface of cartridge 280 for engagement in a plurality of corresponding apertures 287 formed in the bottom wall 278 of forward housing 270. A plurality of pusher elements 284 are disposed in cartridge 280 in abutment with a plurality of corresponding staples 285. The staples 285 are advantageously arranged in six longitudinal rows with three rows positioned on either side of groove structure 282. See, U.S. Pat. No. 4,978,049 to Green, the disclosure of which is incorporated herein by reference. In addition, two pairs of longitudinal slots are formed in the cartridge housing 280 and are adapted to receive a pair of dual cam bars 286 and 288 therein. Cam bars 286 and 288 each serve to drive three corresponding longitudinal rows of staples 285.

Cam bars 286 and 288 are each provided with a cam surface 290 in an upper distal end thereof and an overhanging ledge 292 with vertical surface 294 in a lower distal end. This overhanging ledge 292 is dimensioned to extend into the longitudinal slots formed in cartridge 280 to a point wherein the vertical surface 294 of overhanging ledge 292 drops down and abuts the forward edge 296 of the forward housing portion 270 cartridge assembly 58 when cam bars 286 and 288 move to their distal fired position. At their proximal ends, cam bars 286 and 288 are provided with hook structure 298 for releasably engaging a cam bar adapter 300.

Referring now to FIGS. 16, 19, and 23, one embodiment of cam bar adapter 300 in accordance with the present invention is illustrated. Cam bar adapter 300 comprises a forward section 302 and a rearward section 304. Forward section 302 is substantially rectangular in configuration and has a central longitudinal groove 306 formed therein and dimensioned to receive the longitudinal groove structure 282 on cartridge 280 when cam bar adapter 300 is urged to its forwardmost position. Flanges 308 and shelves 310 function to removably retain the proximal ends of cam bars 286 and 288. The rearward section 304 of cam bar adapter 300 is rectangular in configuration with projections 312 formed in the proximal end thereof. The rearward section is dimensioned to be receivable within the slot formed in forked portion 194 in channel member 192. Projections 312 are dimensioned to engage ramping surface 198 so as to allow forked portion 194 to ride up and over projections 312 when it is moved in the distal direction. A vertical bore 314 and a longitudinal groove 316 are formed in the rearward section 304 of cam bar adapter 300 which retain and hold the shank portion 315 of knife 240.

Figure 22:
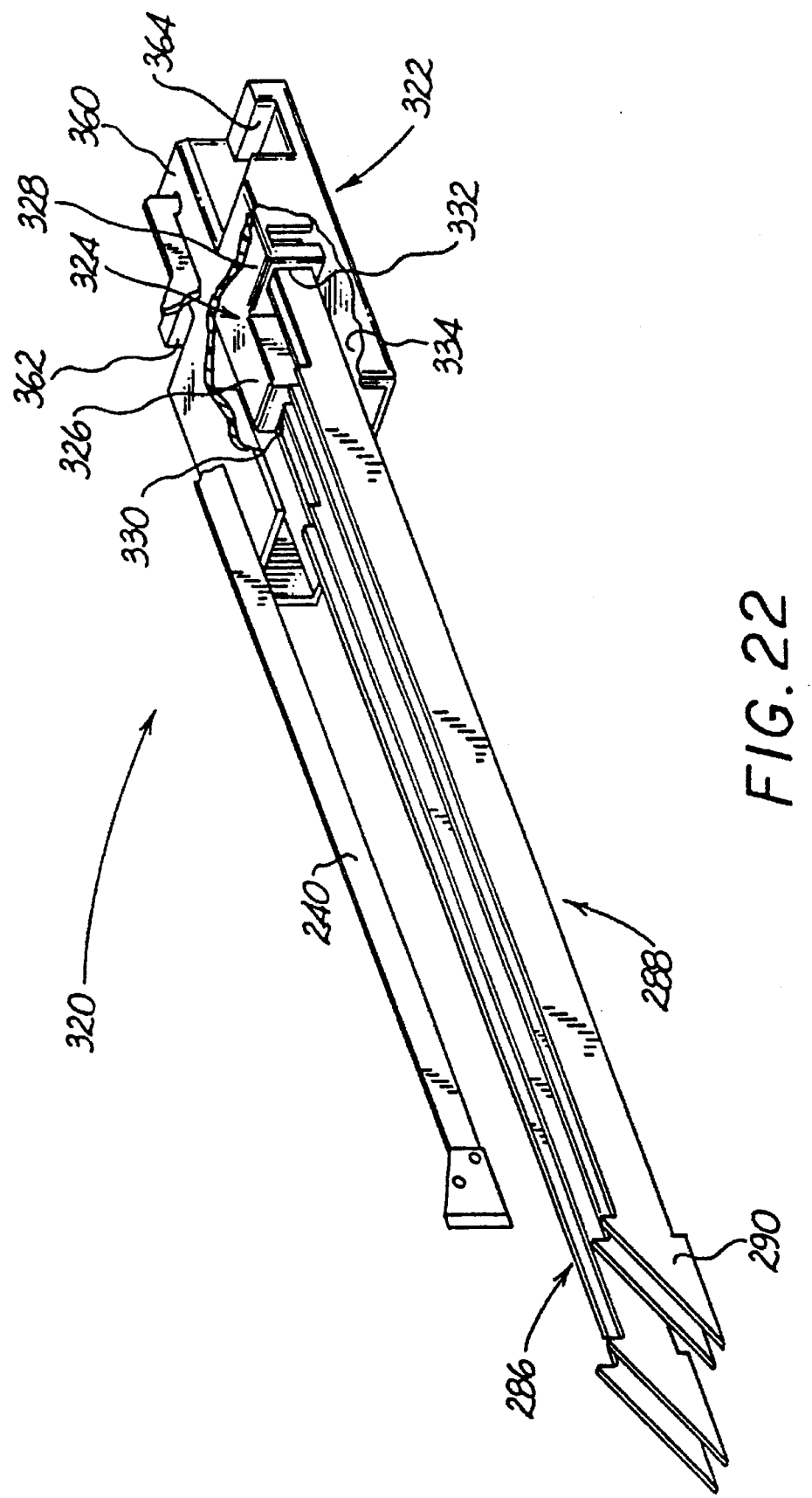
FIG. 22 is an enlarged perspective view, partially cutaway, of the cam bar adapter of FIGS. 20 and 21.

Although cam bar adapter 300 is effective to maintain cam bars 286 and 288 and to transport the same through cartridge assembly 58, it may be desirable to provide a cam bar adapter which enables the proximal ends of cam bars 286 and 288 to move freely in a transverse direction while being effectively maintained in a desired longitudinal position. Free mounting of the cam bars provides several advantages over fixed mounting which advantages will be discussed in detail hereinbelow. FIGS. 20–22 illustrate this embodiment of the cam bar adapter and is designated generally by reference numeral 320. Cam bar adapter 320 comprises a cam bar support fixture 322 and a housing structure 324. Support fixture 322 is defined by a substantially L-shaped structure having an elongated leg portion 326 and a transverse leg portion 328. A slot 330 is provided in leg portion 326 for receiving the proximal end of dual cam bar 286 and a similar slot 322 is provided in leg portion 328 for receiving the proximal end of dual cam bar 288. The staggered mounting of cam bars 286 and 288 in L-shaped support structure 322 advantageously positions cam bars 286 and 288 to more effectively eject the staples from cartridge 285. Support fixture 322 is dimensioned so as to fit within a rectangular channel 334 defined within housing structure 324. Channel 334 accommodates support fixture 302 in such a manner so that it can move freely therein.

The advantages of freely mounting cam bars 286 and 288 are best explained with reference to FIGS. 23 and 24. Cam bar adapter 300 is illustrated in FIG. 24, wherein the respective proximal portions of cam bars 286 and 288 are fixedly mounted. Upon articulating the forward housing 270 of cartridge assembly 58, cam bars 286 and 288 are compressed by opposed bearing members 340 and 342 disposed in forward housing 270. The compression of the cam bars 286 and 288 causes a buckling effect at the central spans thereof. The deflection is accentuated because the proximal end portions of cam bars 286 and 288 are fixed in cam bar adapter 300. In contrast, if cam bars 286 and 288 are mounted in cam bar adapter 320 such that the respective proximal end portions thereof are maintained in the L-shaped support fixture 322 which moves freely within channel 334 defined in housing structure 324, the degree of deflection or buckling across the central spans of cam bars 286 and 288 is substantially decreased. By reducing the degree of deflection across the spans of cam bars 286 and 288, the amount of force needed to drive cam bars 286 and 288 is also decreased. Moreover, the amount of pressure required to be released by the pneumatic system for driving cam bars 286 and 288 through a complete stroke will be less when the respective proximal end portions of cam bars 286 and 288 are mounted freely rather than fixedly in a cam bar adapter.

The cam bars are often made of stainless steel, however, it has been found that forming the cam bars from a shape memory alloy comprising, for example, a composition of nickel and titanium (such a composition is available from Raychem Corp., Menlo Park, Calif. under the Wade name TINEL), rather than stainless steel, will reduce the amount of force required to drive cam bars 286 and 288 through a firing sequence.

Referring to FIGS. 18, 19, 23, and 24, bearings 340 and 342 are mounted in a pair of opposed ports 344 and 346 provided in the opposed side walls 274 and 276 respectively, adjacent the proximal end of forward housing 270. Bearing members 340 and 342 have a truncated triangular configuration defining a planar bearing surface for guiding cam bars 286 and 288 as they traverse cartridge assembly 58 at such times when it is in an articulated position and, in addition, compress the cam bars as they travel into cartridge 280 as discussed above.

Referring again to FIGS. 20–22, housing structure 324 of cam bar adapter 320 is further provided with a pair of spaced apart apertures 350 and 352 for retaining a pair of corresponding prongs 354 and 356 formed on the shank 358 of knife 240. The rearward section 360 of housing structure 324 is of rectangular configuration and defines a structure for engaging groove 196 in channel member 192. Seats 362 and 364 are provided on either side of rearward section 360 for engaging the forked portion 194 of channel member 192.

Referring again to FIGS. 16, 18 and 19, a flange 366 extends outwardly from the proximal end of the bottom wall 278 of forward housing 270 and includes an aperture 368 for receiving a rivet 370. Rivet 370 also extends through an aperture 372 provide in a flange 374 which extends outwardly from the distal end of rearward housing 272. This rivet connection enables forward housing 270 to articulate relative to rearward housing 272.

Rearward housing 272 is defined by a channel of U-shaped cross-section having opposed side walls 376 and 378 and a bottom wall 380. Locking slots 382 and 384 are formed in the opposed side walls 376 and 378 adjacent the proximal end thereof for engaging and retaining support structure 214 (see FIG. 15). A pair of opposed crimps 386 and 388 are provided in opposed side walls 376 and 378 adjacent locking slots 382 and 384 for establishing a friction fit with cam bar adapter 300 (or in the alternative cam bar adapter 320) within which the dual cam bars 286 and 288 are mounted.

Figure 28:
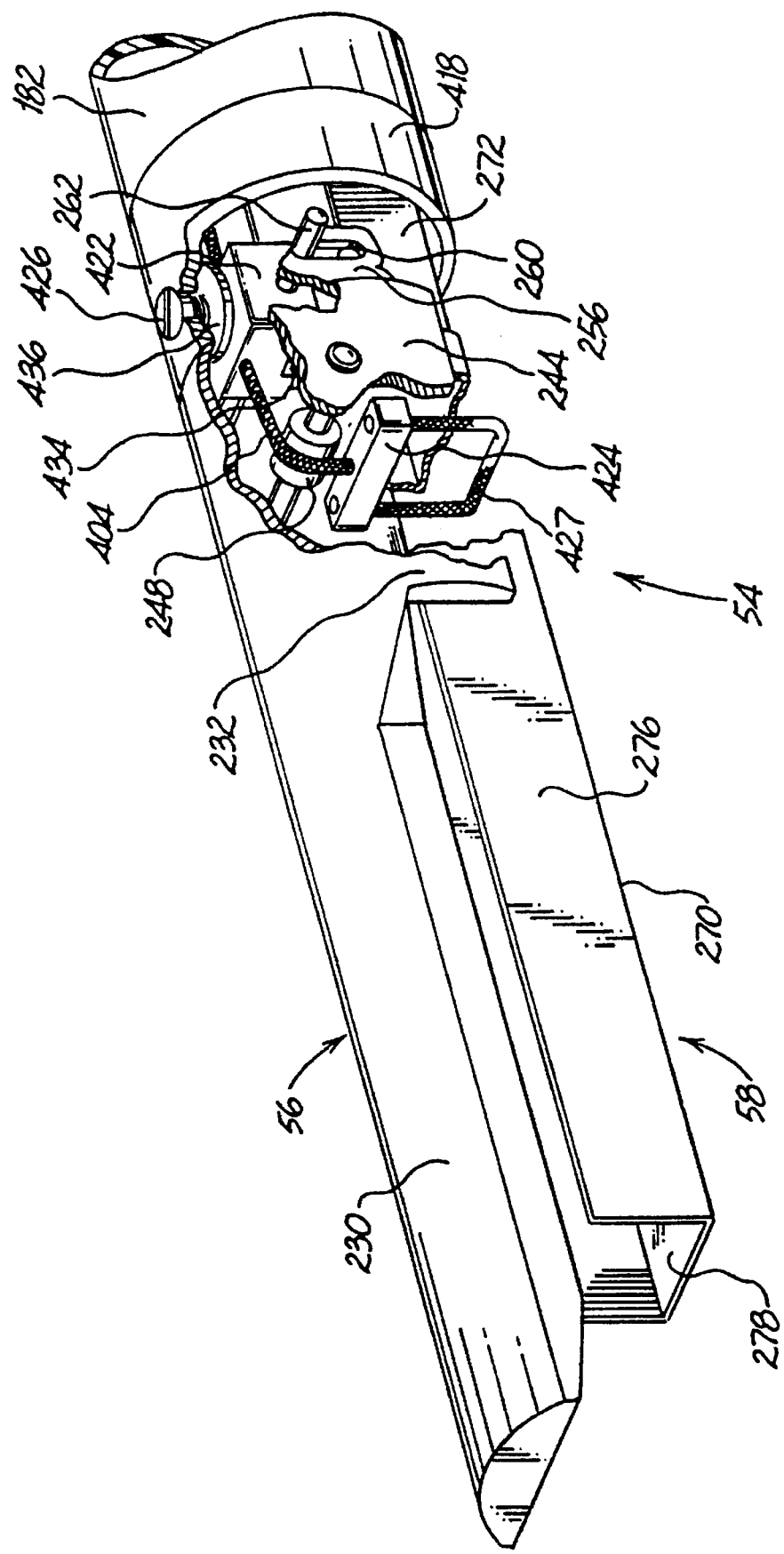
FIG. 28 is an enlarged perspective view, partially cut-away, of the distal end of the elongated portion of the subject invention showing the mechanisms provided therein.

Referring now to FIGS. 15, 16, and 28, the movement of anvil member 56 relative to cartridge assembly 58 in this embodiment is achieved through a linkage and cable system. This system includes a tube collar 400 which mounts on the distal end of combined upper and lower extension spacers 210, 212. Tube collar 400 has an internal partition wall 402 formed therein through which extends an aperture having a diameter which permits the passage of a cable 404 therethrough, while prohibiting the passage of an anchor ball 406 which is fastened to the trailing end of cable 404. As it extends from partition wall 402, the line of action of cable 404 is reversed from a proximal direction to a distal direction by turning about a pulley assembly which includes an annular pulley 410 mounted on a pulley shaft 412, and retained thereon by a locking ring 414. Pulley shaft 412 is supported in an aperture 416 provided adjacent the proximal end of support structure 214. Upon turning about pulley 410, cable 404 extends back through tube collar 400, avoiding partition wall 402 and thereafter extending through a mounting collar 418 positioned on the distal end of outer cover tube 182 of elongated portion 54. Cable 404 then extends through a longitudinal bore hole 420 formed in a pivot block 422. Pivot block 422 is rotatably mounted on a flange 424 extending from mounting collar 418 by a threaded fastener 426 maintained in threaded aperture 425. Threaded fastener 426 extends through an aperture 428 which is provided in flange 424. The function and structure of pivot block 422 will be discussed in greater detail below with respect to the mechanism for articulating cartridge assembly 58. After passing through bore hole 420 in pivot block 422, cable 404 turns about cylindrical pulley 248 which translates the line of action of cable 404 in a direction perpendicular to the longitudinal axis of elongated portion 54. The cable 404 is terminated at the trailing end thereof at an upper face of a cable separation block 424. A U-shaped anchor cable 427 extends from the opposed face of cable separator block 424 and is dimensioned and configured to engage the forward housing 270 of articulating cartridge assembly 58 so as to anchor the cable mechanism. Preferably, a cover tube, which may be formed of aluminum or a like material, clothes anchor cable 427.

The position of cable separator block 424 with respect to cylindrical pulley 248 can vary. For example, cable separator block 424 can be disposed proximal to pulley 248 as illustrated in FIG. 36. In this instance, the cylindrical pulley 248 would be configured with a pair of spaced apart annular grooves or tracks for accommodating the U-shaped anchor cable 427.

During operation of apparatus 50, reciprocating movement of the combined extension spacer 210, 212 in response to articulation of handle member 62 in frame portion 52, will cause corresponding translation of tube collar 400, thereby causing cable 404 to move in a longitudinal direction about annular pulley 410, and subsequently about cylindrical pulley 248 in a perpendicular direction. As the trailing end of cable 404 moves about pulley 248, it exerts a force thereupon which consequently causes anvil member 56 to move relative to the cartridge assembly 58.

Figure 26:
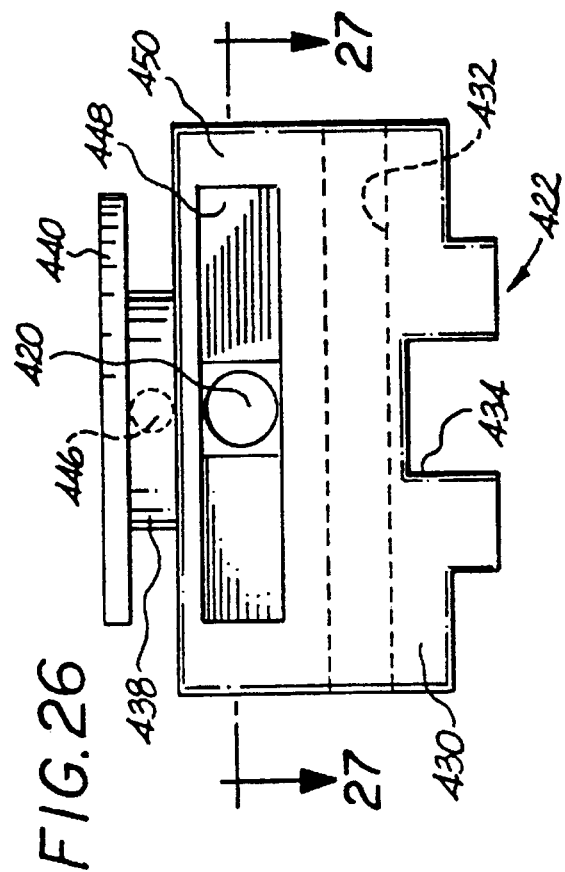
FIG. 26 is a side elevational view of the pivot block of FIG. 25.
Figure 27:
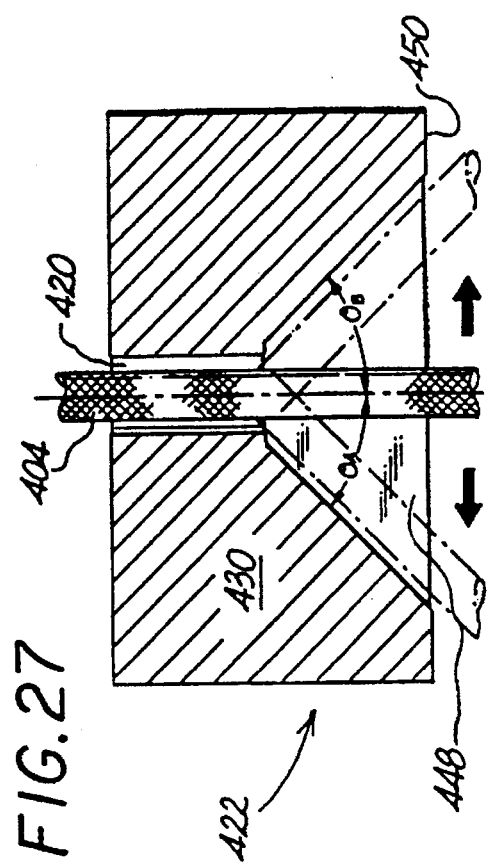
FIG. 27 is a top plan view in cross-section taken along line 27—27 of FIG. 26 showing the configuration of the cable passageway defined therein.
Figure 25:
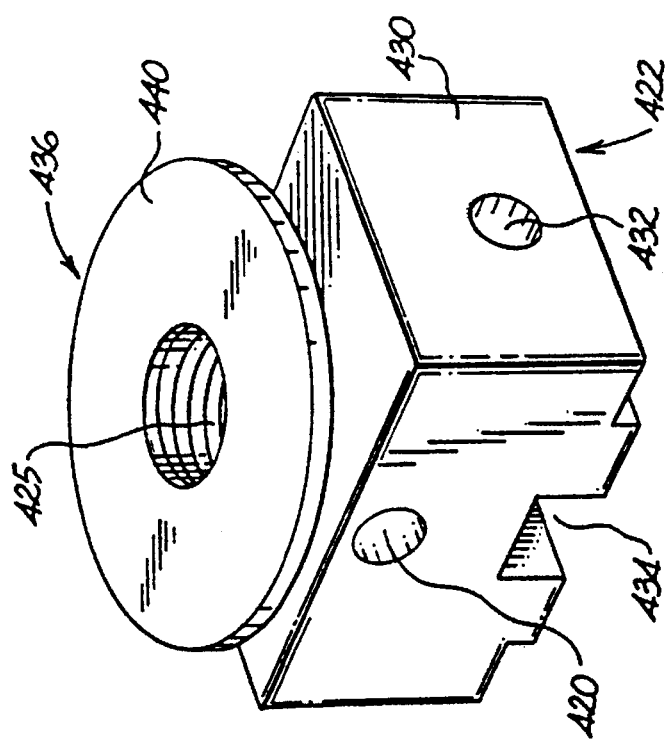
FIG. 25 is an enlarge perspective view of the pivot block illustrated in FIGS. 15 and 16.

Apparatus 50 further comprises a mechanism for effectuating the articulation of the forward housing 270 relative to the rearward housing 272 of cartridge assembly 58. The articulation mechanism includes, as stated previously, pivot block 422. As best seen in FIGS. 25–27, pivot block 422 comprises a substantially rectangular body portion 430 through which extends longitudinal bore hole 420, and a transverse bore hole 432 for receiving pivot pin 262 about which anvil member 56 pivots when the cable and linkage system is employed as described hereinabove. A longitudinal groove 434 is provided in the undersurface of body portion 430 for permitting passage of knife 240 as it traverses cartridge assembly 58 mounted upon cam bar adapter 300. A fixed capstan 436 comprising a shaft portion 438 and a hood portion 440 extends upwardly from the body portion 430 of pivot block 422 about which an articulation cable 442 of looped configuration is supported. More particularly, cable 442 has an anchor ball 444 intermediate its length which is dimensioned and configured to be fixed within a port 446 formed in shaft portion 438 of capstan 436 (see FIG. 26).

As best seen in FIG. 27, the walls of longitudinal bore hole 420 diverge 45° from the central axis thereof at a central point within body portion 432 so as to define a mouth 448 at the proximal face 450 of pivot block 422. The diverging mouth 448 of longitudinal bore hole 420 enables the relative movement of cable 404 during articulating movement of cartridge assembly 58 within a 90° sector of translation wherein $T_A$ and $T_B$ are each equal to 45°. It is also envisioned that, where a wider section of translation is desired, pivot block 422 and any associated structural elements of the apparatus may be modified to achieve at least 60° of articulation in either direction relative to the longitudinal axis of the instrument. The section of articulation cable 442 opposite anchor ball 444 is connected to a dial member 452 which is provided in the elongated portion 54 adjacent the proximal end thereof. Rotation of dial member 452 in either the clockwise or counter clockwise direction (see FIGS. 31 and 32, respectively) will cause articulating cable 442 to translate in such a manner so as to cause pivot block 422 to rotate on an axis perpendicular to the longitudinal axis of elongated portion 54 about threaded fastener 426. Consequently, anvil member 56, which is connected to pivot block 422 through pin member 262, and forward housing 270 which is operatively associated with anvil member 56 through U-shaped anchor cable 427, is caused to pivot about rivet member 370.

In use, the elongated portion 54 of instrument 50 is inserted into the body, preferably through an endoscopic tube. It is further preferred that the endoscopic tube apparatus be capable of maintaining a sealed pneumoperitoneum, with the internal sealing member of the housing further maintaining this seal despite introduction of the instrument in accordance with the invention into the endoscopic tube. As a practical matter, the jaws of the instrument are closed for insertion into the endoscopic tube, either by pinching the anvil and cartridge prior to insertion or by closing the articulating handle to cam the jaws closed prior to insertion.

Figure 29:
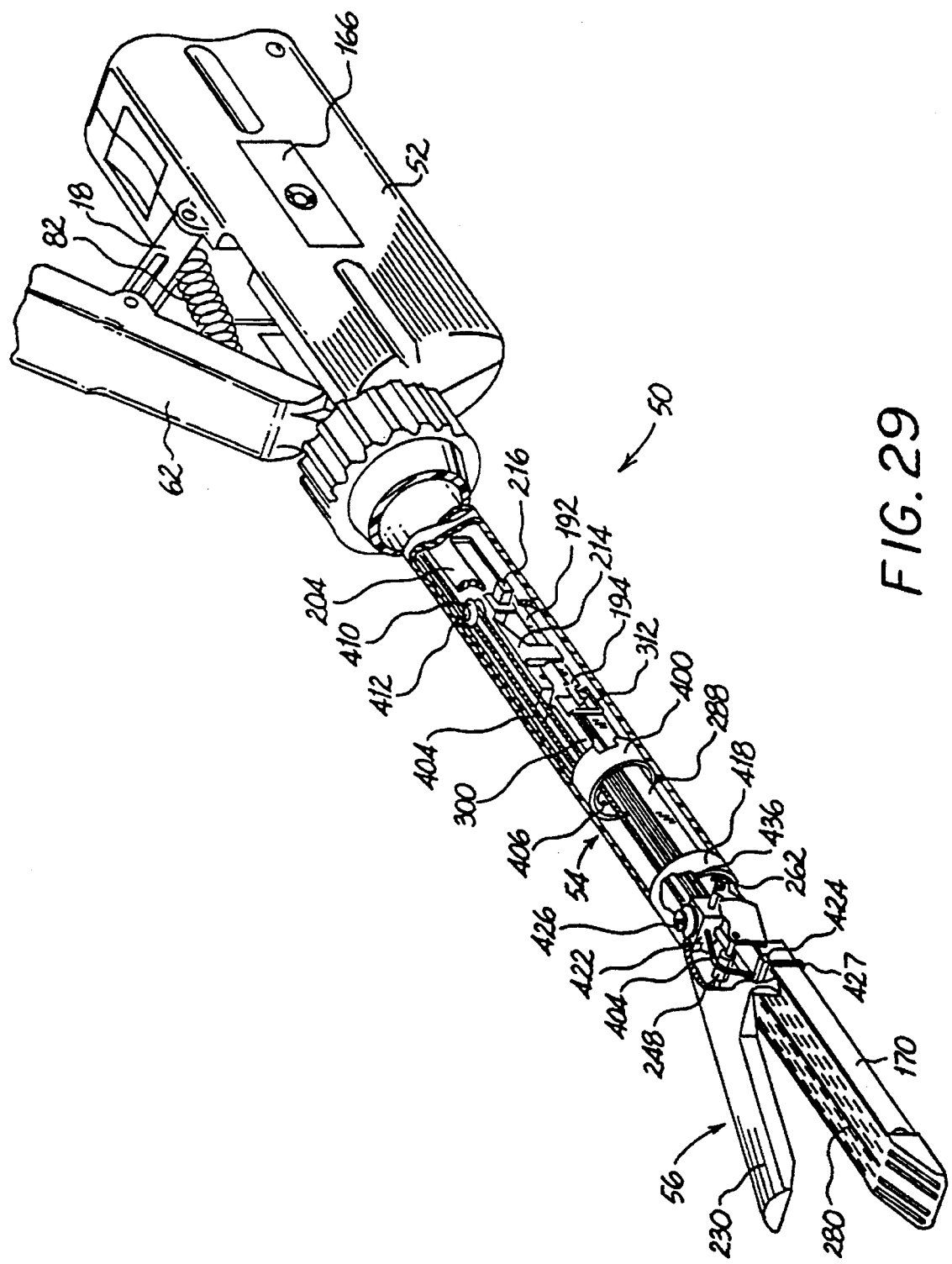
FIG. 29 is a perspective view, partially cut-away, of the surgical instrument of FIG. 1 with the anvil member in an opened position.
Figure 30:
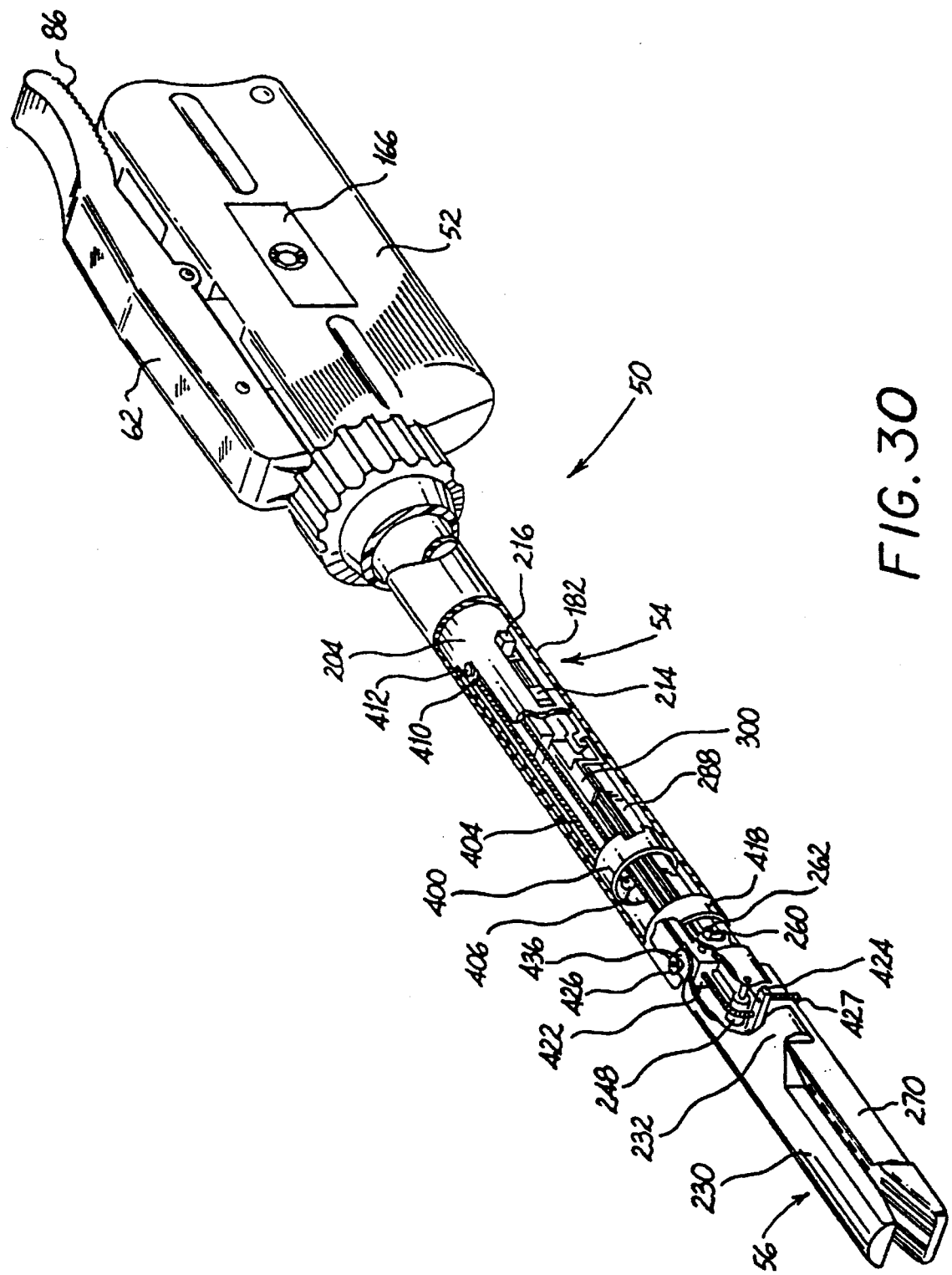
FIG. 30 is a perspective view, partially cut-away, of the surgical instrument of FIG. 1 with the anvil member in a closed position.

Referring to FIGS. 29 and 30, with the instrument properly oriented so that the tissue to be fastened is disposed between the open jaws of the instrument, i.e., between the tissue contacting surfaces of anvil member 56 and cartridge 280, the jaws are closed to clamp the tissue. Closure of the jaws is achieved as the surgeon presses down on articulating handle member 62, so as to slide tube collar 400 distally, via clamp tube 70, extension sleeve 204, and extension spacers 210, 212.

Figure 31:
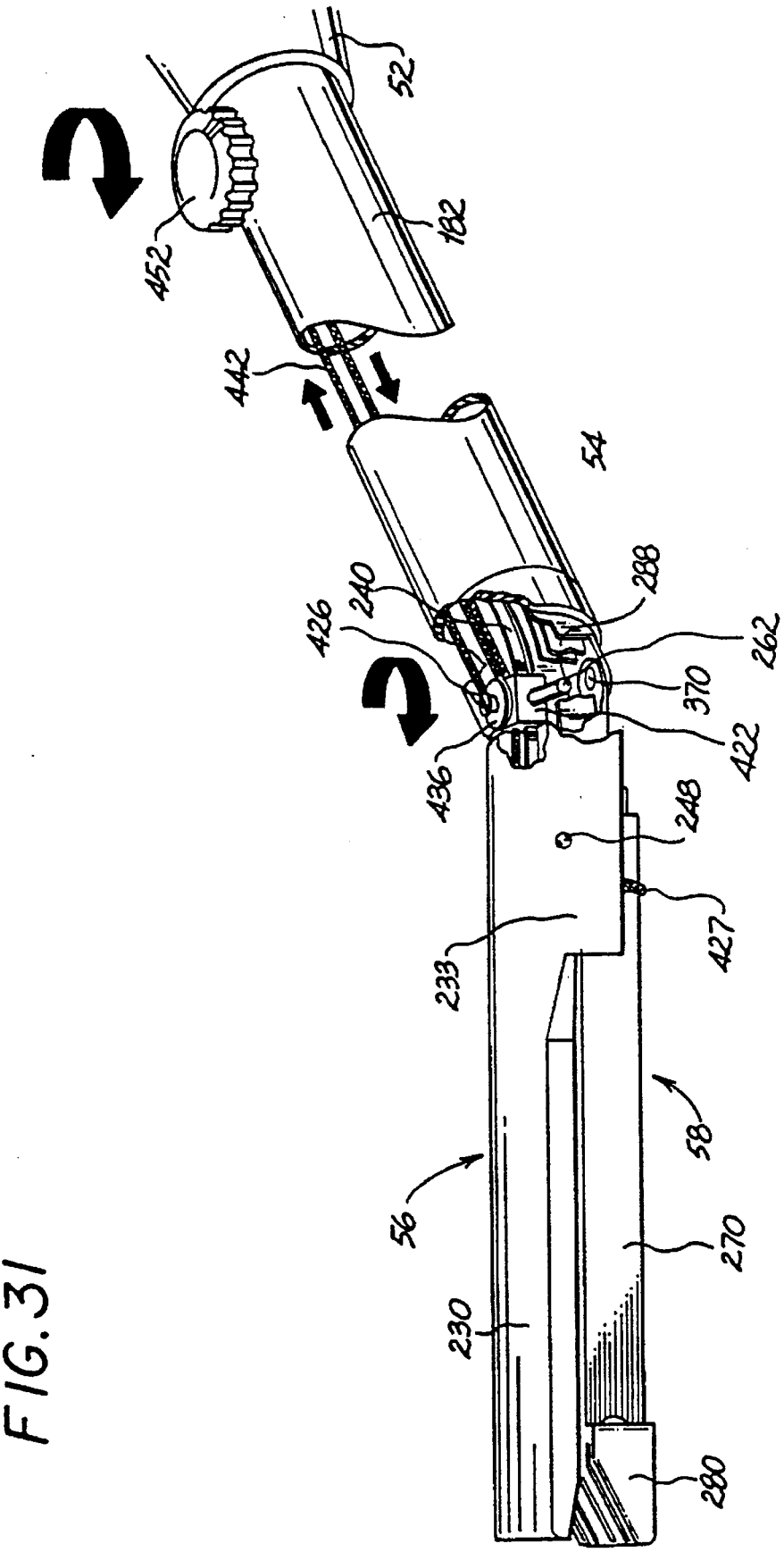
FIG. 31 is an enlarged perspective view, partially cut-away, of the cartridge assembly of the apparatus of FIG. 1 in a first articulated position.
Figure 32:
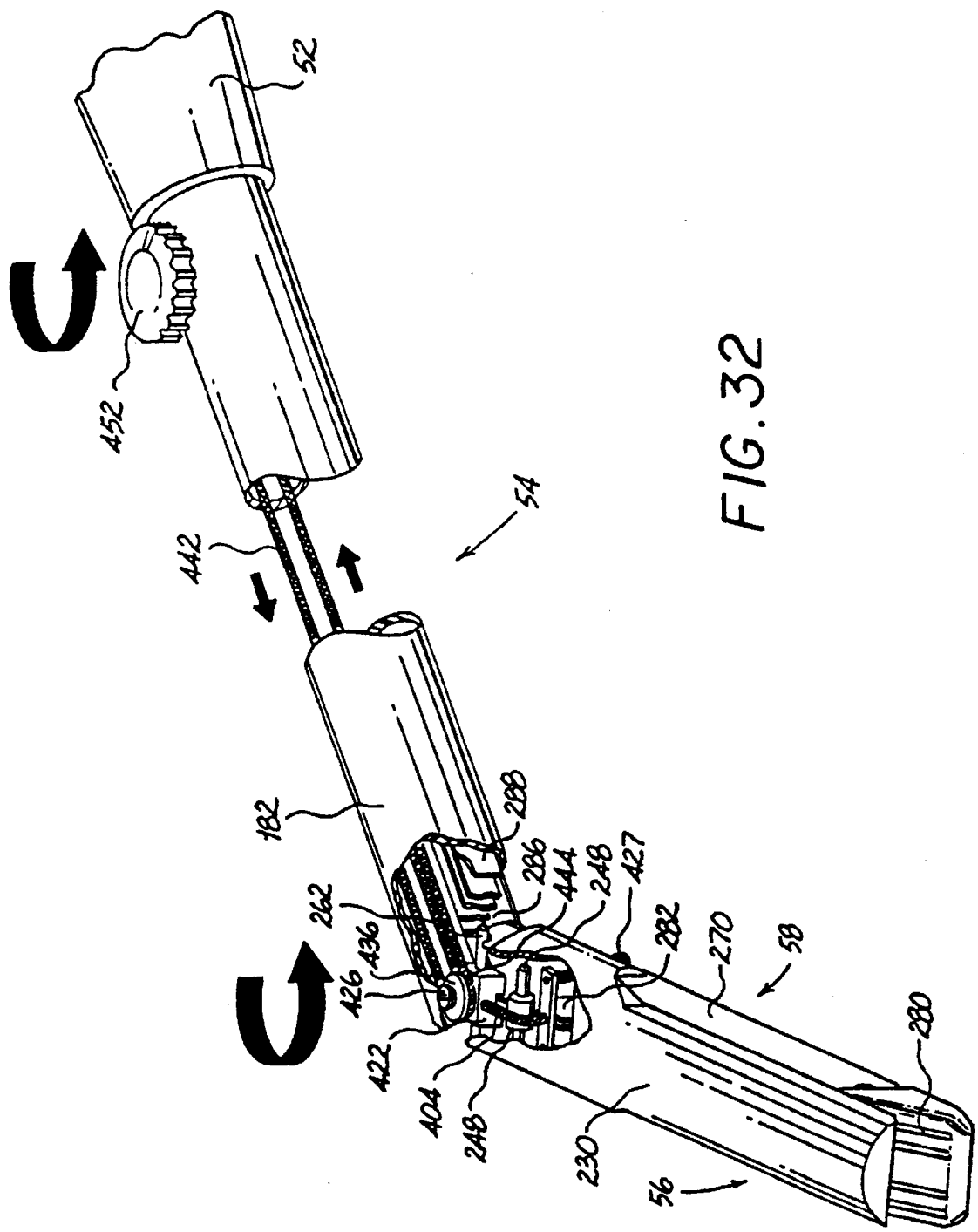
FIG. 32 is an enlarged perspective view, partially cut-away, of the cartridge assembly of the apparatus of FIG. 1 in a second articulated position.

The leading end of cable 404 is drawn in a distal direction as anchor ball 406 is maintained against partition wall 402. As the leading end of cable 404 is drawn distally, the intermediate section thereof which is turned about annular pulley 410 is drawn in a proximal direction. Consequently, the trailing end of cable 404 is urged in an upward direction, perpendicular to the longitudinal axis of elongated portion 54, as it turns about cylindrical pulley 248, thereby exerting a downward force upon pulley 248 and urging anvil member 56 to approximate toward the tissue engaging surface of cartridge assembly 58.

Where articulation is necessary or desired to orient the jaws prior to clamping, the forward housing 270 of cartridge assembly 58 may be articulated relative to the elongated portion 54 of apparatus 50 within a 90° sector of rotation, and in particular within a 45° sector of rotation on either side of the longitudinal axis of the elongated portion 54 of apparatus 50. Referring to FIG. 31, clockwise rotation of dial member 452 will result in clockwise articulation of forward housing 270 and anvil member 58. In particular, as dial member 452 is rotated, the lateral portions of articulation cable loop 426 translate in opposite longitudinal directions causing anchor ball 444 mounted in the shaft portion 438 of fixed capstan 436 of pivot block 422 to urge pivot block 422 in such a manner so as to rotate in a clockwise direction about threaded fastener 426. At such a time, the forward housing 270 pivots about rivet 370 relative to the rearward mounting portion 272 of cartridge assembly 58. Similarly, rotation of dial member 452 in a counter-clockwise direction as shown in FIG. 32, will articulate cartridge assembly.

After closing the instrument jaws, the instrument is ready to be fired. When the surgeon is ready to emplace the staples and cut tissue, firing trigger 96 is depressed to actuate the pneumatic actuator 98 as discussed in detail above. Piston 104, attached to the proximal end of channel 192 is driven distally causing the camming surface of forked portion 194 to ride up and over projection 362 of the cam bar adapter 300 and drive the cam bar adapter in a distal direction. Thereupon, the cam bars 286 and 288 and knife 240 are driven longitudinally through the cartridge to sequentially drive and form staples.

As piston 104 contacts return springs 140, 142, pusher washers 186 are compressed on themselves and serve to store energy as the piston moves distally toward the cartridge assembly. This initial compression occurs in the range of between about 20 p.s.i. to about 150 p.s.i. and preferably within a range of about 30 p.s.i. to about 60 p.s.i. Near the end of the distal stroke of the piston 104, this stored energy is released to drive the cam bars 286 and 288 through the final distal limits of their travel within the longitudinal slots in the cartridge 250. At the distal extreme of the longitudinal stroke, the overhanging ledges 292 of cam bars 286 and 288 drop over the edge of the forward cartridge housing 270 thus abutting vertical surface thereof.

Figure 35:
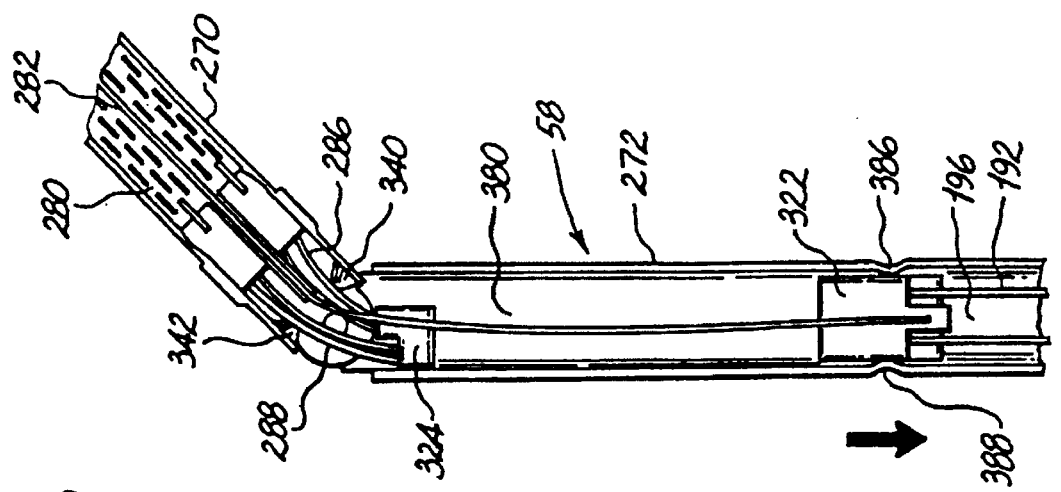
Figure 34:
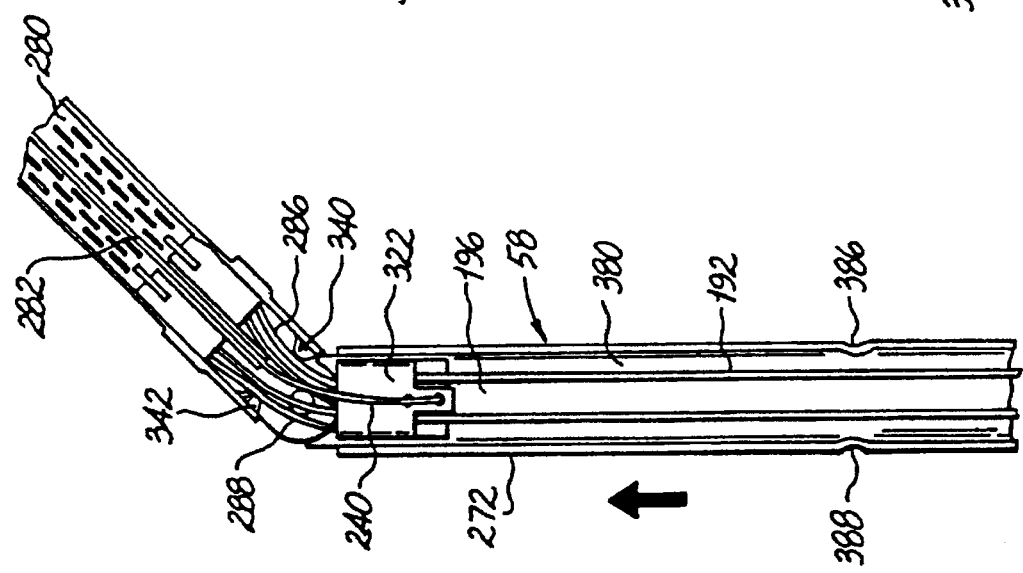
Figure 33:
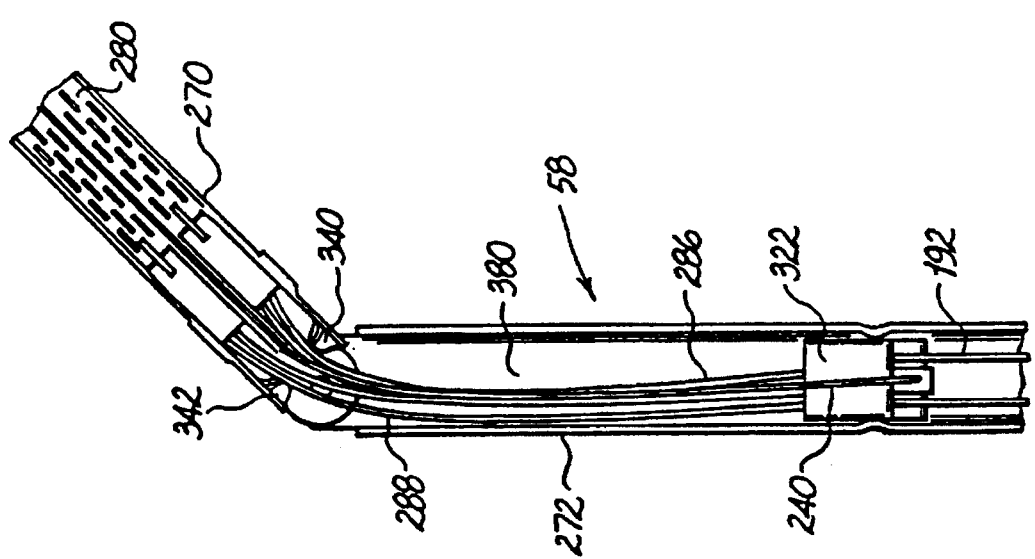

Referring to FIGS. 33 and 35, after firing, return springs 140, 142 engage piston 104 and return it to its original position. The return motion of piston 104 causes rocking lever 120 to be cammed aside by camming surface 144 of piston 104. Subsequently, the L-shaped support fixture and cam bars 286 and 288 are pulled out of cam bar adapter 320 and remain in position in the longitudinal slots of the cartridge 280. The cam bar adapter 320, with knife 240 attached, moves proximally within rearward cartridge mounting portion 272 until the outer edges of cam bar adapter 320 impinge on crimps 296.

The cam bar adapter 320 is held in place by crimps 296 while camming surfaces 198 and 200 of forked portion 194 causes the fork to ride up and disengage with projections 312 of the cam bar adapter 300. Channel member 192 continues to move in the proximal direction until it reaches its rest position. At this point, the entire cartridge assembly 58 is deactivated.

In the event that the surgeon should accidentally attempt to again fire the instrument without replacing the deactivated cartridge with a new unfixed cartridge, the resulting distal longitudinal motion of the channel 192 moves abutting structure 202 into contact with rearward projection 290 effectively preventing further movement of forked portion 194 toward cam bar adapter 280.

After firing, articulating handle 62 is raised with the assistance of handle return spring 82 which action retracts collar tube 400. This retraction causes anvil 56 to move of engagement with cartridge assembly 58. Similarly, raising of articulating handle 62 causes cam slide 124 to move upward disengaging the pneumatic firing mechanism.

In order to replace the articulating cartridge assembly 58, the instrument is withdrawn from the patient. Thereafter, the cartridge assembly is removed from the elongated portion 54 of apparatus 50. To reinsert a new cartridge assembly, the proximal mounting portion 272 of cartridge assembly 58 is inserted into the distal end of elongated portion 54. The instrument is now ready for reinsertion and continued use.

Turning now to FIGS. 36 and 38, another preferred embodiment of the surgical apparatus of the subject invention is illustrated and is designated generally by reference numeral 500. Surgical apparatus 500 functions in much the same manner as the surgical instrument 50 previously described, with the exception of the mechanism for effectuating the articulation of the cartridge assembly 58. Specifically, the articulation mechanism of surgical apparatus 500 comprises two assemblies, including a parallel crank linkage assembly 505 disposed adjacent the cartridge assembly 58 at the distal end of elongated portion 54, and an actuation assembly, shown generally at 510, located adjacent the frame portion 52 of the apparatus at the proximal end of elongated portion 54. In the discussion which follows, both the linkage assembly 505 and the axial barrel cam assembly 510 will be described with respect to various embodiments. It will be appreciated however, by those having ordinary skill in the art, that any of the assemblies described herein may be modified to incorporate features shown in the various preferred embodiments.

Figure 40:
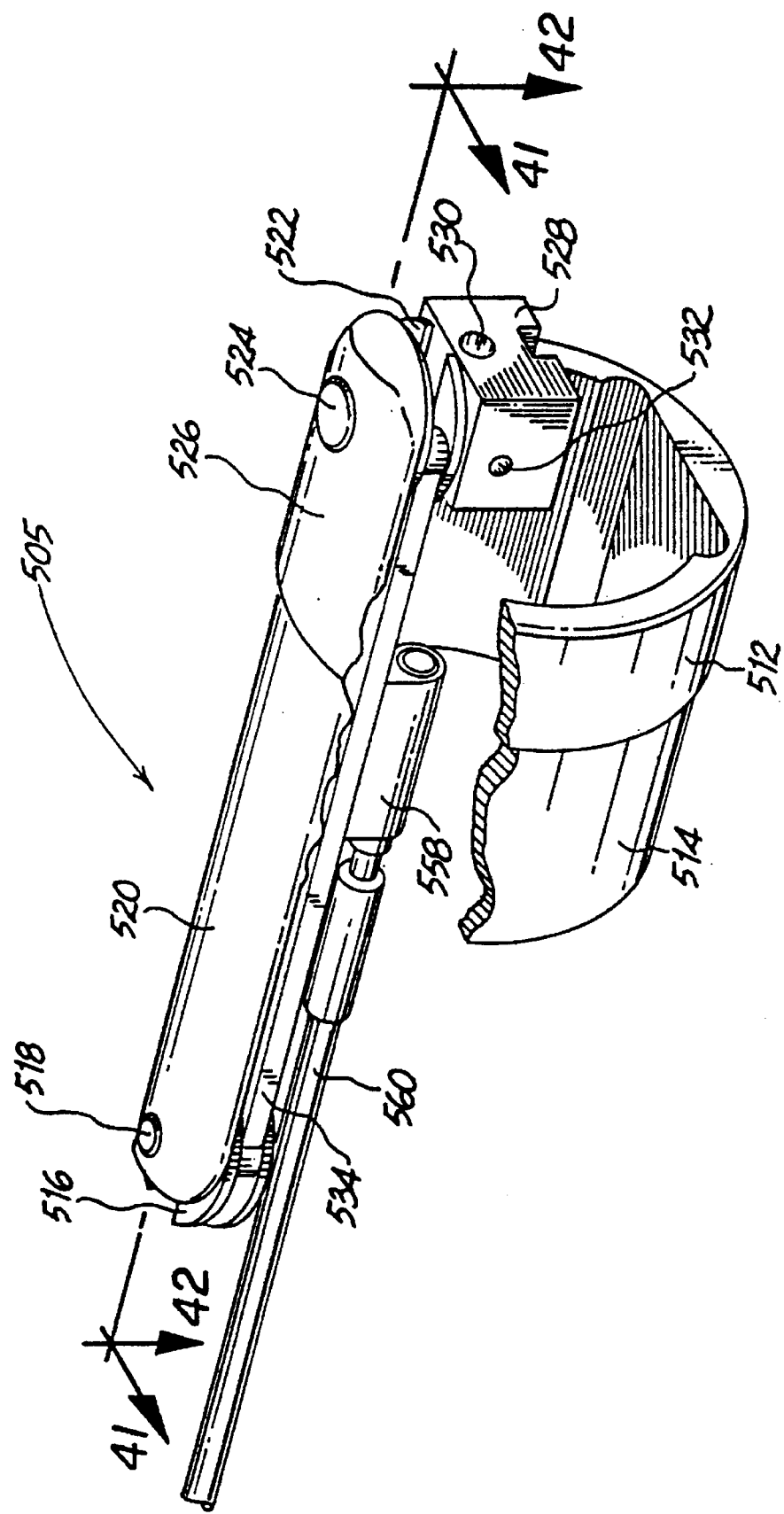
FIG. 40 is an enlarged perspective view, partially cut-away, of the mechanism for effectuating the articulation of the surgical instrument of FIG. 36.
Figure 45:
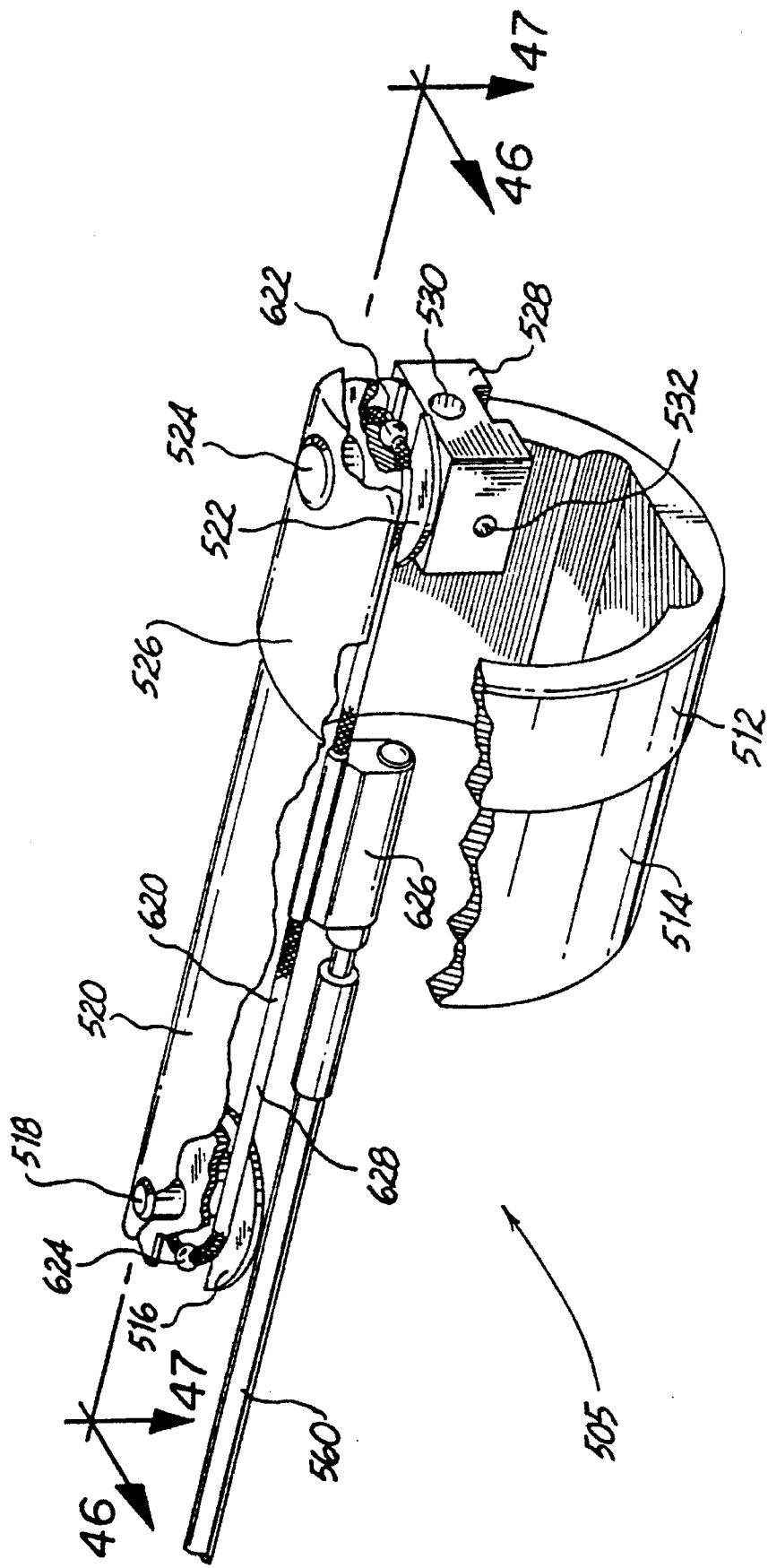
FIG. 45 is an enlarged perspective view, partially cut-away, of another embodiment of the mechanism for effectuating the articulation of the surgical instrument of FIG. 36.
Figure 46:
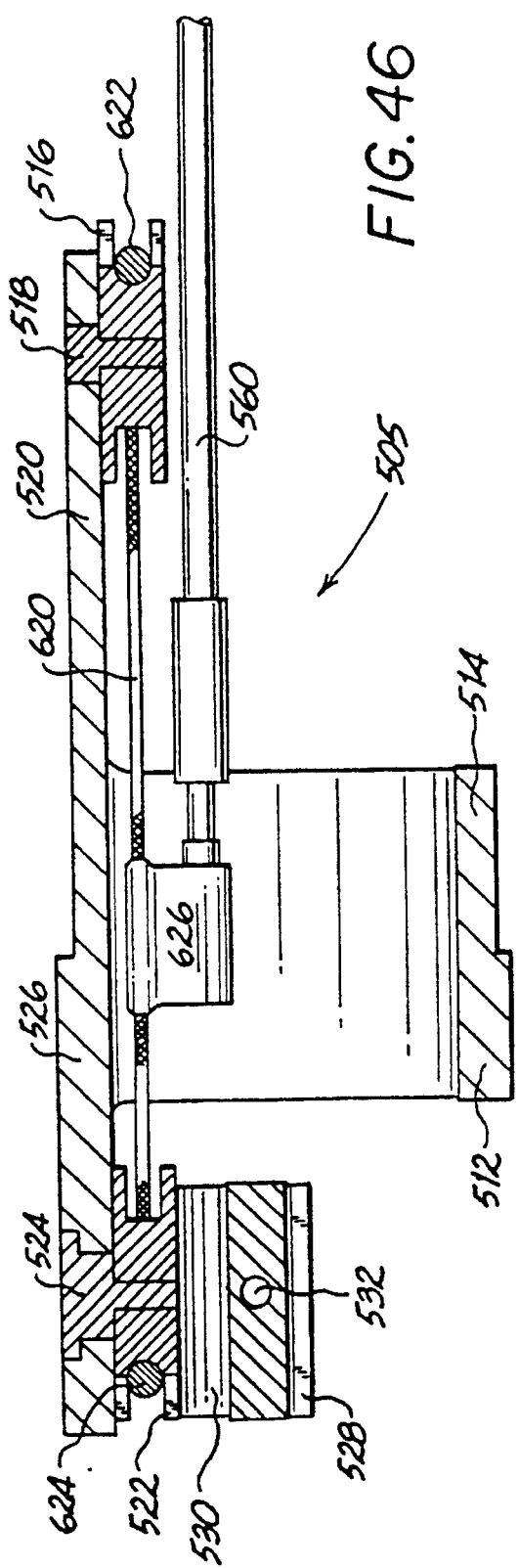
FIG. 46 is a cross-sectional view taken along line 46—46 of FIG. 45.

Turning to FIGS. 40-42, the parallel crank linkage assembly 505 of surgical apparatus 500 is associated with a mounting collar 512 having an engaging portion 514 adapted for mounting with the distal end of cover tube 182. The linkage assembly 505 includes a proximal crank member 516 mounted for rotation about a pivot pin 518 which extends through the rearward flange portion 520 of mounting collar 512. Pivot pin 518 is disposed perpendicular to the longitudinal axis of elongated portion 54. Longitudinally spaced from proximal crank member 516, a distal crank member 522 is mounted for rotation about a pivot pin 524. Pivot pin 524 extends through the forward flange portion 526 of mounting collar 512 and is disposed parallel to pivot pin 518. Distal crank 522 is associated with a pivot block 528 having a longitudinal bore 530 extending therethrough for accommodating cable 404. As previously described herein, cable 404 is associated with moving anvil member 56 between an open position and a closed position for clamping tissue. Pivot block 528 is also provided with a transverse bore 532 for accommodating the transverse pin 262 about which anvil member 56 pivots as it is moved between its open and closed positions.

Linkage assembly 505 further comprises a pair of parallel coupler links 534 and 536 which operatively interconnect the proximal crank member 516 and distal crank member 522. Link 534 has a longitudinal span 538 with a transverse engaging slot 540 formed at a distal end thereof for engaging a pin 542 associated with distal crank 522, and a transverse engaging slot 544 is provided at the proximal end thereof for engaging another pin 546 associated with the proximal crank 516. Similarly, link 536 has a longitudinal span 548 with a transverse engaging slot 550 provided at the distal end thereof for engaging a pin 552 associated with the distal crank member 522, and a transverse slot 554 is formed at the proximal end thereof for engaging yet another pin 556 disposed on the proximal crank member 516. Of the two coupler links 534 and 536, link 534 defines a driver link, while link 536 defines a follower link. Moreover, driver link 536 is provided with a coupling 558, which depends from the undersurface thereof, intermediate span 538 for receiving and mounting the distal end of an elongated transmission rod 560. Transmission rod 560 extends through the elongated portion 54 of surgical apparatus 500 for transmitting reciprocal longitudinal motion to driver link 534 in response to manipulation of the axial barrel cam assembly 510. Transverse slots 540, 544, 550, and 554 permit coupler links 534 and 536 to remain parallel to a longitudinal axis of the linkage assembly 505 during transmission of the reciprocal longitudinal motion by rod 560.

Referring again to FIGS. 36-39, the actuation assembly 510 of surgical apparatus 500 comprises a generally cylindrical manipulator sleeve 562 disposed about the proximal section of elongated portion 54. Manipulator sleeve 562 is configured and dimensioned for axial movement with respect to the longitudinal axis of elongated portion 54. In particular, manipulator sleeve 562 may be rotated about the longitudinal axis of elongated portion 54 to rotate the cartridge assembly 58 relative to the frame portion 52 of apparatus 500, and reciprocally in a generally longitudinal direction for effectuating the articulation of cartridge assembly 58 so as to increase the range of operability of the instrument, which will be described in greater detail hereinbelow.

A barrel cam 564 having a substantially hemi-cylindrical configuration is associated with manipulator sleeve 562 and is configured and dimensioned for rotational movement as sleeve 562 is manipulated in a longitudinal direction to drive transmission rod 560. Relative rotational movement of barrel cam 564 is facilitated by the interaction of a cam follower pin 566 extending radially inward from manipulator sleeve 562, and a cam slot 568 defined in barrel cam 564. Cam slot 568 has a three stage configuration including an upper step region 570, a central step region 572, and a lower step region 574. When articulating the cartridge assembly 58 of surgical apparatus 500 in a counter-clockwise direction, sleeve 562 is manipulated in a proximal direction, moving cam follower pin 566 from the central step region 572, wherein cartridge assembly 58 is in substantial longitudinal alignment with the elongated portion 54 of the instrument, to the upper step region 570 of cam slot 568, to axially rotate barrel cam 564.

To articulate cartridge assembly 58 in clockwise direction, sleeve 562 is manipulated in a distal direction, moving cam follower pin 566 to the lower step region 574 of cam slot 568, and thereby axially rotating barrel cam 564. The longitudinal dimension of cam slot 568 can be modified depending upon the tactile sensation desired to be transmitted to the user of the instrument. In addition, an annular rib 563 (see FIG. 38) extending radially outward from the cover tube 182 of elongated portion 54, distal to manipulator sleeve 562, serves to prevent over-insertion of the elongated portion 54 of surgical apparatus 500 into a trocar or cannula device.

As stated briefly above, the rotational movement of barrel cam 564 is conveyed to transmission red 560 for effectuating the articulation of cartridge assembly 58. This conveyance of rotational motion is accomplished by engaging an arm 580 formed at the proximal end the proximal end of transmission rod 560 within an angle drive slot 582 defined in barrel cam 564. Thus, as barrel cam 564 rotates in response to the translation of cam follower pin 566 within cam slot 568, transmission rod 560 is advantageously driven in a longitudinal direction as the peripheral walls of angled drive slot 582 are urged against the engaging arm 580 thereof. To secure the engagement of arm 580 within angled drive slot 582, a connective fitting 584 is mounted atop engagement arm 576 and is configured and dimensioned to move within longitudinal channel 585 formed in an inner surface of manipulation sleeve 562.

Barrel cam 564 is also provided with a pair of spaced apart transverse alignment slots 586 and 588 which are adapted and configured for cooperatively receiving a pair of guide pins 590 and 592. Guide pins 590 and 592 are associated with the outer tube 182 of elongated portion 54 and inhibit undesirable longitudinal shifting of the barrel cam 564 which may arise as sleeve 562 is manipulated. In addition, guide pins 590 and 592 achieve connection between the outer tube 182 of elongated portion 54 and the manipulator sleeve 662 via the interaction of cam follower pin 566 and cam slot 568. This connection is further assisted by the provision of a spring loaded locking mechanism associated with manipulator sleeve 562.

As best seen in FIGS. 37 and 39, the locking mechanism includes a lock ball 594 which is biased by a coiled spring 596 maintained within a cavity 598 formed within manipulator sleeve 562. Lock ball 594 is selectively engageable within a plurality of spaced apart notches disposed about the outer circumference of cover tube 182 and including a primary notch 600 corresponding to the cam follower pin 566 being disposed in the upper step region 570 of cam slot 568, a secondary notch 602 corresponding to cam follower pin 566 being disposed in the central step region 572 of cam slot 568, and a tertiary notch 603 corresponding to cam follower pin 566 being disposed in the lower step region 574 of cam slot 568. By lockingly engaging the cover tube 182 of elongated portion 54, rotation of manipulator sleeve 562 about the longitudinal axis of elongated portion 54 will effectuate remote rotation of cartridge assembly 58 relative to the frame portion 52 of surgical apparatus 500.

In use, as sleeve 562 is manipulated in a distal direction (see FIG. 38), transmission rod 560 will translate in a proximal direction with respect to elongated portion 54, pulling driver link 534 proximally as indicated by arrow "A" in FIG. 43. In response, distal crank member 522 is rotated about pivot pin 524, thereby mining pivot block 528 in a clockwise direction. As pivot block 528 is operatively connected to anvil member 56 through transverse pin 262, the forward housing 270 of cartridge assembly 58 is caused to articulate in a clockwise direction. Similarly, in response to manipulation of sleeve 562 in a proximal direction (see FIG. 36), transmission rod 560 will translate distally with respect to elongated portion 54, pushing driver link 534 distally as indicated by arrow "B" in FIG. 44. As a result, distal crank member 522 will turn pivot block 528 in a counter-clockwise direction, articulating the forward housing 270 of cartridge assembly 58 in a counter-clockwise direction.

Another preferred embodiment of the parallel linkage assembly 505 of the mechanism for effectuating the articulation of cartridge assembly 58 is illustrated in FIGS. 45–49. This assembly includes a looped cable 620, which replaces the parallel coupler links 534 and 536 discussed hereinabove, for operatively associating the spaced apart proximal and distal crank members 516 and 522, which, in this embodiment, serve primarily as a pair of capstans. A first ball-type fastener 622 is provided at the leading portion of cable loop 620 for securing the cable to distal crank member 522, and a second ball-type fastener 624 is provided at the trailing portion of cable loop 620 for fixing the cable to proximal crank member 516. A coupling 626 is rigidly mounted on the driving leg 628 of cable loop 620 for operatively receiving and retaining the distal end of transmission rod 560 so as to interconnect the actuation assembly 510 of surgical apparatus 500 to the linkage assembly 505 thereof.

Figure 47:
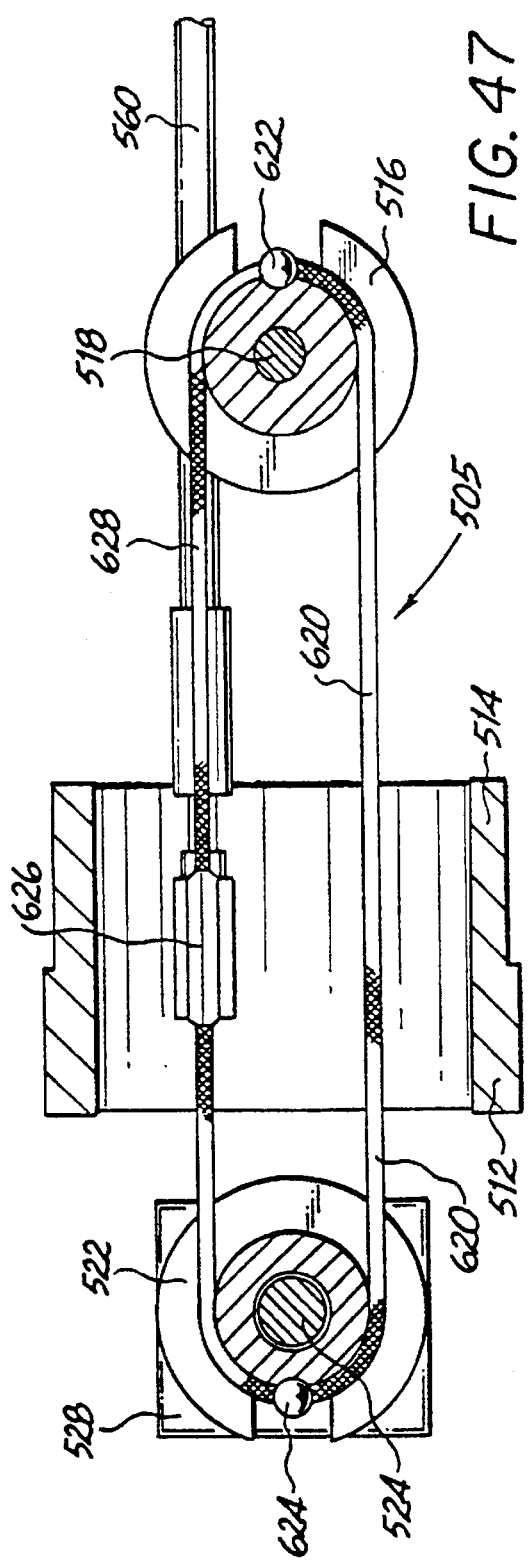
FIG. 47 is a cross-sectional view taken along line 47—47 of FIG. 45.

Referring to FIG. 47, in use, the cable loop 620 is manipulated through longitudinal translation of transmission rod 560 in response to manipulation of barrel cam assembly 510 (see FIGS. 36 and 38). Thus, proximal translation of transmission rod 560, as indicated by arrow "C" in FIG. 48, will cause cable loop 620 to rotate in a clockwise direction, turning pivot block 528 in a clockwise direction to articulate the forward housing 270 of cartridge housing 58 through an arcuate path (see FIG. 38). Similarly, distal translation of transmission rod 560, as indicated by arrow "D" in FIG. 49, will cause cable loop 620 to rotate in a counter-clockwise direction, causing distal crank member 522 to pivot in a counter-clockwise direction. As a result, the forward housing 270 of cartridge assembly 58 will be moved arcuately in a counter-clockwise direction (see FIG. 36).

Figure 51:
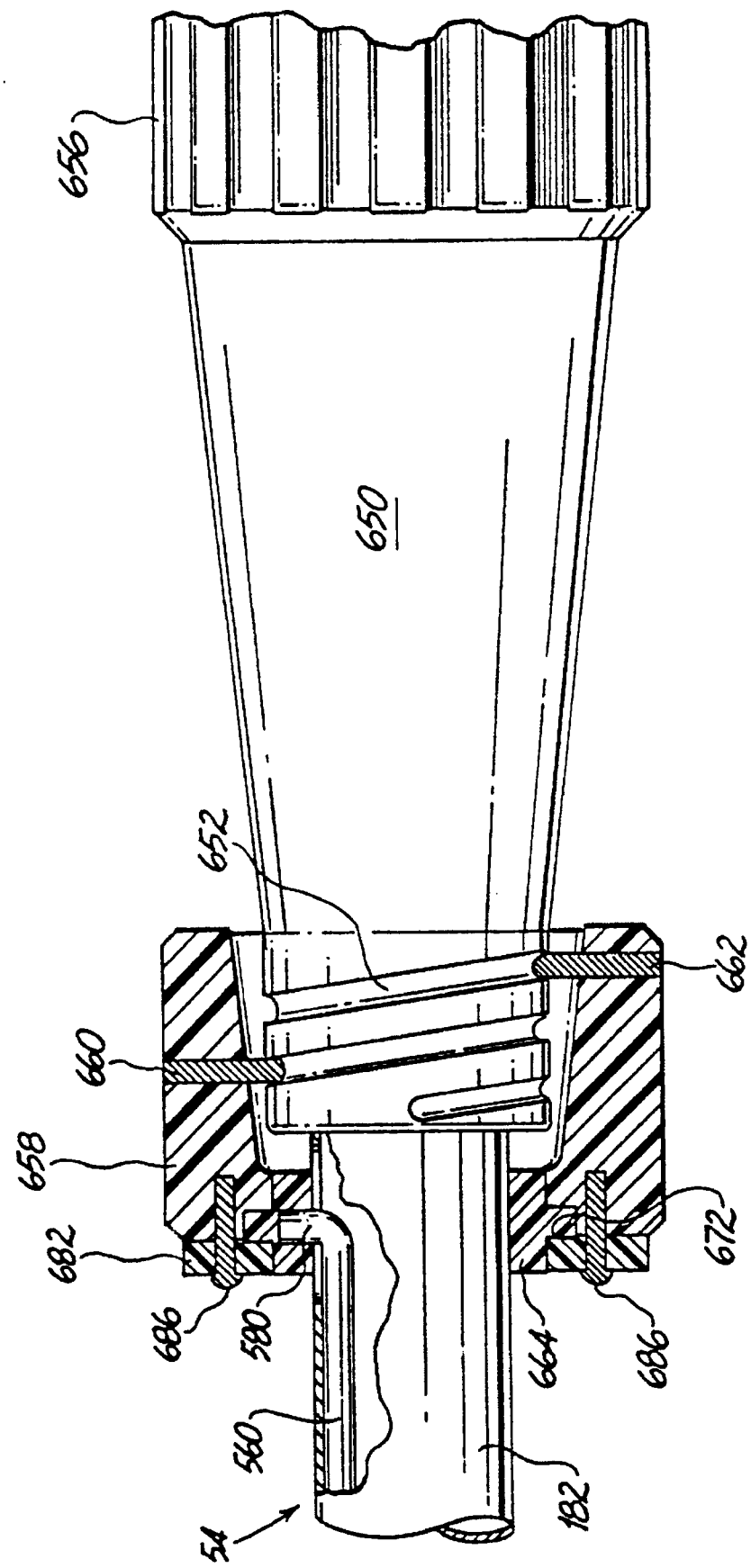
FIG. 51 is a side elevational view, partially cut-away, of the actuation member of FIG. 50.

Another preferred embodiment of the actuation assembly 510 is illustrated in FIGS. 50 and 51, and is particularly adapted and configured for progressively articulating cartridge assembly 58 within an angular sector of rotation. This assembly comprises a sleeve member 650 disposed about the elongated portion 54 of surgical apparatus 500 adjacent the frame portion 52 thereof. A continuous helical track 652 is defined about the outer circumference of the distal end portion 654 of sleeve member 650, and a knurl 656 is formed at the proximal end portion of sleeve member 650. An annular knob member 658 is mounted coaxial with the distal end portion of sleeve member 650 and is provided with a pair of opposed and staggered follower pins 660 and 662 which are configured and positioned to travel within helical track 652 as knob member 658 is rotated relative to sleeve member 650 for effecting the progressive articulation of cartridge assembly 58.

A retainer ring 664 having an annular flange portion 668 is mounted within an annular groove 670 defined in knob member 658. Retainer ring 664 is also provided with an engagement port 672 for receiving the engaging arm 580 formed at the proximal end of transmission rod 560. A pair of diametrically opposed grooves 674 and 676 are formed in the interior of retainer ring 664 for engaging a pair of opposed corresponding keys 678 and 680 which extend radially outward from the cover tube 182 of elongated portion 54 adjacent sleeve member 650. Through this engagement, rotation of transmission rod 560 will be inhibited as knob member 658 is rotated to drive transmission rod 560 in a longitudinal direction for effectuating the progressive articulation of cartridge assembly 58. However, when sleeve member 650 is rotated about the longitudinal axis of elongated portion 54, the engagement of the keys 678 and 680 within the opposed grooves 674 and 676 will effectuate rotation of cartridge assembly 58 relative to the frame portion 52 of surgical apparatus 500. Finally, a securement ring 682 is fastened to the distal face 684 of knob member 658 by a plurality of threaded fasteners 686 for maintaining retainer ring 664 within annular groove 670.

Figure 52:
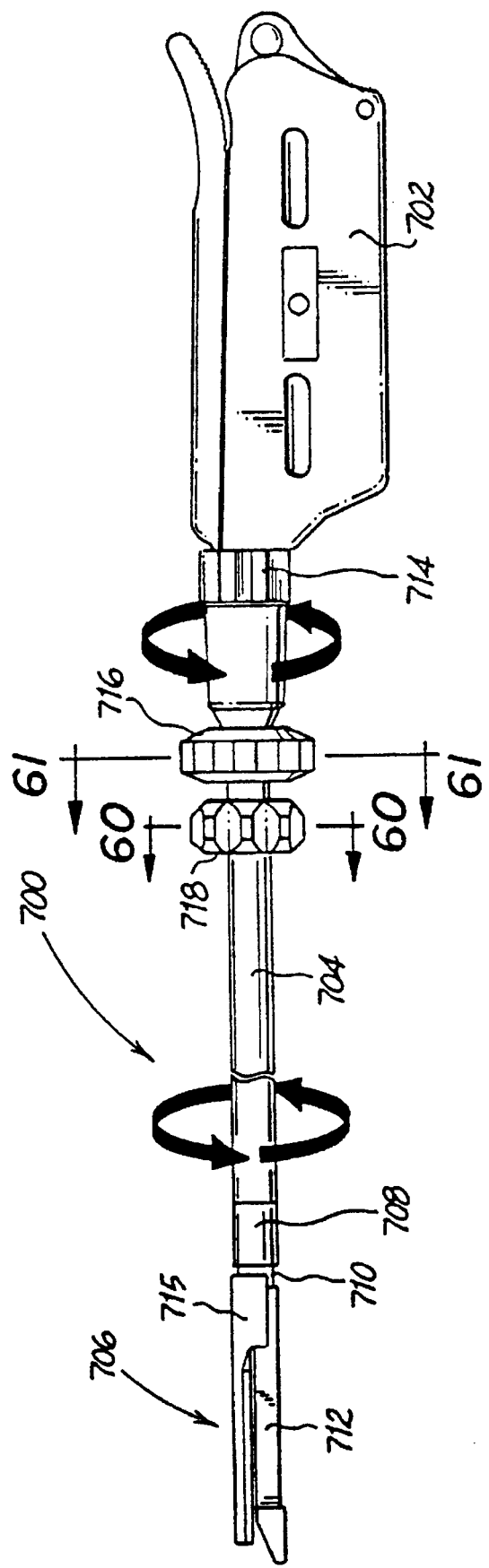
FIG. 52 is a side elevational view of another preferred embodiment of a self contained gas powered endoscopic surgical instrument in accordance with the subject invention, the distal end of which has an increased range of operability.

Referring to FIG. 52, another preferred embodiment of a surgical instrument in accordance with the subject invention is illustrated and is designated generally by reference numeral 700. This instrument is intended to provide the surgeon with a substantially increased range of operability during a surgical procedure. In brief, surgical instrument 700 comprises a frame or handle assembly 702, an elongated body portion 704 extending from the handle assembly 702 and defining a longitudinal axis, and a fastener applying assembly 706 which is pivotably associated with a distal end 708 of body portion 704.

The fastener applying assembly 706 includes a base portion 710 which is pivotably mounted to the distal end 708 of body portion 706 by means of a main joint pin 707 (see generally FIG. 63). A cartridge assembly 712 is configured to be mounted within the base portion 710 and an anvil member 715 is positioned adjacent the cartridge assembly 712 against which staples ejected from the cartridge assembly are formed (see generally FIG. 58).

Surgical instrument 700 includes three mechanisms for effectuating distinct movements of the fastener applying assembly 706. These mechanisms include a rotation control mechanism for effectuating rotation of the fastener applying assembly 706 about a longitudinal axis defined by the elongated body portion 704. This fast mechanism is operated through rotation of a control knob 714 which is fixed about the proximal end of body portion 704 (see FIG. 52). The second mechanism is an articulation control mechanism for moving the base portion 710 of the fastener applying assembly 706 relative to the elongated body portion 704 within an angular sector of rotation. This second mechanism is operated through rotation of control knob 716 (see FIG. 53). A third mechanism is provided for controlling the independent rotation of the cartridge assembly 712 together with the anvil member 715 relative to the base portion 710 of the fastener applying assembly 706 (see FIG. 54). This third mechanism is operated through rotation of control knob 718. These control mechanisms will be described in greater detail hereinbelow.

Figure 55:
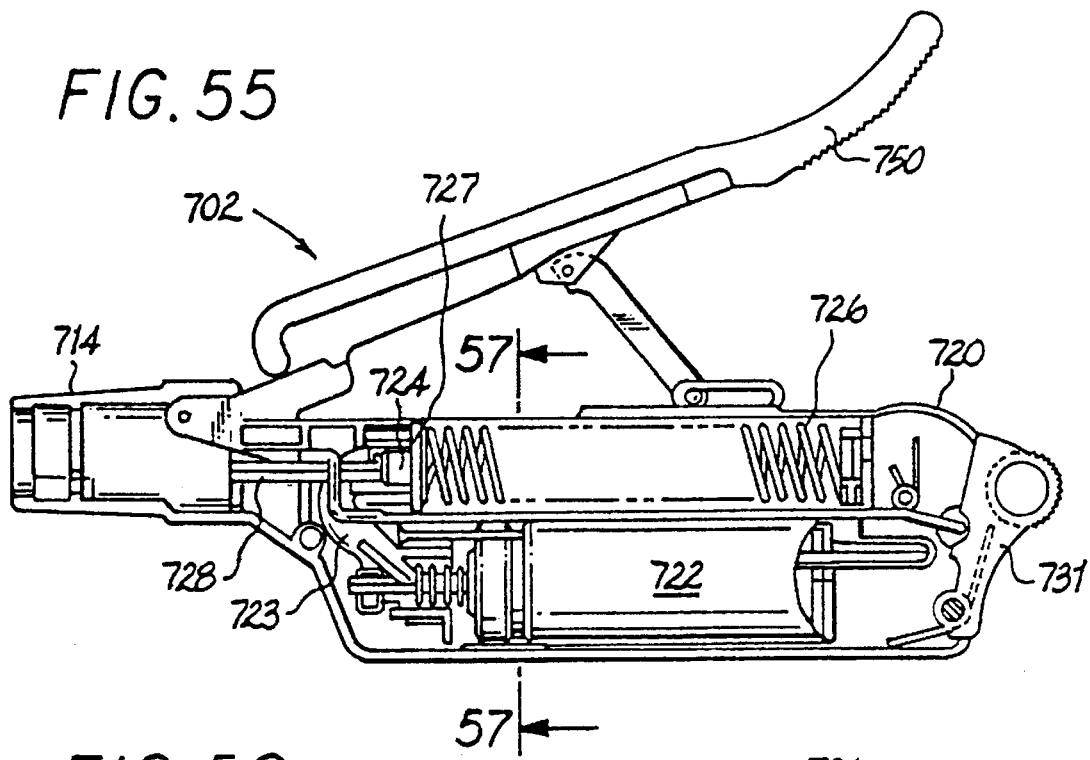
FIG. 55 is a side elevational view in cross-section of the frame or handle assembly of the surgical instrument of FIG. 52 with the actuating handle thereof in a first position.
Figure 56:
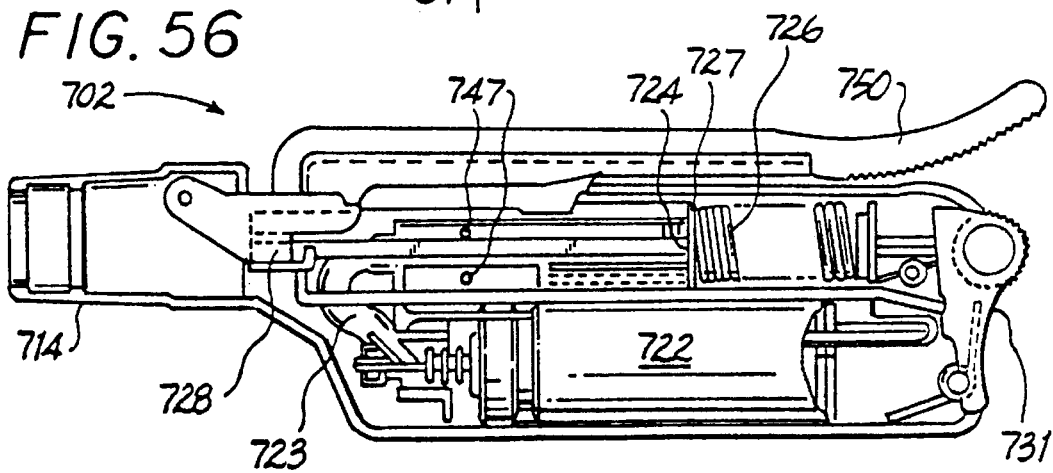
FIG. 56 is a side elevational view in cross-section of the handle assembly illustrated in FIG. 55 with the actuating handle thereof in a second position.
Figure 57:
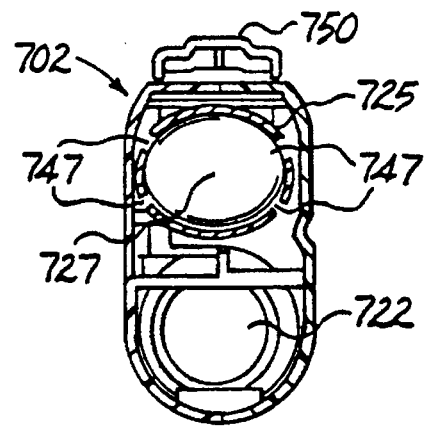
FIG. 57 is a cross-sectional view taken along line 57—57 of FIG. 55.

Referring now to FIGS. 55–57, the handle assembly 702 of surgical instrument 700 includes a handle body 720 for enclosing a pneumatic actuation assembly which is operative to effectuate the ejection of surgical staples from the cartridge assembly 712. This pneumatic assembly is similar in many respects to those described hereinabove. However, the pneumatic assembly of FIGS. 55–57 serves to create a power stroke which is directed in a proximal direction rather than a distal direction. In brief, the pneumatic assembly includes a gas supply container 722, a piston member 724 having a piston head 727 accommodated within a cylinder 725 and a coiled return spring 726. As best seen in FIG. 57, piston head 727 has a substantially elliptical configuration, as does the cylinder 725 within which it is accommodated. The elliptical configuration of piston head 727 and cylinder 725 provides increased power during a staple driving operation while maintaining substantially the same overall dimensions of the handle assembly 702. In a preferred embodiment of the invention wherein surgical instrument 700 is adapted to apply six rows of staples, each staple row measuring about 60 mm in length, and to simultaneously cut between the two innermost staple rows, the major axis of elliptical piston head 727 is between about 0.65 and 0.70 inches, and the minor axis is between about 0.45 and 0.50 inches. The corresponding elliptical cylinder 725 has a major axis of about 0.80 to 0.85 inches and a minor axis of about 0.60 to 0.65 inches. An elliptical O-ring is provided on piston head 727 to pneumatically seal piston head 727 to cylinder 725. Other cross-sectional configurations are also contemplated and are within the scope of the invention. A flexible conduit 723 connects the gas supply container 722 to piston 724 for the delivery of compressed gas. In use, the delivery of compressed gas from the container 722 is controlled by a trigger 731 disposed at the proximal end of handle body 720. Operation of trigger 731 to fire the instrument is substantially identical to that described above with respect to the other embodiments of the invention.

An elongated actuation rod 728 is associated with piston 724 and extends operatively therefrom, through the body portion 704 of surgical instrument 700, to the distal end 708 thereof. The distal end of actuation rod 728 is mounted to a cartridge adapter 730 which is illustrated in FIG. 62 in conjunction with the removable cartridge assembly 712. Adapter 730 interconnects actuation rod 728 to a stepped draw bar 732. Draw bar 732 defines a proximal section 734, an intermediate stepped section 736, and a distal section 738. The distal section 738 of draw bar 732 extends through the cartridge assembly 712, beneath the staple carrying cartridge 737 disposed therein, to connect with a staple ejecting assembly associated with the cartridge assembly 712.

Figure 62A:
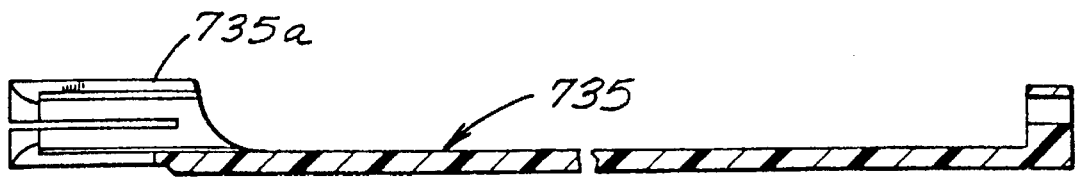
FIG. 62a is a side elevational view in cross-section of a coupling shaft which is configured to interconnect the cartridge assembly of FIG. 62 with the pneumatic actuation system disposed within the handle assembly illustrated in FIG. 55.
Figure 62B:
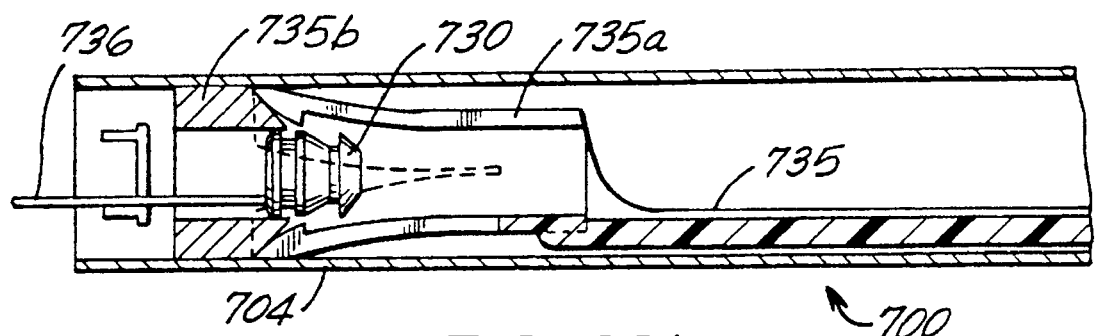
FIG. 62b a side elevational view in partial cross-section of the coupling shaft of FIG. 62a with the distal end portion thereof spread radially outward for reception of an adapter member of the cartridge assembly of FIG. 62.
Figure 62C:
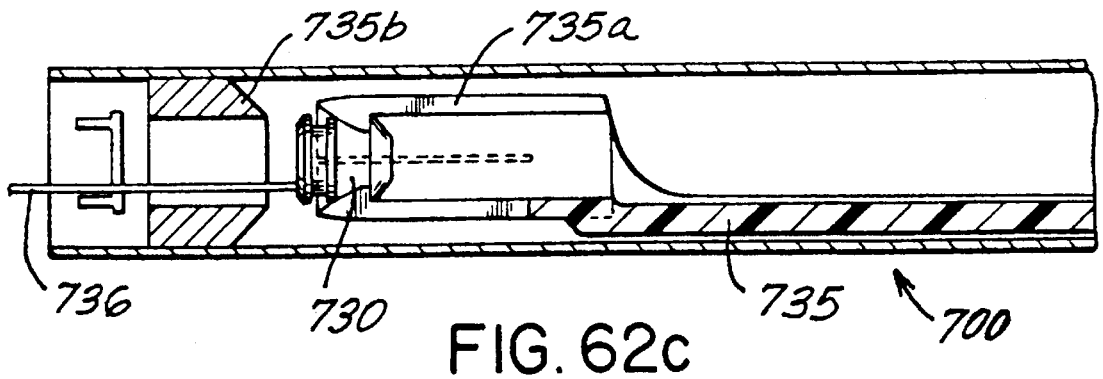
FIG. 62c is a side elevational view in partial cross-section of the coupling shaft of FIG. 62a with the adapter member of the cartridge assembly of FIG. 62 engaged within the distal end portion thereof.

Referring to FIGS. 62a–62c in conjunction with FIGS. 55 and 62, there is illustrated a coupling shaft 735 which is dimensioned and configured to operatively interconnect the actuation rod 728 and the draw bar 732. As illustrated in FIG. 62a, the distal end portion 735a of coupling shaft 735 is slotted in such a manner so as to permit the radially outward expansion thereof to facilitate the reception of adaptor 730 within coupling shaft 735 when the cartridge assembly 712 is mounted to the base portion 710 of surgical apparatus 700. As illustrated in FIG. 62b, the radially outward expansion of the distal end portion 735a of coupling shaft 735 is effected by urging the coupling shaft 735 in a distal direction to interact with an annular camming surface 735b which is formed adjacent the distal end of body portion 704. When the surgical apparatus 700 is operated to sequentially eject fasteners from the cartridge 737, coupling shaft 735 is drawn in a proximal direction, causing the distal end portion 735a thereof to move radially inward and engage adaptor 730, as shown in FIG. 62c. Adaptor 730 is then drawn proximally by coupling shaft 735 to actuate the cam driver 740 and sequentially eject fasteners from cartridge 737.

Referring to FIGS. 58 and 59, the staple ejecting assembly includes a cam driver 740 which serves to drive a plurality of spaced apart cam members, i.e. cam members 742. The cam members are disposed within, and translate along, a plurality of tracks defined in the staple containing cartridge 737 (see generally FIG. 18). Cam members 742 are dimensioned and configured to effect the sequential ejection of a plurality of surgical staples from the staple containing cartridge 737 as a result of their travel from an initial distal position to a final proximal position. The staple ejecting assembly further comprises a knife blade 744 mounted upon a shank 746 which is adapted to translate with and behind cam members 742 during a stapling operation to divide the stapled tissue. The ejection of staples from the cartridge is accomplished much in the same way as that which has been described hereinabove with respect to previous embodiments of the subject invention. However, as described herein, cam members 742 translate from a distal to a proximal direction to sequentially drive the staples from the cartridge.

In operation, the sequential ejection of a plurality of surgical staples from the staple containing cartridge 737 is effectuated by depressing trigger 731. Movement of trigger 731 will cause gas to be released from supply container 722 which will exert pressure upon the elliptical piston head 727, urging piston 724 in a proximal direction. As piston 724 translates proximally, return spring 726 is compressed, and actuation rod 728 is drawn proximally therewith. As a result, draw bar 732 is pulled proximally within the elongated portion 704 of surgical instrument 700. The proximal translation of draw bar 732 causes the cam members 742 to travel in proximal direction within the tracks which are defined in the staple containing cartridge 737. Once the cam bars have completed their proximal-to-distal translation through the staple-containing cartridge 737, the pressurized cylinder 725 vents through a plurality of circumferentially disposed apertures 747, thereby permitting compressed return spring 726 to drive piston 724 distally into its initial pre-fired position. The distal movement of actuation rod 728 in response to decompression of return spring 726 causes cartridge adaptor 730 to return cam members 732 distally through staple-containing cartridge 737. However, knife blade 744 preferably remains in its proximal-most position by disengaging from the staple firing mechanism, e.g., by becoming lodged in a plastic knife block at the proximal end of the knife blade's travel path through staple-containing cartridge 737.

Referring to FIGS. 55 and 56, handle assembly 702 further comprises an actuation lever 750 for controlling the approximation of the cartridge assembly 712 and the anvil member 715. Actuation lever 750 is operatively connected to an approximation cable 754 which extends through the body portion 704 of surgical instrument 700 to an approximation link 755 associated with the fastener applying assembly 706. The distal end 756 of cable 754 is terminated in a universal ball joint fitting 758 which is maintained within a cavity 760 defined within approximation link 755. The entryway to cavity 760 is tapered to accommodate the angular bending of cable 754 during approximation.

Approximation link 755 is normally biased into the position shown in FIG. 58 so as to maintain the cartridge assembly 712 and anvil member 715 in an open position. This may be accomplished by known biasing structure including, for example, a leaf, compression or torsion spring. Approximation link 755 is pivotably associated with cartridge assembly 712 through a transverse pivot pin 762, and it is associated with the anvil member 715 through a cam pin 764. Cam pin 764 is dimensioned and configured to cooperate with a cam slot 766 which is defined within articulator link 755. To approximate the cartridge housing 712 toward the anvil member 715 to engage tissue therebetween, lever 750 is moved from the position shown in FIG. 55 to that of FIG. 56, causing approximation cable 752 to be drawn proximally. As approximation cable 752 is drawn proximally, link 755 will rotate about pivot pin 762 in a clockwise direction, urging cam pin 764 to move through an arcuate path under the influence of cam slot 766, thereby approximating cartridge assembly 712 and anvil member 715.

Turning now to FIGS. 61 and 63, in conjunction with FIG. 53, the mechanism for effectuating the articulated movement of the fastener applying assembly 706 relative to the elongated portion 704 of surgical instrument 700 includes a planetary gear assembly 770. Planetary gear assembly 770 is operatively connected to the base portion 710 of fastener applying assembly 706 by means of an offset elongated transmission link 772 which extends through body portion 704. As illustrated in FIG. 61, the planetary gear assembly 770 is associated with knob 716 and includes an outer ring gear 774, an internal gear 776 which rotates about a fixed axis in response to the rotation of outer ring gear 774, and a worm gear 778. Worm gear 778 extends through the center of the internal gear 776 and translates longitudinally in response to rotation of internal gear 776. Worm gear 778 is operatively connected to the proximal end of the elongated transmission link 772. The distal end of transmission link 772 is pivotably connected to the base portion 710 of fastener applying assembly 706 by means of pivot pin 780. Thus, in operation, rotation of knob 716 in the direction indicated by arrow "A" in FIG. 53 will cause corresponding longitudinal translation of offset link 722, articulating the fastener applying assembly 706 within an angular sector of rotation, i.e. within a 45° sector of rotation with respect to the longitudinal axis defined by the elongated body 704 as indicated by arrow "A'" in FIG. 53 to increase the range of operability of the apparatus of the subject invention. Although the surgical instrument 700 is shown with a base portion articulatable in only a singular radial direction, it is well within the scope of the present invention to provide for a base portion capable of articulation in symmetric radial directions as shown in the preceding embodiments.

Referring now to FIGS. 60, 63, and 64, in conjunction with FIG. 54, the mechanism for effectuating the independent rotation of the cartridge assembly 712 together with the anvil member 715 relative to the base portion 710 of the fastener applying assembly 706 includes proximal and distal planetary gear assemblies 782 and 784. The proximal planetary gear assembly 782 is interconnected to the distal planetary gear assembly 784 by means of an offset elongated transmission axle 786. Proximal planetary gear assembly 782 is associated with the distalmost control knob 718 on elongated body portion 704 and is illustrated in FIG. 60. Gear assembly 782 includes an outer ring gear 788 which rotates in response to rotation of knob 718, and an internal gear 790 which is configured to rotate about a fixed axis in response to the rotation of outer ring gear 788. The proximal end of transmission axle 786, which preferably has a hexagonal cross-section, is axially mounted within the internal gear 790 and is configured to rotate therewith in response to rotation of knob 718.

The distal planetary gear assembly 784, which is illustrated in FIG. 64, is associated with the base portion 710 of fastener applying assembly 706 and includes an outer pinion gear 792. Pinion gear 792 is configured to rotate in response to the rotation of transmission axle 786. More particularly, the outer pinion gear 792 is mounted to transmission axial 786 by means of a flexible coupling rod 794 which may be fabricated from a pseudoelastic material such as, for example, TINEL material. Other types of rotational drive structure are also contemplated and are within the scope of the invention. These include, for example, universal joints, reinforced flex cabling, etc. The proximal end of coupling rod 794 is mounted in the distal end of the transmission axle 786, and the distal end thereof is mounted to a fitting 796 which is operatively associated with outer pinion gear 792. The distal planetary gear assembly 784 further includes an internal ring gear 798 which is configured to rotate in response to the rotation of pinion gear 792.

As best seen in FIG. 63, the proximal end of the cartridge assembly 712 defines an adapter fitting 800, which is dimensioned and configured to mount operatively within the internal ring gear 798 of the distal planetary gear assembly 784 so as to effectuate the independent rotation thereof relative to the base portion 710 of fastener applying assembly 706. Thus, in operation, rotation of the distal knob 718 in the direction indicated by arrow "B" in FIG. 54 will cause corresponding rotation of transmission axial 786, which, in turn, will rotate the flexible coupling rod 794. In response, the outer pinion gear 792 will rotate, causing the internal ring gear 798 to rotate along with cartridge assembly 712 in the direction indicated by arrow "B'" in FIG. 54. Furthermore, since the anvil 715 is mounted adjacent the cartridge housing 712 it will rotate therewith so as to further increase the range of operability of the surgical apparatus of the subject invention.

Figure 65:
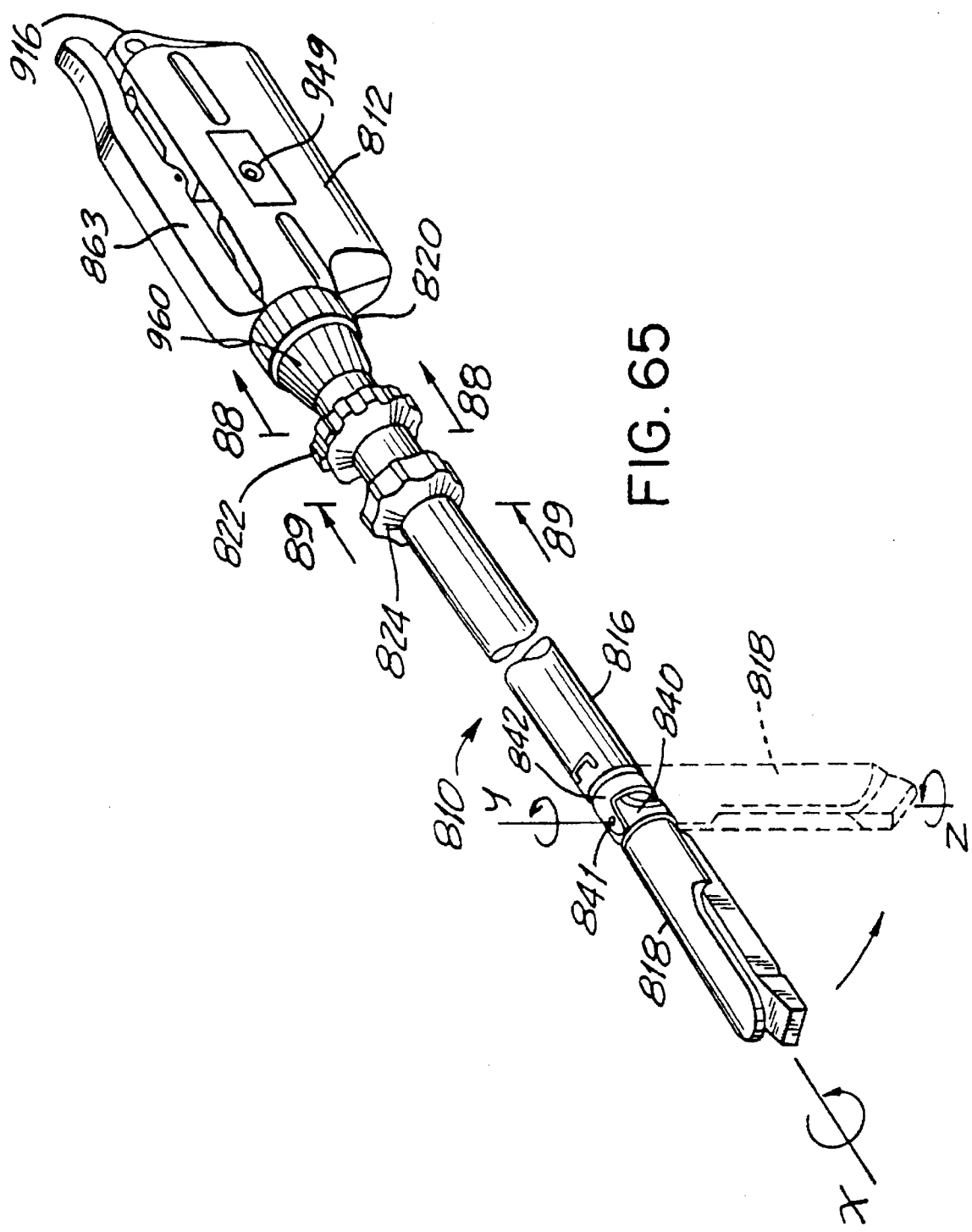
FIG. 65 is a perspective view of another self-contained gas powered articulable surgical apparatus constructed in accordance with a preferred embodiment of the subject invention.

Referring to FIG. 65, another gas powered surgical apparatus constructed in accordance with a preferred embodiment of the subject invention is illustrated and is designated generally by reference numeral 810. Surgical apparatus 810, like the surgical apparatus 700 described hereinabove, is configured to provide the surgeon with an increased range of operability during the performance of an endoscopic or laparoscopic surgical procedure. In brief, surgical apparatus 810 comprises a frame 812 which houses a pneumatic actuation assembly 814 (see generally, FIG. 75), an elongated body 816 which extends from the frame 812 and which defines a longitudinal axis, and a fastener applying assembly 818 which is pivotally associated with a distal end of the elongated body 816.

The surgical apparatus 810 includes three movement control mechanisms for effectuating distinct movements of the fastener applying assembly 818. These mechanisms include a rotation control collar 820 for controlling rotation of the fastener applying assembly 818 about the longitudinal axis defined by the elongated body 816 relative to frame 812 (i.e., rotation about the x-axis), an articulation control wheel 822 for controlling pivotal movement of the fastener applying assembly 818 relative to the distal end of the elongated body 816 (i.e., rotation about the y-axis), and a control wheel 824 for effecting the independent rotation of the fastener applying assembly 818 about a longitudinal axis extending therethrough (i.e., rotation about the z-axis). Each of these movement controlling mechanisms will be described in greater detail hereinbelow.

Figure 66:
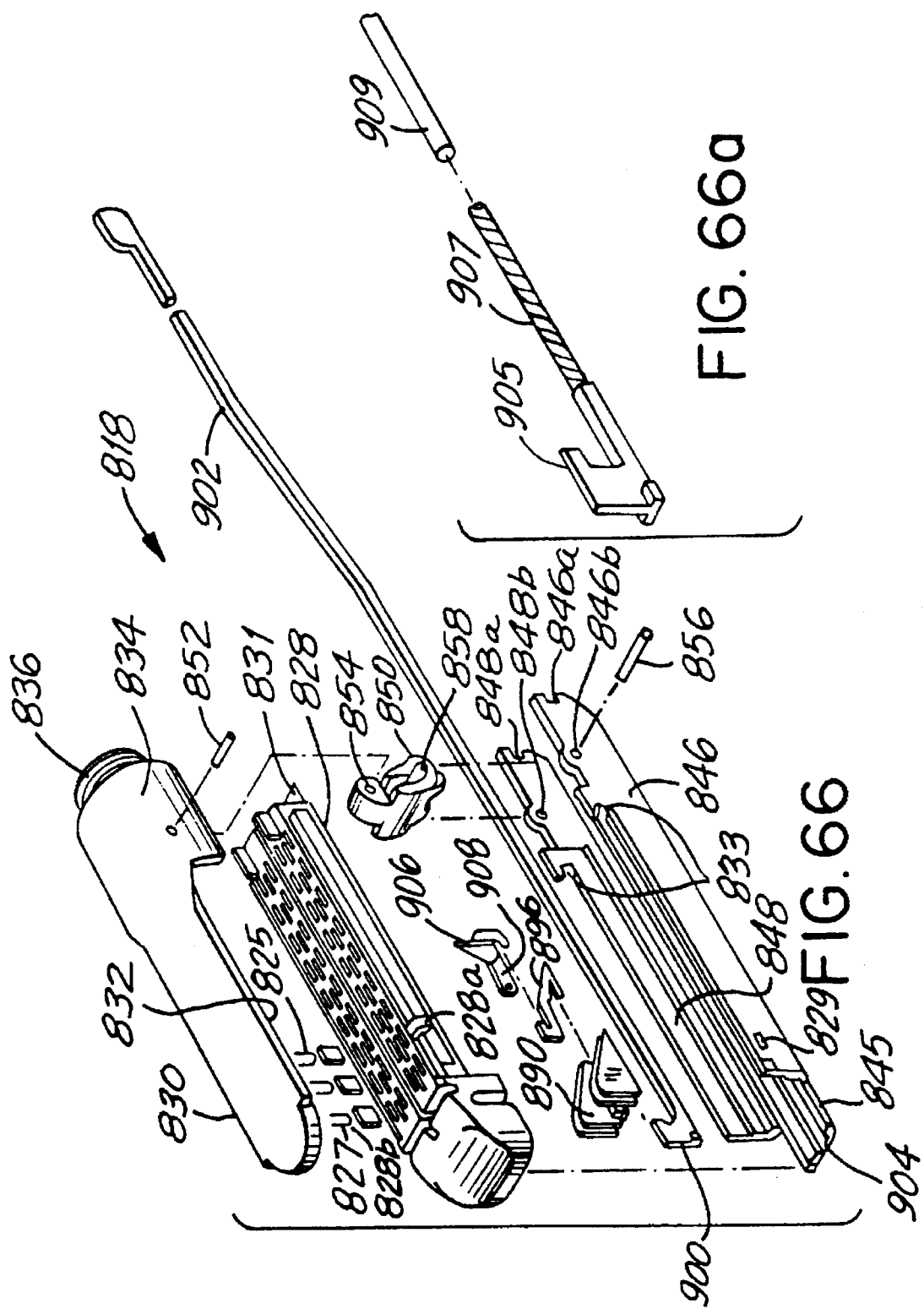
FIG. 66 is an exploded perspective view of the fastener applying assembly of the gas powered surgical apparatus illustrated in FIG. 65.

Referring now to FIG. 66, the fastener applying assembly 818 of surgical apparatus 810 includes a cartridge housing 826 configured to receive a replaceable cartridge 828 which contains a plurality of surgical fasteners 825 and a plurality of corresponding staple pushers 827. The fastener applying assembly 818 further includes an anvil 830 against which the surgical fasteners 825 are driven when they are ejected from cartridge 828.

The replaceable cartridge 828 includes a pair of outwardly extending engaging U-shaped ears 828a and 828b which interact with corresponding apertures 829 formed in the side walls of the cartridge housing 826 to releasably secure the cartridge 828 within the cartridge housing 826. Cartridge also includes a proximal triangular extension 831 that is adapted to slide within slots 833 formed in cartridge housing 826. When loading cartridge 828 into cartridge housing 826, cartridge 828 may be angularly oriented with respect to cartridge housing 826, e.g., at a 30 to 45 degree angle, with extension 831 positioned within slots 833, and then cartridge 828 may be rotated down such that U-shaped ears 828a, 828b engage apertures 829, thereby firmly seating cartridge 828 in cartridge housing 826. Anvil 830 includes a staple forming portion 832 and an anvil mounting portion 834. The mounting portion 834 includes a rearwardly extending annular flange 836 which is dimensioned and configured for rotational engagement within a correspondingly dimensioned and configured annular groove 838 which is defined in the articulated knuckle 840 of surgical apparatus 810 (see generally, FIG. 71). The flange and groove connection which is maintained between the anvil 830 and the knuckle 840 may be further facilitated by the provision of a plurality of radially spaced apart guide pins which extend into the annular groove 838 from the flange 836, or by providing a race of ball bearings which would be disposed within the annular groove 838 to reduce friction as the annular flange rotates within the groove 838.

Referring to FIGS. 65, 66 and 72, the articulated knuckle 840 is pivotally mounted upon a main pivot pin 841 which is maintained within a yoke 842 provided at the distal end of the elongated body 816. Yoke 842 facilitates pivotal movement of the fastener applying assembly 818 in response to the operation of the articulation control wheel 822.

Figure 71:
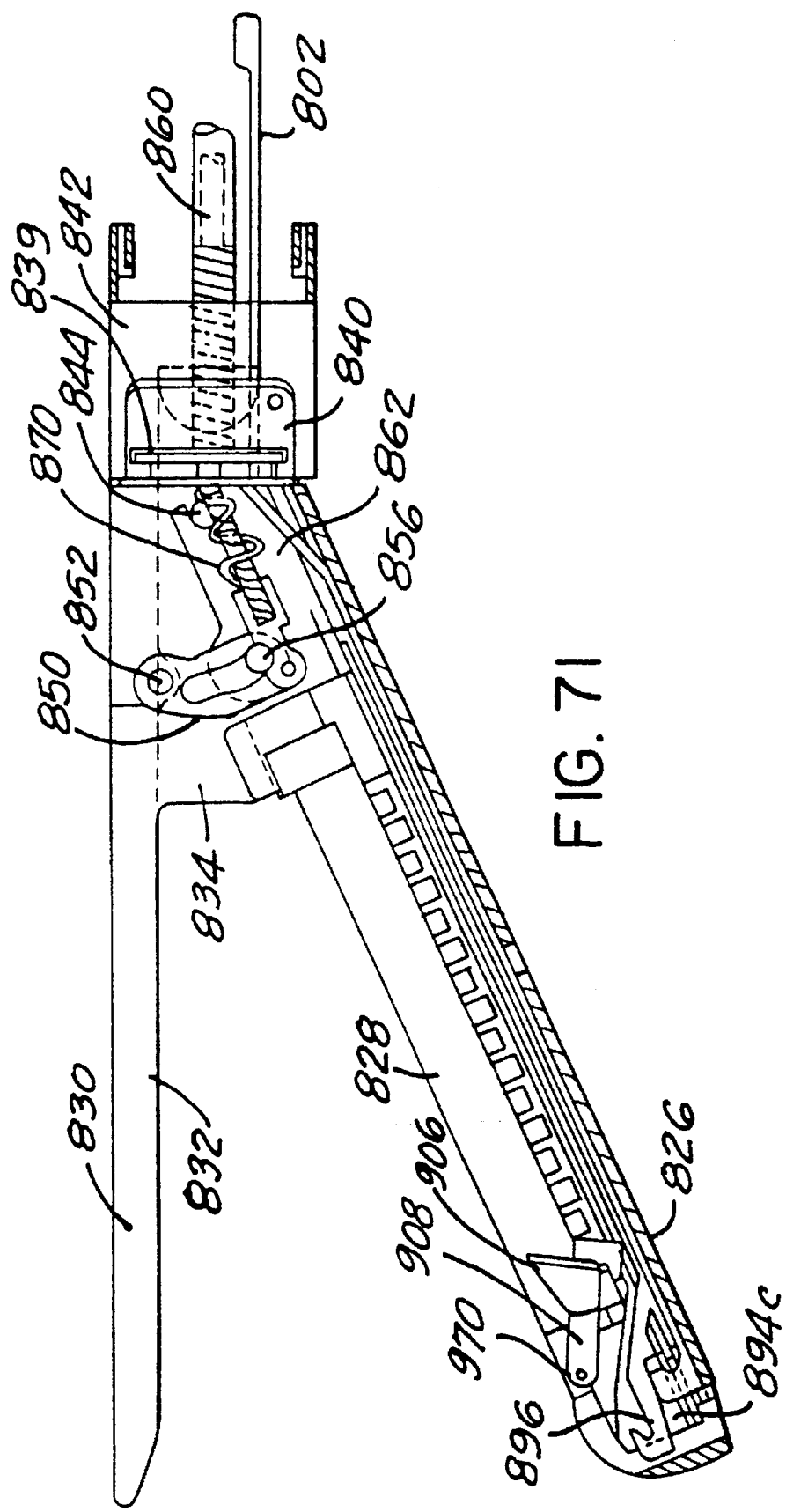
FIG. 71 is a side elevational view in cross-section of the fastener applying assembly of the gas powered surgical apparatus illustrated in FIG. 65 with the cartridge assembly thereof disposed in an open position.

With continued reference to FIGS. 66 and 71, engaging stems such as stem 844 are formed within the mounting portion 834 of anvil 830 for facilitating the engagement of the cartridge housing 826 and the anvil 830 (see, for example, FIG. 71). More particularly, the proximal ends of the side walls 846 and 848 of cartridge housing 826 are provided with notches 846a and 848a, respectively, for engaging the stem 844. Once engaged, the stems enable relative pivotal movement of the cartridge housing 826 and the anvil 830.

Figure 69:
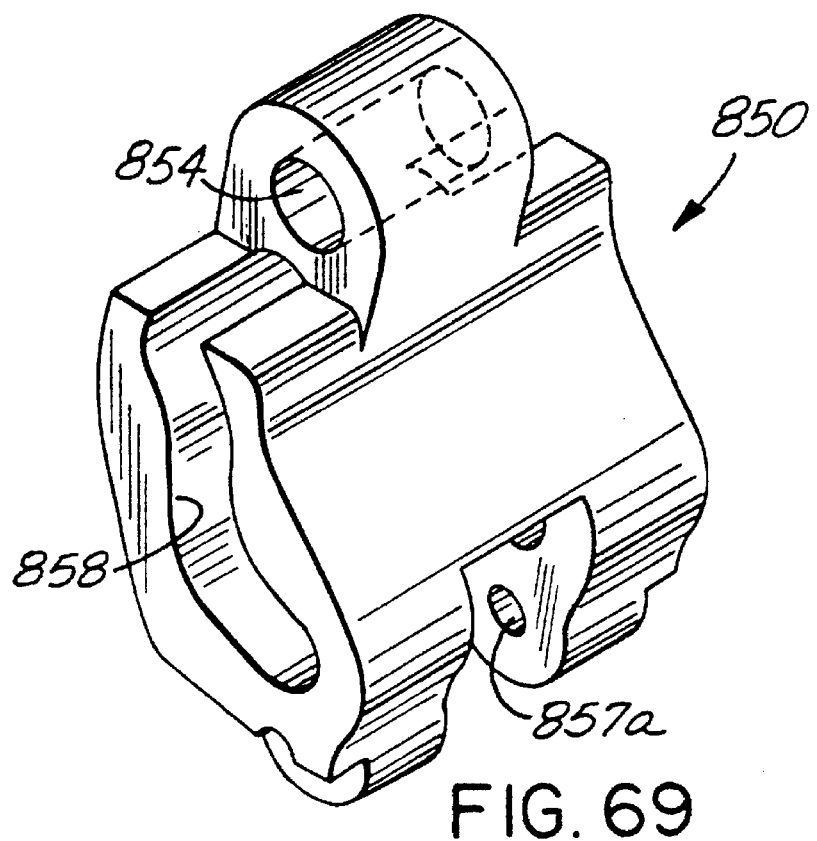
FIG. 69 is an enlarged perspective view of a rotary cam which defines a portion of the fastener applying assembly illustrated in FIG. 66.
Figure 70:
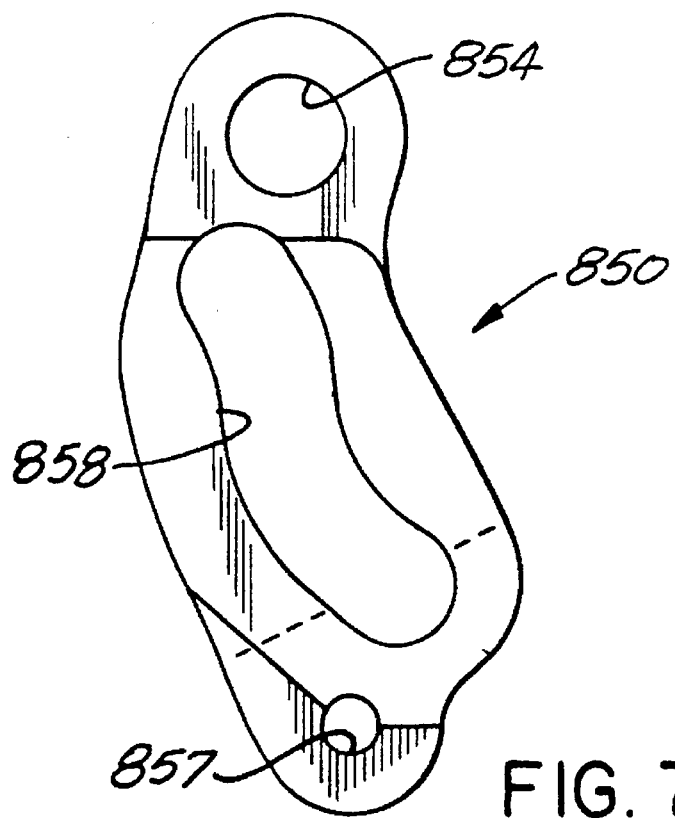
FIG. 70 is a side elevational view of the rotary cam illustrated in FIG. 69.

Referring to FIGS. 66 and 69–71, the cartridge housing 826 and the anvil 830 are operatively interconnected by a unique rotary cam member 850 which is configured to effect the relative movement of the cartridge housing 826 and the anvil 830 during a surgical procedure. More particularly, the rotary cam member 850, which is illustrated specifically in FIGS. 69 and 70, is pivotably mounted to anvil member 830 by a pin 852 (FIG. 66) which extends through aperture 854 in rotary cam 850. A cam pin 856, extending through a circuitous cam slot 858, mounts the cartridge housing 826 to the rotary cam 850 through apertures 846b and 848b, thereby operatively interconnecting the anvil 830 and the cartridge housing 826.

Referring to FIGS. 71 and 72, to effect the relative movement of the anvil 830 and the cartridge housing 826, an actuation cable 860 is connected to rotary cam 850 by a yoke 862 through apertures 857a and 857b. Actuation cable 860 extends through the elongated body 816 of surgical apparatus 810 and is connected to an approximation shaft 866, the movement of which is controlled by approximation handle 868 which is pivotably associated with frame 812 (see generally FIGS. 75 and 76). In use, closure of the approximation handle 868 toward frame 812 will cause proximal movement of the approximation shaft 866 and actuation cable 860. As a result, the rotary cam 850 will be drawn in a generally proximal direction, effectuating the counter-clockwise rotation of the rotary cam 850 about pivot pin 852. Consequently, the cam pin 856 will translate relative to cam slot 858, from the position illustrated in FIG. 71 to that illustrated in FIG. 72, thereby causing the approximation of the cartridge housing 826 and the anvil 830.

Figure 71A:
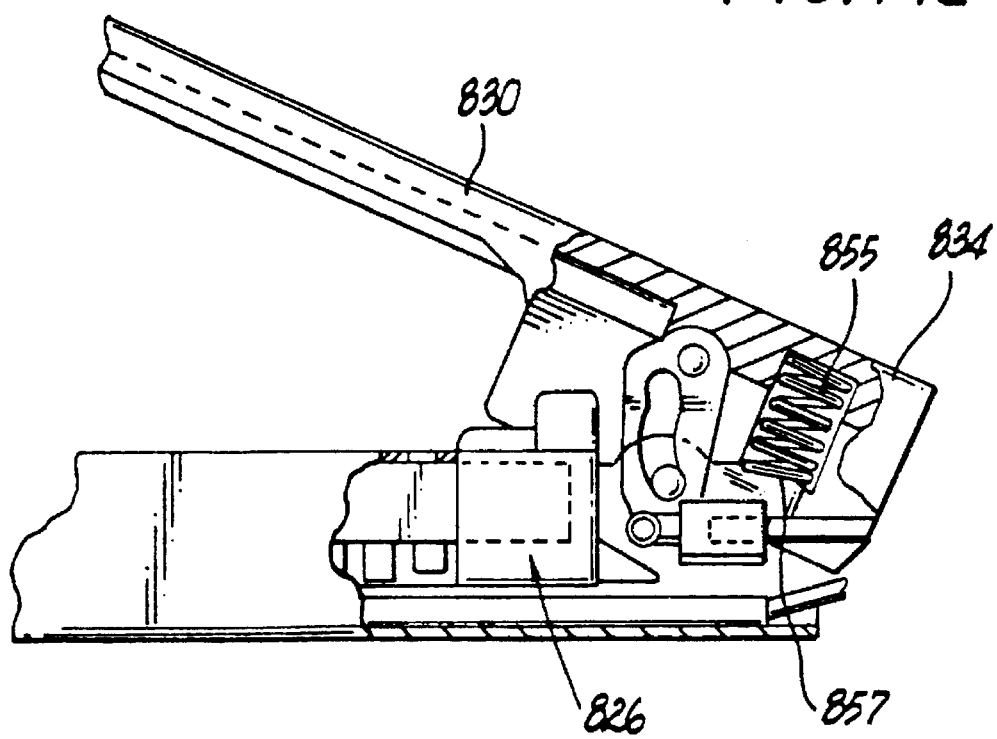
FIGS. 71a and 71b are side elevational views in cross section of the fastener applying assembly in the open and closed positions, respectively
Figure 71B:
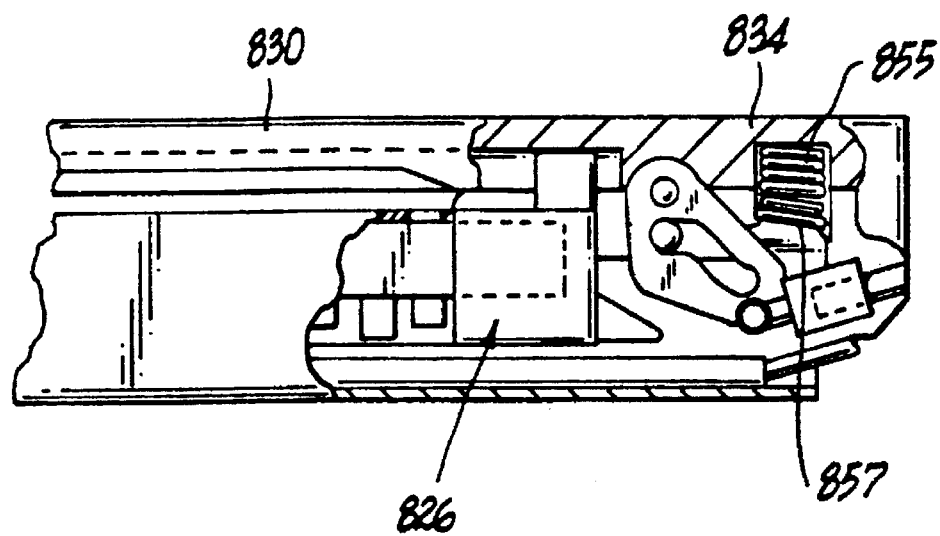
Figure 75:
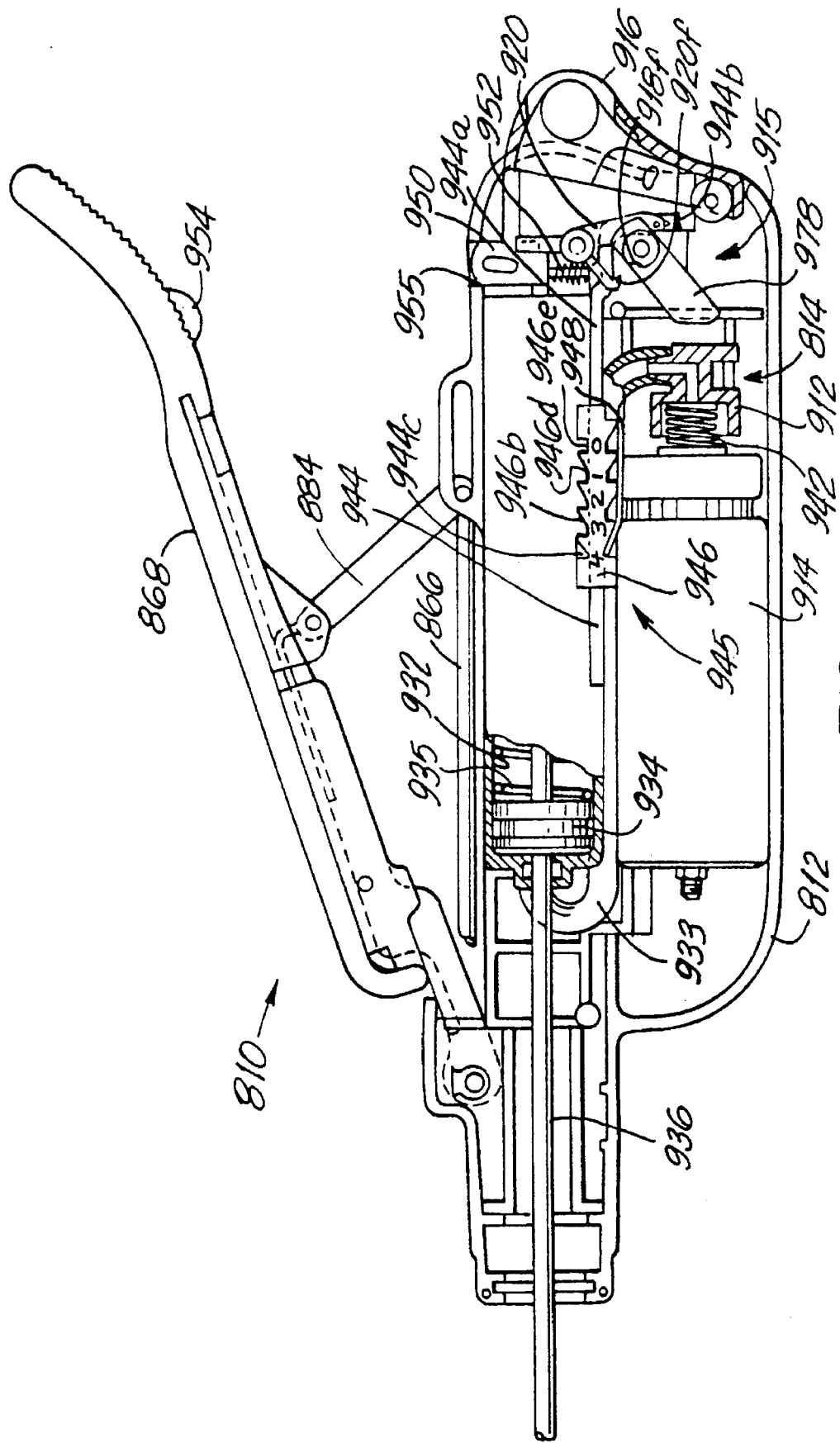
FIG. 75 is a side elevational view in cross-section of the frame portion of the surgical apparatus illustrated in FIG. 65 with the piston in a prefired position within the compression chamber before the surgical apparatus is actuated.

To return the cartridge housing 826 to an open position, approximation handle 868 is pivoted away from frame 812 to the position shown in FIG. 75, thereby urging the approximation shaft 866 in a distal direction. As a result, the tension exerted on actuation cable 860 is relieved, and a coiled spring 870 which is disposed proximal to yoke 862, urges the yoke 862 in a generally distal direction, causing the rotary cam 850 to pivot in a clockwise direction about pin 852. Consequently, cam pin 856 will return to the position illustrated in FIG. 71, and the fastener applying assembly 818 will be in an open position. If desired and as shown in FIGS. 71a and 71b, one or more spring members, e.g., coil spring 855, may be anchored within anvil mounting portion 834 to bias the fastener applying assembly 818 into the open position. The coil spring 855 engages a spring plate 857 on fastener applying assembly 818 and is compressed, as shown in FIG. 71b, when anvil 830 and cartridge housing 826 are approximated. When in the open position, coil spring 855 assumes a non-compressed configuration, as shown in FIG. 71a.

Referring to FIGS. 86a and 86b, an alternative embodiment of an approximation shaft for effecting the longitudinal movement of actuation cable 860 in response to pivotal movement of approximation handle 868 is illustrated and is designated generally by reference numeral 872. Approximation shaft 872 is slidably associated with frame 812 and includes a distal mounting portion 874 for engaging a coupling 876 to which actuation cable 860 is mounted. An adjustment screw 878 for adjusting the tension imparted upon actuation cable 860 is disposed in the proximal portion 880 of approximation shaft 872. The adjustment screw 878 is formed with a transverse mounting pin 882 for connecting the screw 878 to the handle link 884 which interconnects the approximation handle 868 and the frame 812. In use, movement of the handle 868 toward and away from the frame 812 will cause corresponding proximal and distal movement of approximation shaft 872.

Figure 67:
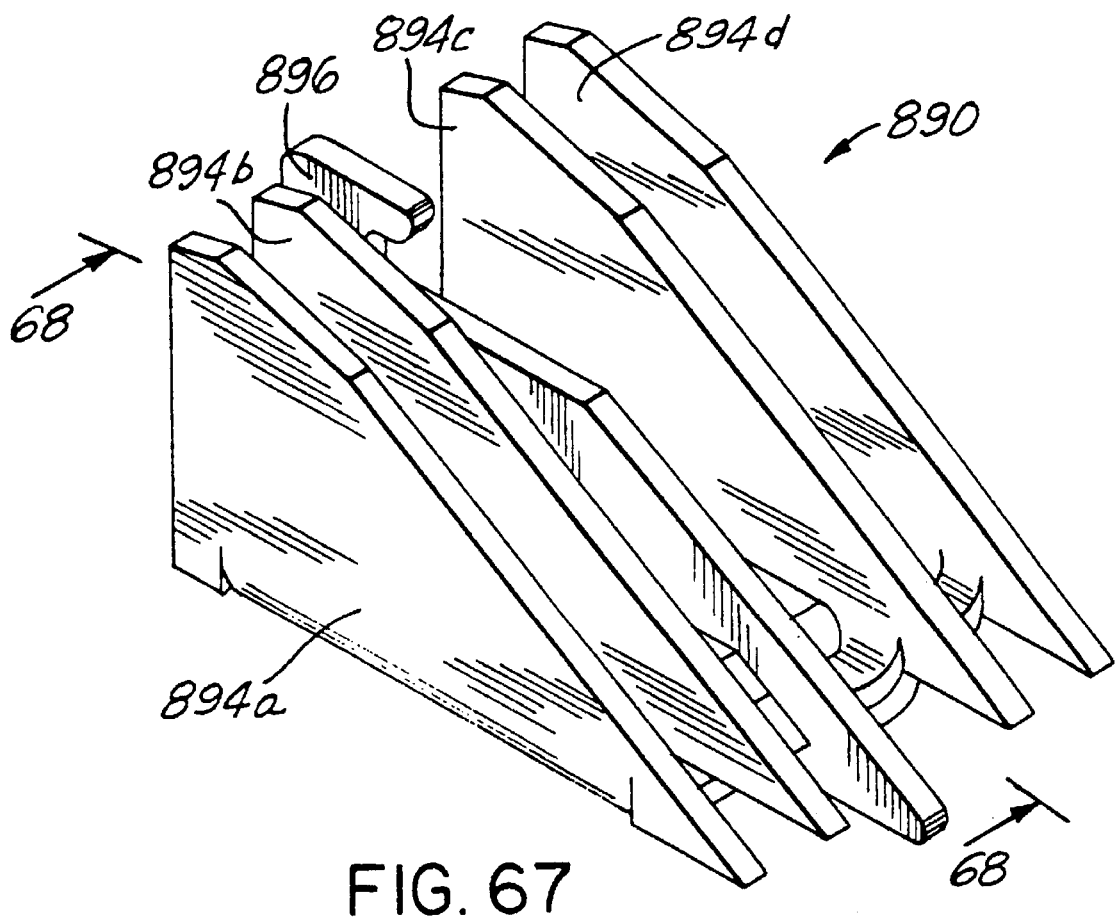
FIG. 67 is an enlarged perspective view of the cam sled which defines a portion of the fastener applying assembly illustrated in FIG. 66.
Figure 68:
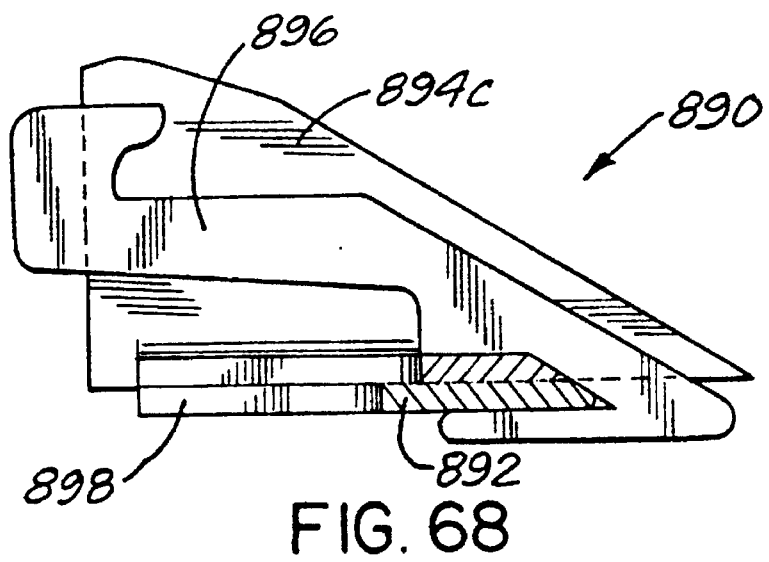
FIG. 68 is a cross-sectional view taken along line 68—68 of FIG. 67.

Referring again to FIG. 66, the fastener applying assembly 818 includes a unique fastener ejection mechanism for sequentially ejecting a plurality of surgical fasteners 825 from the cartridge 828 during a surgical procedure. The fastener ejection mechanism includes a cam sled 890, illustrated specifically in FIGS. 67 and 68, which comprises a base 892, and a plurality of upstanding cam plates 894a–894d. The base 892 of cam sled 890 includes a notched area 898 for releasably retaining the flanged engaging end 900 of a draw bar 902. An elongated track 904 is formed in the floor 845 of cartridge housing 826 for guiding the translation of draw bar 902 as it is drawn from a distal position to a proximal position when the pneumatic actuation system 814 is operated during a surgical procedure.

The upstanding cam plates 894a–894d of cam sled 890 are configured to sequentially actuate pushers 827 which are disposed within cartridge 828 for urging the fasteners 825 therefrom. [The cam plates may be disposed in a staggered configuration to balance forces within the cartridge as the fasteners are sequentially ejected therefrom.] The cam plates 894a–894b translate within corresponding longitudinal slots (see generally, FIG. 18) which are formed in the cartridge 828 and communicate with the pushers 827. An engaging arm 896 depends from the base 892 of cam sled 890 between cam plates 894b and 894c. This arm 896 engages a knife member 906 as the cam sled 890 translates from the distal end of cartridge 828 to the proximal end thereof for forming an incision in tissue as fasteners 825 are applied thereto. As best seen in FIG. 71, the knife member 906 is positioned on a shank 908 mounted by a frangible shear pin 910 adjacent the distal end of cartridge 828. Initially, as illustrated in FIG. 72, the shank 908 is pivoted into a recessed position to facilitate the engagement thereof by engaging arm 896 as the cam sled 890 translates proximally.

Referring to FIGS. 72–74, in operation, the cam sled 890 is drawn proximally by the draw bar 902 under the influence of the pneumatic actuation assembly 814. A downwardly extension hook portion 908a of shank 908 is subsequently engaged by arm 896 as shown in FIG. 73. Concomitantly, the driving forces produced by the pneumatic actuation assembly 814 effectively operate to break shear pin 910 and release the knife member 906, whereupon the camming sled 890 and the knife member 906 translate as an integral unit to the proximal end portion of cartridge 828, as illustrated in FIG. 74.

After the fasteners 825 have been driven from cartridge 828, the entire cartridge, along with the cam sled 890 and the knife member 906 may be removed from the cartridge housing 826 and replaced with a new, loaded cartridge. The new cartridge will contain a distally positioned cam sled and frangibly mounted knife member. When the draw bar 902 is returned to its initial distal-most position and a cartridge is placed in the cartridge housing 826, the engaging end 900 of draw bar 902 reacquires the notched area 898 provided in the base 892 of cam slide 890 and the apparatus 810 is once again prepared for operation.

In an alternative embodiment of the subject invention which is illustrated in FIG. 66a, the cam sled 890 is releasably engaged by a flanged fixture 905 which is mounted at the distal end of a drive cable 907. Drive cable 907 extends through the elongated body 816 of surgical apparatus 810 to the frame 812 where it operatively interconnects with the pneumatic actuation assembly 814. A reinforcing tube 909 is placed around drive cable 907 to impart rigidity thereto, particularly for the return stroke of drive cable 907 through cartridge housing 826. Reinforcing tube 907 is preferably fabricated from a pseudoelastic material, e.g., a nickel-titanium alloy such as Tinel, which is available from Raychem, Inc., Menlo Park, Calif.

Figure 76:
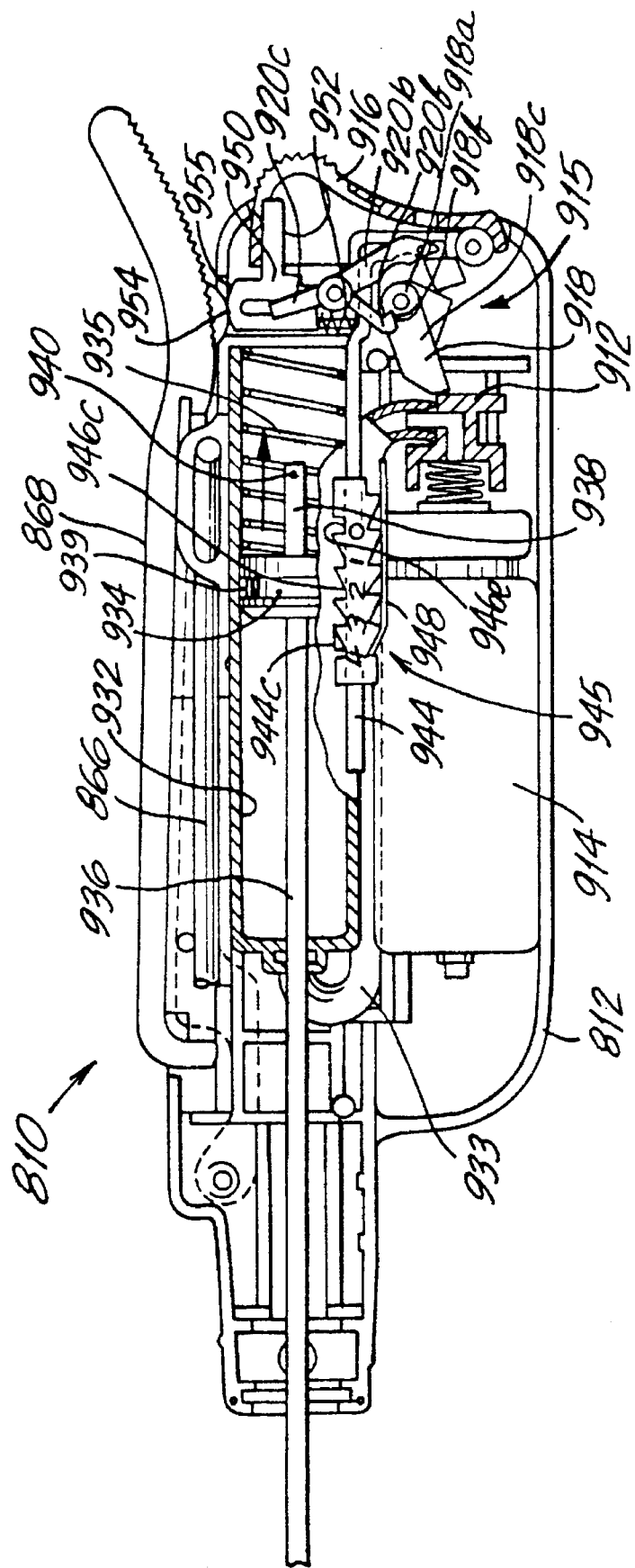
FIG. 76 is a side elevational view in cross-section of the frame portion of the surgical apparatus illustrated in FIG. 65 with the piston moved partially through the compression chamber.
Figure 77:
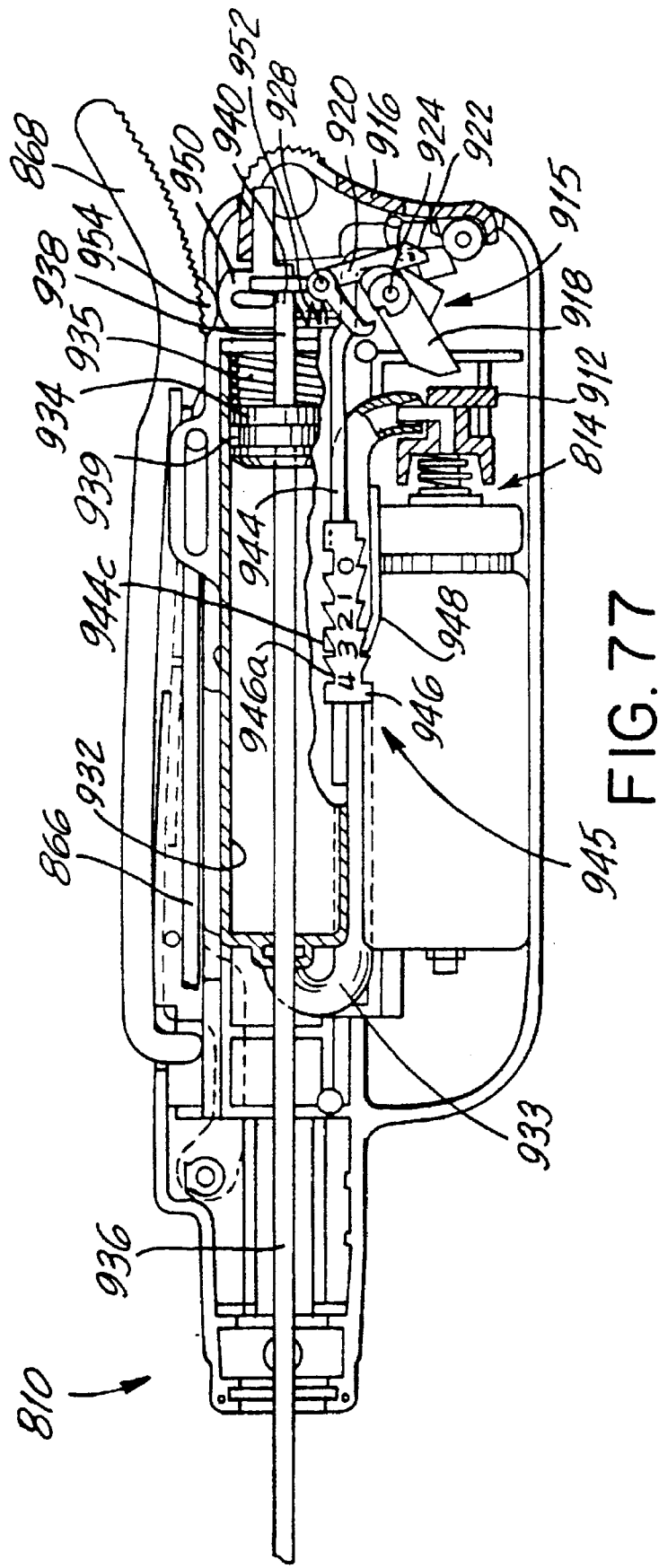
FIG. 77 is a side elevational view in cross-section of the frame portion of the apparatus illustrated in FIG. 76 with the piston advanced through the compression chamber to disengage the firing control mechanism and index the counter assembly of the subject invention.

Referring to FIGS. 75–77, there is illustrated the pneumatic actuation assembly 814 which is disposed within the frame 812 of surgical apparatus 810 for effectuating the sequential ejection of a plurality of surgical fasteners 825 from cartridge 828. Pneumatic actuation assembly 814 differs from the pneumatic actuation systems which are provided in the previously described embodiments of the subject invention in that the valve 912 is configured to move relative to a stationary gas supply container 914 to cause gas to be released therefrom.

Referring to FIGS. 75–85, a unique firing control mechanism 915 is provided for effecting the controlled movement of valve 912 with respect to gas supply container 914. In brief, the firing control mechanism 915 includes a trigger 916, a rocker link 918, and a latching link 920.

Trigger 916 includes a firing block 922 which is positioned to interact with rocker link 918 when the trigger 916 is depressed by the user. Rocker link 918, which is specifically illustrated in FIGS. 81–84, is mounted upon a transverse shaft 924 and is biased into a prefired position by a coiled biasing spring 926 (see, FIG. 85). Biasing spring 926 serves to bias rocker link 918 against rotational movement as well as lateral movement with respect to transverse shaft 924. Rocker link 918 is defined by a central body portion 918a, a thrust portion 918b, and a pusher portion 918c which is configured to be urged against the valve 912 to move the valve toward the gas supply container 914 during actuation of the instrument. The body portion 918a of rocker link 918 defines an angled camming surface 918d for interacting with the latching link 920.

Figure 85:
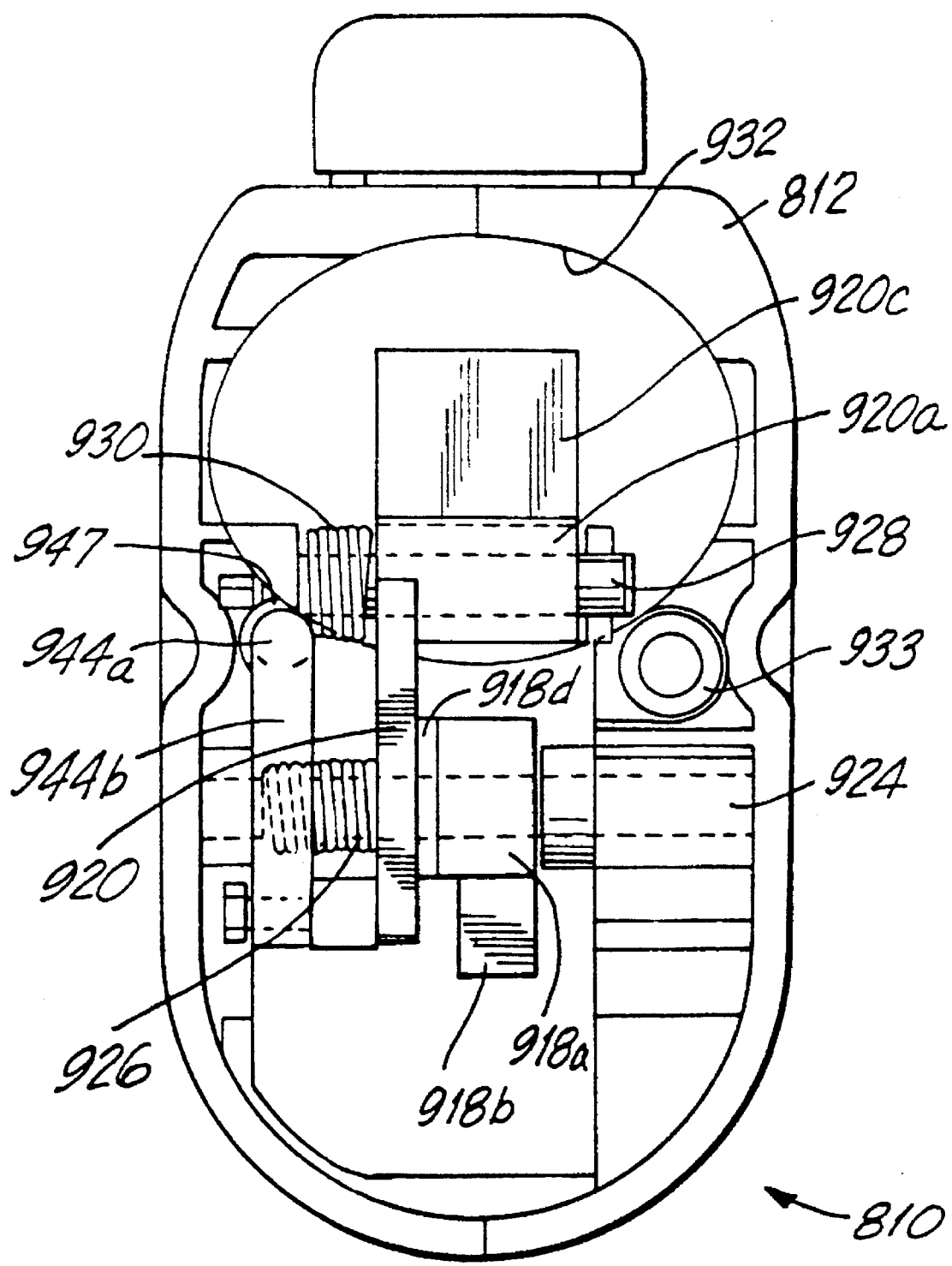
FIG. 85 s an elevational view in cross-section of the proximal end of the frame portion of the gas powered surgical apparatus of FIG. 65 illustrating the firing control linkage.

Latching link 920, specifically illustrated in FIGS. 78–80, is mounted upon a transverse shaft 928 and is biased into a prefired position by a coiled torsion spring 930 (FIG. 85). Latching link 920 includes a central body portion 920a, a camming arm 920b, a latch release plate 920c, and a latch arm 920d. The camming arm 920b is provided with an arcuate notch 920e for interacting with the camming surface 918d of rocker link 918. The latch arm 920d is formed with a tooth 920f for engaging a corresponding notch 918f which is formed in the central body portion 918a of rocker link 918.

Referring to FIG. 76, depression of trigger 916 will urge firing block 922 against the thrust portion 918b of rocker link 918. As a result, rocker link 918 will rotate about transverse shaft 924 in a clockwise direction, against the bias of coiled spring 926 (FIG. 85), and concomitantly, the notch 918f will rotate on camming arm 920b and latch link 920 will pivot in a counter-clockwise direction. As rocker link 918 and latch link 920 continue to rotate in opposed directions, the tooth 920f on latch arm 920d will engage the notch 918f in rocker link 918. Thereupon, the pusher portion 918c of rocker link 918 will be urged against valve 912, pushing the valve 912 toward the gas supply container 914 to expel gas therefrom. Valve 912 will remain urged against gas supply container even if the depressive force is removed from trigger 916.

When gas is expelled from supply container 914, it is transferred through valve 912, and flexible conduit 933, into a distal end of compression chamber 932 wherein a piston 934 is disposed. An elastomeric o-ring 939 is provided to seal piston 934 with respect to compression chamber 932. Preferably, the compression chamber 932 and the piston 934 are designed in a manner to maximize the cross sectional dimensions thereof, based on the available space therefor. For example, compression chamber 932 and piston 934 may each have an elliptical cross-sectional configuration to maximize their respective cross sectional dimensions with respect to a given frame geometry (see FIG. 85). As illustrated in FIGS. 76–77, piston 934 will translate through the compression chamber 932 in a proximal direction as compressed gas is transferred into the chamber 932 from supply container 914.

A drive shaft 936 depends distally from the piston 934 and is operatively connected to a coupling shaft (not shown) which extends through the elongated body 816 to connect with the draw bar 902. A stroke shaft 938 extends proximally from piston 934 and includes a transverse drive'shaft extension 940 which is positioned and dimensioned to interact with the latch release plate 920c of latching link 920 when the piston 934 completes its firing stroke and translates to the proximal end of compression chamber 932.

As best seen in FIG. 77, when the piston 934 reaches its proximal-most position within the compression chamber 932, the drive shaft extension 940 will contact the latch release plate 920c, causing the latching link 920 to pivot clockwise, thereby releasing tooth 920f from notch 918f. As a result, rocker link 918 will pivot in a counter-clockwise direction to permit valve 912 to return to a prefired position under the bias of coil spring 942. In addition, rocker link 918 will move transversely to disengage from the trigger 916, thereby allowing the mechanism to return to its initial position, even if the trigger 916 remains depressed. A coiled return spring 935 is disposed within chamber 932 and is associated with the piston 934 for returning the piston 934 to a distal position at the completion of its firing stroke.

Referring to FIGS. 75 and 77, surgical apparatus 810 includes a unique counter mechanism 945 which is operatively associated with the firing control mechanism 915 described hereinabove. The counter mechanism 945 is configured to visually indicate to the user the number of times the surgical apparatus 810 may be fired and to prevent the operation of the pneumatic actuation assembly 814 after a predetermined number of firing. This effectively prevents the apparatus 810 from being fired when there may be an insufficient quantity of compressed gas contained within gas supply canister 914.

The counter mechanism 945 of the subject invention includes an elongated counter shaft 944 defining a main shaft portion 944a and a downturned proximal portion 944b.

As best seen in FIG. 85, the main shaft portion 944a is maintained in a track 947 formed in the side wall of frame 812 and the proximal portion 944b is connected to the camming arm 920b of latching link 920.

A ratchet tooth 944c depends from the main shaft portion 944a of counter shaft 944 which is configured to operatively interact with a linear rack member 946. Rack member 946 includes four ramped engagement notches 946a–946d and a fifth squared engagement notch 946e. A leaf spring 948 interacts with rack member 946 for sequentially maintaining the rack member 946 in an incremental indexed position. Numerical indicia are imprinted on the outside surface of rack member 946 and are sequentially visible through a windowed porthole 949 provided in the side wall of frame 812 (see, FIG. 65). The numerical indicia correspond to the five engagement notches 946a–946e defined on rack member 946. In particular, notches 948a–948d correspond to the numerals "4-1", respectively, while notch 948e corresponds to the numeral "0". Each numeral identifies the number of times the pneumatic actuation assembly 814 may be actuated to operate surgical apparatus 810. One skilled in the art will readily appreciate that, depending upon the volume of gas needed for actuation, and/or the volume of the supply container, the number of engagement notches formed on rack member 946 can be increased or decreased.

As illustrated in FIG. 75, initially the rachet tooth 944c is disposed in the first ramped engagement notch 948a of rack member 946 (at such a time the numeral "4" will appear in the windowed porthole 949). When the apparatus 810 is operated for the first time, and the firing control mechanism 915 is activated, the counter shaft 944 will be drawn in a proximal direction as the latching link 920 is pivoted in a counter-clockwise direction. As a result, ratchet tooth 944c will move up the ramp of engagement notch 948a and into the second engagement notch 948b, as shown in FIG. 77. When the latching link 920 returns to a prefired position, the counter shaft 944 translates distally, causing the rack member 946 to translate therewith in a distal direction. Consequently, the next numeral will be moved into view of the windowed porthole 949, which, after the first firing, will be the numeral "3", indicating that surgical apparatus 810 may be operated three more times.

When the surgical apparatus 810 is to be operated for the fourth and final time, ratchet tooth 944c will be positioned in the squared engagement notch 948e of rack member 946. When the counter shaft 944 and rack member 946 move distally and are locked forward by leaf spring 948, latching link 920 is also locked forward. As a result, after the fourth operation, the latching link 920 will be inhibited from pivoting into its prefired position under the influence of counter shaft 944 and will stay in the fired position. While maintained in the fired position, the latching link 920 will move the rocker link 918 transversely so as to be able to return to its prefired position. Consequently, when the trigger 916 is subsequently depressed, in an attempt to operate the instrument, the camming surface 918d on rocker link 918 will be unable to interact with the camming arm 920b to effect lateral movement of rocker link 918. Thus, the rocker link 918 will be unable to rotate and, as a result, the surgical apparatus 810 will be rendered inoperative.

Referring again to FIGS. 75 and 76, surgical apparatus 810 further includes a trigger blocking member 950 which is configured to prevent the depression of trigger 916 until such time as the approximation handle 868 is moved into a closed position (see FIG. 76). The trigger blocking member 950 is biased into a blocking position by a coiled spring 952 and is moved out of the blocking position by a detent 954 which depends from handle 868 adjacent the proximal end thereof. The detent 954 is dimensioned and configured to extend through an aperture 955 formed in frame 812 when the approximation handle 868 is moved to a closed position (FIG. 76).

Figure 88:
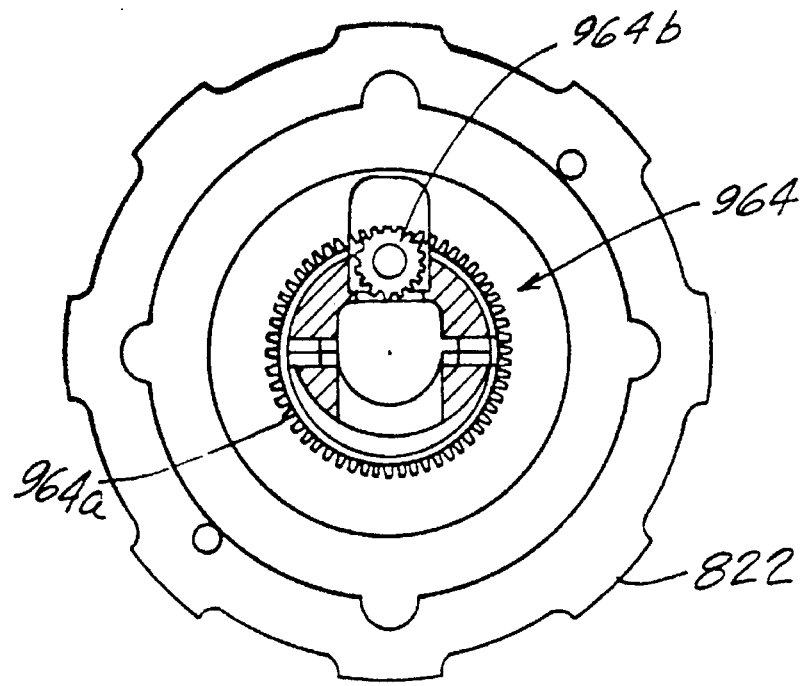
FIG. 88 is a cross-sectional view taken along line 88—88 of FIG. 65 illustrating the articulation control mechanism shown in FIG. 87.
Figure 89:
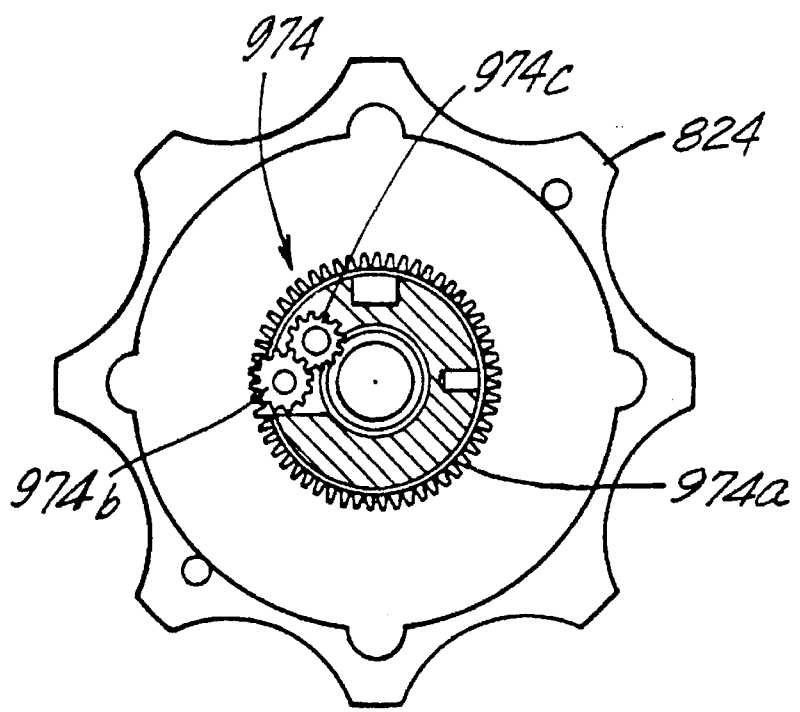
FIG. 89 is a cross-sectional view taken along line 89—89 of FIG. 65 illustrating the rotational control mechanism shown in FIG. 87.

Turning now to FIGS. 87–89 in conjunction with FIG. 65, the movement control mechanisms of the subject invention which are discussed briefly hereinabove are illustrated. The first control mechanism activated by collar 820 is configured to effect axial rotation of the fastener applying assembly 818 about the longitudinal axis defined by the elongated body 816 of surgical apparatus 810 (i.e., about the x-axis). Collar 820 includes a frusto-conical portion 960 which is connected directly to the body 816 such that rotation of the collar 820 effects corresponding axial rotation of the entire body 816 and, consequently, effects axial rotation of the fastener applying assembly 818.

The second mechanism activated by wheel 822 for controlling the articulated movements of the fastener applying assembly 818 (i.e., about the y-axis) is shown in FIGS. 87 and 88, and includes a pinion gear assembly 964 defined by an outer ring gear 964a and an internal pinion gear 964b. The internal pinion gear 964b is formed with a threaded axial bore (not shown) for cooperating with a threaded portion 966a of an elongated articulation shaft 966. The distal end of shaft 966 is pivotably connected to a pivot pin 968 provided in the articulated knuckle 840 of the fastener applying assembly 818. In use, rotation of wheel 822 in one direction will cause the internal pinion gear 964b to rotate in an opposed direction as it is driven by the outer ring gear 964a. Consequently, the threaded portion 966a of articulation shaft 966 will be driven in a longitudinal direction to effect pivotal movements of the fastener applying assembly 818 relative to the body 816 of surgical apparatus 810.

The third control mechanism activated by wheel 824 is configured to effect the independent rotation of the fastener applying assembly 818 (i.e., about the z-axis) is illustrated in FIGS. 87 and 89 and includes a pinon gear assembly 974. Pinion gear assembly 974 includes an outer ring gear 974a and a pair of internal pinion gears 974b and 974c. Pinion gear 974b meshes directly with the outer ring gear 974 and pinion gear 974c meshes with pinion gear 974b. Thus, the directional component of the rotation imparted to wheel 824 by the user will be identical to that which is imparted to pinion gear 974c.

A transition shaft 976 extends from pinon gear 974c, through the elongated body 816 of surgical apparatus 810, to a transmission gear set 978 which is disposed adjacent the distal end of body 816. The transmission gear set 978 serves to translate the directional component of rotation imparted to the transition shaft 976 by pinion gear 974c to a rotator shaft 980 which is disposed in coaxial relationship with the longitudinal axis of the elongated body 816.

The transmission gear set 978 includes a pair of pinion gears 978a and 978b. Pinion gear 978a is connected to the distal end of transition shaft 976 and pinion gear 978b is connected to the proximal end of rotator shaft 980. The distal end portion 980a of rotator shaft 980, is configured in the form of a flexible coupling, and is fixedly mounted within the mounting portion 834 of anvil member 830 (see, for example, FIGS. 72–74). An axial bore extends through the entire rotator shaft 980 to accommodate the passage of the actuation cable 860 which actuates the rotary cam 850 to approximate the cartridge housing 826 and the anvil 830.

Referring to FIG. 87a, an alternative embodiment of the subject invention may also include a rotation transmission assembly 990 having a rotating adapter sleeve 992 disposed in the distal end of the elongated body 816 and mounted to the distal end portion 980a of rotator shaft 980. A pair of flexible rod members 994a and 994b, preferably formed of a shape memory alloy, extend from the adapter sleeve 992 through the articulated knuckle 840 and into the mounting portion 834 of anvil member 830 where they are fixedly secured to the anvil member 830. In use, the directional component of rotation which is imparted to rotator shaft 980 is transferred to the adapter sleeve 992, which, in turn, transfers rotation through the articulated knuckle 840 to the fastener applying assembly 818 to effect the independent rotation thereof.

Figure 90:
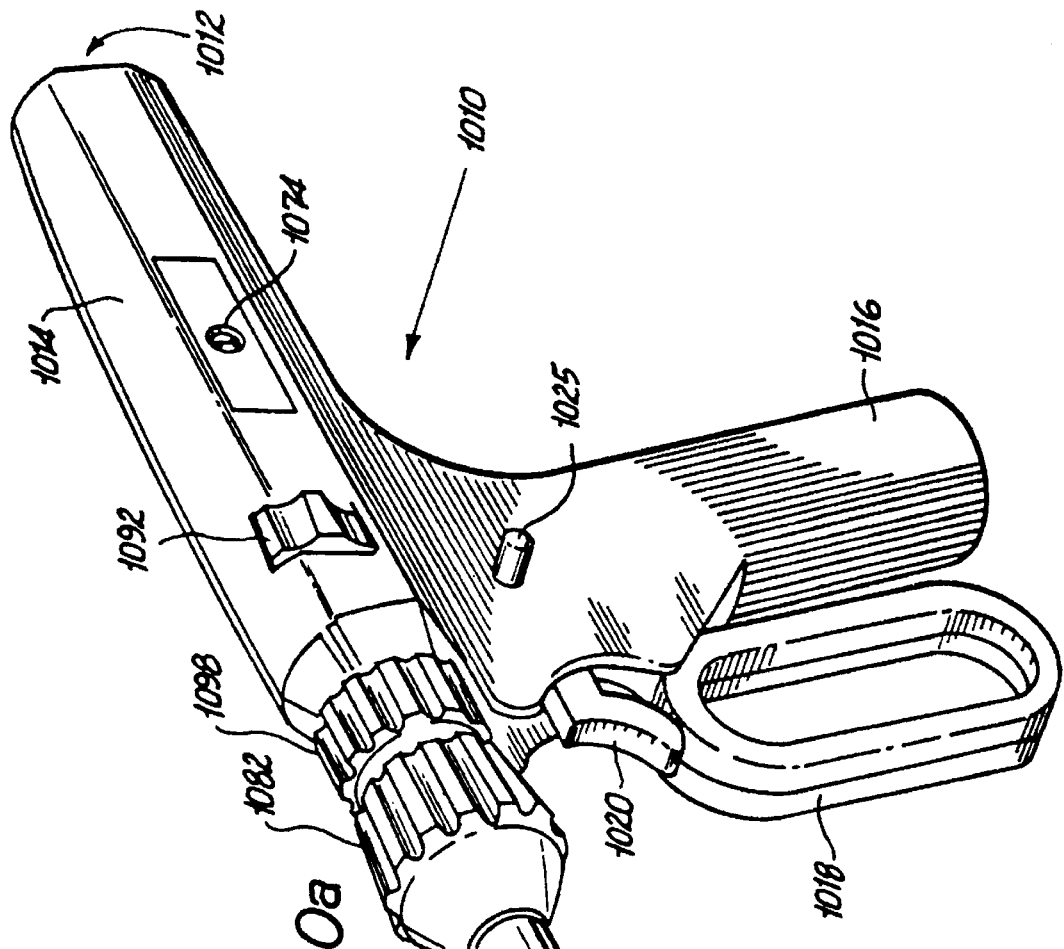
FIG. 90 is another self-contained gas powered surgical apparatus constructed in accordance with a preferred embodiment of the subject invention which includes a pistol-type handle assembly.
Figure 90A:
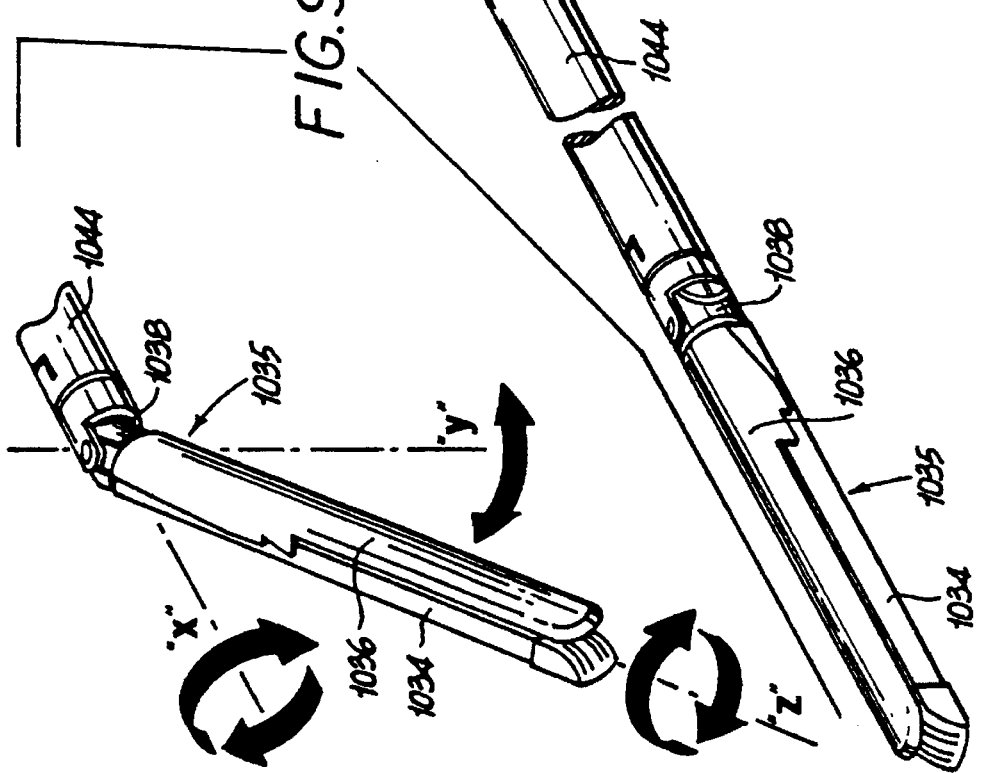
FIG. 90a is a perspective view of the fastener applying assembly of the surgical apparatus illustrated in FIG. 90 disposed in an articulated position with the fastener applying assembly independently rotated in a clockwise direction relative to the elongated body.

Referring to FIGS. 90 and 90a, another surgical apparatus constructed in accordance with a preferred embodiment of the subject invention is illustrated and is designated generally by reference numeral 1010. Surgical apparatus 1010, like the surgical apparatus 810 described hereinabove, is configured to provide the surgeon with an increased range of operability during the performance of an endoscopic or laparoscopic surgical procedure. However, surgical apparatus 1010 differs from each of the instruments described previously herein, in that the handle assembly 1012 thereof has a pistol-like configuration. More particularly, the handle assembly 1012 of surgical apparatus 1010 defines a barrel portion 1014, a stationary hand grip 1016 which depends angularly from the barrel portion 1014 and an actuation handle 1018 which is pivotally associated with the stationary hand grip 1016. A trigger 1020 is slidably associated with the stationary hand grip 1016 of handle assembly 1012 and includes a unique safety mechanism 1025 which is adapted to maintain the trigger 1020 within a recessed area of the stationary hand grip 1016 to preclude user access thereto prior to effecting a proper closure sequence as will be described in greater detail hereinbelow.

Referring to FIG. 91, the barrel portion 1014 of handle assembly 1012 is configured to house an elongated compression chamber 1022 within which a piston 1023 translates when the surgical apparatus 1010 is actuated (see generally FIG. 94). The angularly depending stationary hand grip 1016 of handle assembly 1012 is configured to house a pneumatic actuation assembly 1024 which includes a gas supply canister 1026, a valve 1027 which is movable into communication with the supply canister 1026, and a firing control mechanism 1028 which includes a rocker link 1030 and a cooperating latching link 1032.

The pivoting actuation handle 1018 of handle assembly 1012 is configured to effectuate approximation of the cartridge assembly 1034 and the anvil member 1036. These are each operatively associated with the articulated distal end portion 1038 of surgical apparatus 1010 and which together define the fastener applying assembly 1035 illustrated in FIG. 90. Actuation handle 1018 is operatively connected to a pivot link 1040 which extends to an approximation shaft 1042 disposed within the barrel portion 1014 of handle assembly 1012. Approximation shaft 1042 extends from the handle assembly 1012, into the elongated body 1044 of surgical apparatus 1010, where it interconnects with an approximation cable (i.e. actuation cable 860 of surgical apparatus 810 which is illustrated in FIGS. 71 and 72).

In use, movement of the actuation handle 1018 from the position illustrated in FIG. 91 to that which is illustrated in FIG. 94 will effect the clockwise rotation of pivot link 1040 about pivot pin 1046. As a result, the approximation shaft 1042 will be drawn in a proximal direction and the cartridge assembly 1034 and anvil member 1036 of fastener applying assembly 1035 will be moved into a closed position.

Figure 92:
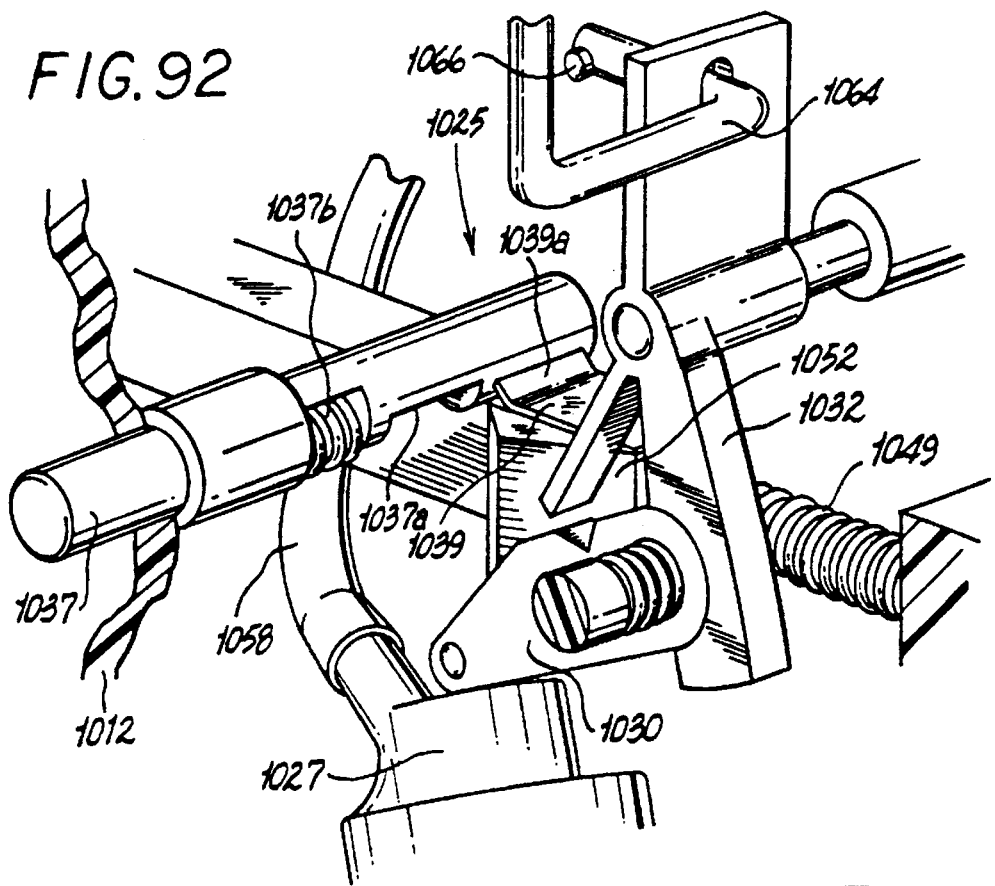
FIG. 92 is an enlarged perspective view of the safety mechanism which is associated with the pneumatic actuation system of the surgical apparatus illustrated in FIG. 90.
Figure 93:
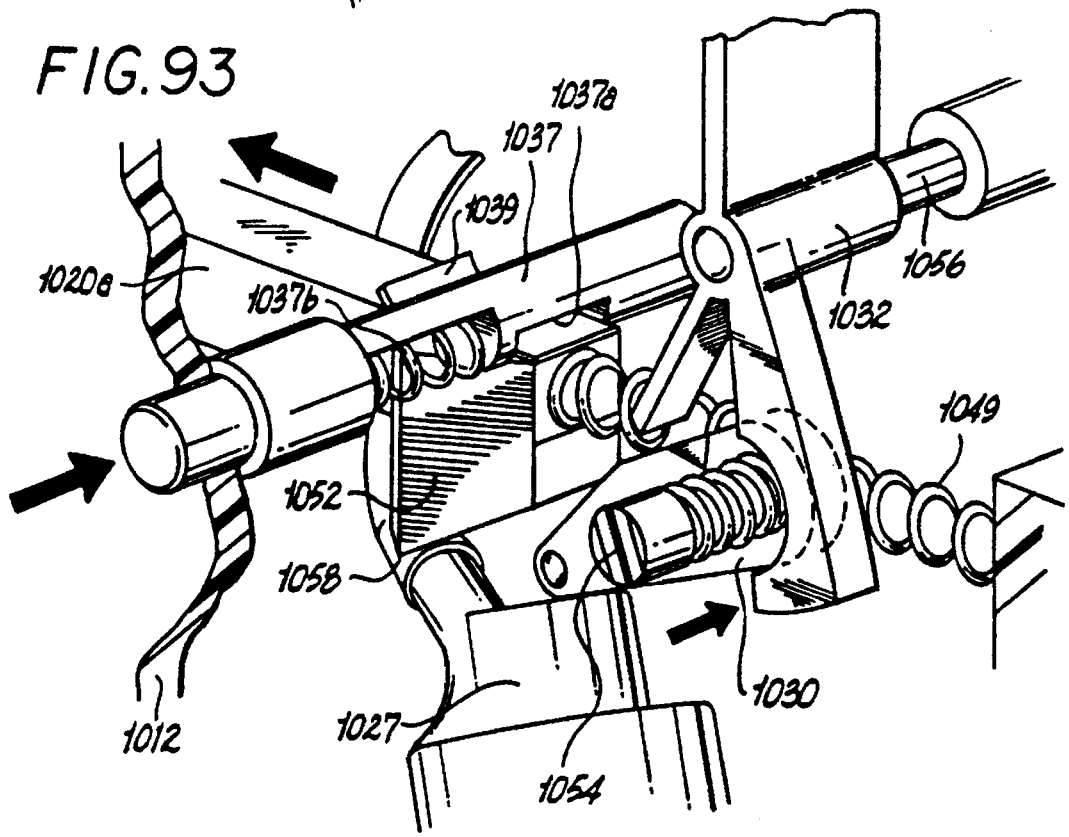
FIG. 93 is an enlarged perspective view of the safety mechanism illustrated in FIG. 92 disposed in an unlocked position to permit user access to the actuation trigger.

Referring to FIGS. 92 and 93, in conjunction with FIG. 94, after the fastener applying assembly 1035 has been closed, safety mechanism 1025 may be depressed to cause the trigger 1020 to be released from and to extend from the recessed area formed within the stationary handle 1016 of handle assembly 1012. Safety mechanism 1025 includes a spring biased transverse blocking shaft 1037 having an undercut 1037a formed therein, and a planar engaging plate 1039 having an upturned end portion 1039a. Engaging plate 1039 is mounted on the trigger shaft 1020a which is biased distally by a compression spring 1049. To release the trigger 1020, the blocking shaft 1037 is moved from a first position against the bias of an internal compression spring 1037b, shown in FIG. 92, in which the upturned portion 1039a of engaging plate 1039 abuts the blocking shaft 1037 to a second position, shown in FIG. 93, in which the blocking shaft 1037 is shifted to enable the upturned portion 1039a of engaging plate 1039 to move through the undercut 1037a of blocking shaft 1037, and permit the trigger 1020 to translate into a user accessible position under the influence of compression spring 1049.

With continued reference to FIGS. 92 and 93, the proximal end portion of trigger shaft 1020a defines a tapered firing block 1052 which is dimensioned and configured to interact with the rocker link 1030. As described previously hereinabove with respect to the firing control mechanism 915 of surgical apparatus 810, when this apparatus is fired, the rocker link 1030 operatively interacts with the latching link 1032 to effect the controlled movement of the valve 1027 towards the stationary gas supply canister 1026.

Referring to FIG. 94, depression of trigger 1020 will cause the firing block 1052 to urge the rocker link 1030 in a counter-clockwise direction about the transverse shaft 1054. As rocker link 1030 rotates, it interacts with latching link 1032, causing the rocker link 1030 to shift laterally and the latching link 1032 to rotate counter-clockwise about transverse shaft 1056 into a latching position. At such a time, the valve 1027 will be urged toward the gas canister 1026 and gas will be expelled therefrom. In one embodiment of the invention, valve 1027 is mounted in a chassis with a mounting means, e.g., a pin, introduced through the chassis to limit the travel of valve 1027 therewithin. The gas will then pass through a flexible conduit 1058, into the compression chamber 1022 where it will serve to drive the piston 1023 in a proximal direction against the bias of a return spring 1057. As the piston 1023 travels proximally, it draws therewith a drive shaft 1059 which extends into the body portion 1044 of surgical apparatus 1010 to interact with the fastener applying assembly 1035.

When the piston has completed its stroke, as shown for example in FIG. 95, a stem 1060, which extends proximally from the piston 1023, will interact with an outwardly depending portion 1063 of a release shaft 1062 and will urge the release shaft 1062 in a proximal direction. Release shaft 1062 includes a depending distal portion 1064 from which extends a transverse detent 1066. Detent 1066 is dimensioned and configured to interfere with the latching link 1032 and cause the disengagement of the latching link 1032 and the rocker link 1030 after the apparatus 1010 has been actuate. Once disengaged, each of the links will return to their respective prefired positions, spaced from one another within the stationary hand grip 1016. The release shaft 1064 also interacts with an indexing counter mechanism 1068 which is similar to that which is provided in surgical apparatus 810.

Referring again to FIG. 91 in conjunction with FIGS. 95 and 95a, the counter mechanism 1068 of surgical apparatus 1010 includes a rack member 1070 which is slidably disposed in the barrel portion 1014 of handle assembly 1012 adjacent the compression chamber 1022 and a cantilevered latch spring 1071 which interacts with the rack member to maintain the longitudinal position thereof. The rack member 1070 includes five notched engagement areas 1070a–1070e configured to receive a ratchet tooth 1072 which depends from the release shaft 1062. Each of the engagement areas 1070a–1070e have associated therewith corresponding numerical indicia which are visible through a windowed porthole 1074 formed in the barrel portion 1014 of handle assembly 1012. In particular, the engagement areas 1070a–1070d have associated therewith the numerals "41–1", respectively. These numerals correspond to the number of times the surgical apparatus 1010 may be operated to sequentially apply fasteners to body tissue during a surgical procedure. Engagement area 1070e has associated therewith the numeral "0", which, when viewed through the windowed porthole 1074, as illustrated in FIG. 95a, indicates to the user that surgical apparatus 1010 can no longer be operated.

The first four engagement areas of rack member 1070 are configured to permit the relative movement of the ratchet tooth 1072 and the rack member 1070, while the fifth engagement area 1070e is configured to inhibit the relative movement of the ratchet tooth 1072 and the rack member 1070. As a result, after the fourth operation of surgical apparatus 1010, longitudinal movement of the release shaft 1062 will be inhibited to the extent that the latching link 1032 will be released from rocker link 1030 but it will not be permitted to return to its prefired position as shown specifically in FIG. 95. Thus, further interaction between the latching link 1032 and the rocker link 1030 will not occur, and the surgical apparatus 1010 will be advantageously rendered inoperative.

Figure 96:
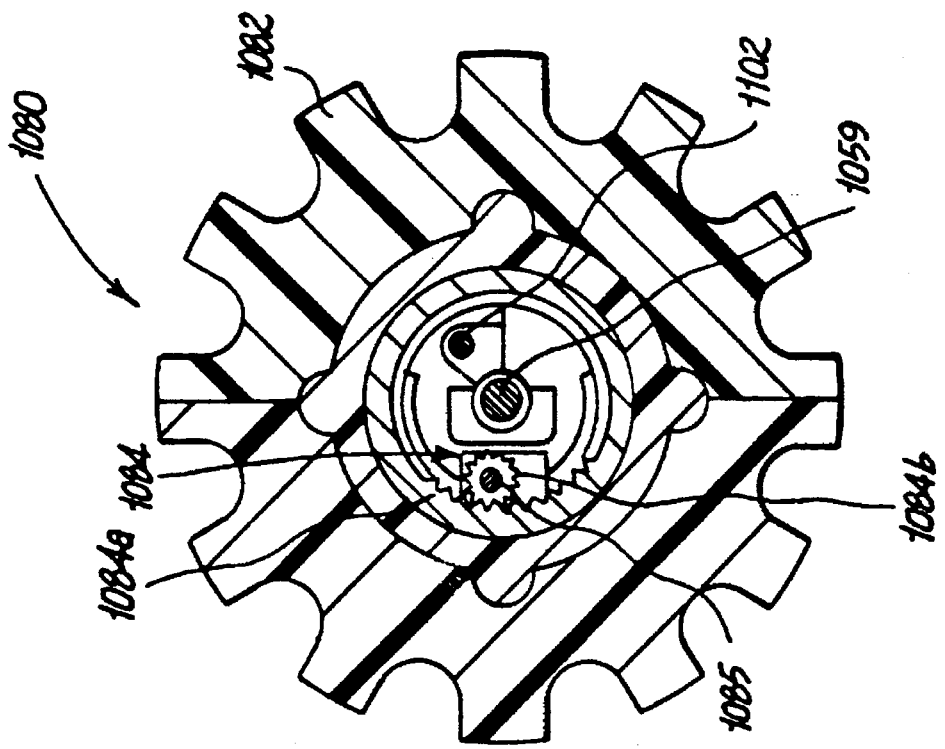
FIG. 96 is a cross-sectional view taken along line 96—96 of FIG. 91 illustrating the articulation control mechanism of the gas powered surgical apparatus of FIG. 90.

Referring to FIG. 96 in conjunction with FIGS. 90 and 90a, the articulation control mechanism 1080 of the subject invention is illustrated. The articulation control mechanism 1080 includes a rotation knob 1082 within which is housed a pinion gear assembly 1084 including an outer drive gear 1084a which is operatively connected to rotation knob 1082 and which rotates in response to user rotation thereof. The outer drive gear 1084a meshes with an internal pinion gear 1084b, which, in turn, is operatively connected to an articulation shaft 1085 which extends through the elongated body 1044 of surgical apparatus 1010 to the fastener applying assembly 1035. The articulation shaft 1085 operates in substantially the same manner as the articulation shaft 966 of the surgical apparatus 810 described hereinabove. The articulation shaft 966 translate in a longitudinal direction in response to the rotation of pinion gear 1084b to effect articulated movement of the fastener applying assembly 1035 about the "y-axis" illustrated in FIG. 90a.

Figure 97:
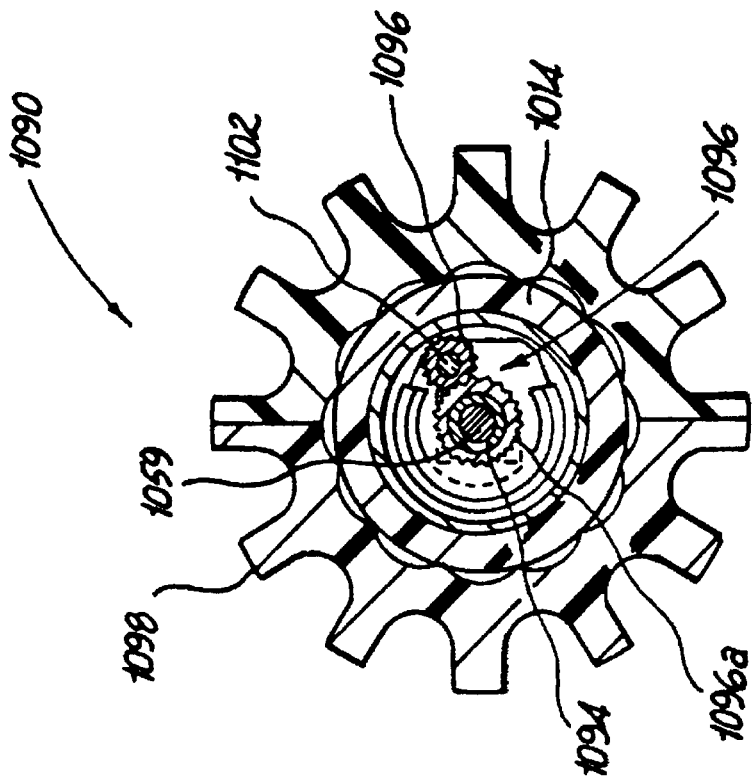
FIG. 97 is a cross-sectional view taken along line 97—97 of FIG. 91 illustrating the control mechanism for effecting the independent rotation of the fastener applying assembly of the gas powered surgical apparatus shown in FIG. 90.

Referring to FIG. 97 in conjunction with FIGS. 90 and 90a, the rotation control mechanism 1090 of surgical apparatus 1010 includes a rotation knob 1092 which is disposed substantially within the barrel portion 1014 of the handle assembly 1012. A rotation shaft 1094 extends from rotation knob 1092 to a pinion gear assembly 1096 which is housed within a rotation collar 1098. The pinion gear assembly 1096 includes a central drive gear 1096a which is connected to rotation shaft 1094, and an outer pinion gear 1096b which meshes with drive gear 1096a and which is operatively connected to an elongated transmission shaft 1102 which extends from the pinion gear assembly 1096, through the body portion 1044, to the fastener applying assembly 1035, to effect the independent rotation thereof about a longitudinal axis extending therethrough (i.e. the z-axis as shown in FIG. 90a). It is further contemplated according to the present invention that a braking structure may be provided adjacent rotation knob 1092. The braking structure would be axially displaced relative to the rotation knob 1092 in response to approximation of the anvil and cartridge, such that the braking structure would frictionally abut rotation knob 1092 in response to approximation of the anvil and cartridge. Thus, the fastener applying assembly would not be rotatable about the z-axis once the cartridge and anvil are approximated.

Rotation collar 1098 is operatively connected to the body portion 1044 of surgical apparatus 1010 and functions to effect the axial rotation of the elongated body portion 1044 about the longitudinal axis defined thereby (i.e. the x-axis).

It will be understood by those having ordinary skill in the art that various modifications or changes can be made to the various embodiments of the subject invention herein disclosed without departing from the spirit or scope thereof. For example, various sizes of the instrument are contemplated, as are various types of construction materials. Alternative internal components may also be utilized to distally transmit the rotation/articulation forces from the control mechanisms, e.g., rotation knobs 1082, 1092 and rotation collar 1098, to the distally positioned cooperating structures. For example, a series of nested tubular members may be provided that are operatively associated with respective rotation knobs/ collars, such tubular members including pin and slot interconnections which allow relative axial motions between respective tubular members while ensuring conjoint rotation, as described hereinabove. Therefore, the above description should not be construed as limiting the invention, but merely as exemplifications of preferred embodiments thereof.

To the extent not already indicated, it will also be understood by those having ordinary skill in the art that any one of the specific embodiments herein described and illustrated may be further modified to incorporate features shown in other of the embodiments.

What is claimed is:

1. A surgical apparatus for driving surgical fasteners comprising:
    a) a frame portion defining an elongated barrel section and a stationary hand grip section which depends angularly from said barrel section;
    b) an elongated body portion extending distally from said barrel section of said frame portion;
    c) a fastener applying assembly associated with a distal end portion of said body portion, said fastener applying assembly including:
        i) a cartridge assembly having a tissue engaging surface thereon and having a plurality of surgical fasteners contained therein; and
        ii) an anvil member mounted adjacent said cartridge assembly and having a fastener forming surface thereon, said anvil member and said cartridge assembly being relatively movable between an open position wherein said fastener forming surface is spaced from said tissue engaging surface and a closed position wherein said fastener forming surface is in close cooperative alignment with said tissue engaging surface;
    d) an approximation assembly operatively associated with said fastener applying assembly and actuable from said frame portion for effecting the relative movement of said anvil member and said cartridge assembly between said open and closed positions;
    e) a fastener ejection assembly movable through said cartridge assembly from a distal end portion thereof toward a proximal end portion thereof and actuable from said frame portion for sequentially ejecting said plurality of surgical fasteners from said cartridge assembly;
    f) a pneumatic actuation system operatively associated with said fastener ejection assembly and including a canister of compressed gas disposed within said stationary hand grip section of said frame portion, a valve member communicating with said canister of compressed gas, and a compression chamber defined within said barrel section of said frame portion for housing a piston which is movable through said compression chamber in response to a release of compressed gas from said canister to drive said fastener ejection assembly, wherein said canister has a fixed longitudinal orientation with respect to said frame portion and said valve member is configured to move relative to said canister of compressed gas for releasing compressed gas therefrom;
    g) an actuation trigger operatively associated with said stationary hand grip section of said frame portion for moving said valve member toward said canister of compressed gas; and
    h) a spring biased blocking member operatively associated with said frame portion for selectively inhibiting movement of said actuation trigger while maintaining said actuation trigger in a position wherein access thereto is precluded.

2. A surgical apparatus as recited in claim 1, wherein said piston is configured to translate through said compression chamber from a distal end portion thereof toward a proximal end portion thereof in response to said release of compressed gas from said canister.

3. A surgical apparatus as recited in claim 1, wherein said frame portion includes a pivoting handle configured for movement toward and away from said stationary hand grip section to actuate said approximation assembly.

4. A surgical apparatus as recited in claim 1, further including an actuation assembly including a pivotable link and a latch member, the pivotable link being movable to cause said valve member to move relative to said canister to cause gas to be expelled from said canister to actuate said fastener ejection assembly, said latch member being operatively associated with said pivotable link to retain said canister and said valve member in relative positions to allow gas to be expelled from said canister, and a release member supported on said piston and being operatively associated with said latch member to release said canister and said valve member from said relative positions.

5. A surgical apparatus for driving surgical fasteners comprising:
    a) a frame portion defining a longitudinal axis;
    b) an elongated body portion extending distally from said frame portion;
    c) a fastener applying assembly operatively associated with a distal end portion of said body portion and including;
        i) a cartridge member containing a plurality of surgical fasteners; and
        ii) an anvil member mounted adjacent said cartridge member, said cartridge member and said anvil member being relatively movable between an open position and a closed position;
    d) fastener ejection means actuable from said frame portion for sequentially ejecting said plurality of surgical fasteners from said cartridge member to be driven against said anvil member;

e) a pneumatic actuation system disposed within said frame portion and operatively associated with said fastener ejection means, said pneumatic actuation system including:
  i) a canister of compressed gas having a fixed longitudinal orientation with respect to said frame portion; and
  ii) a valve member configured to communicate with said canister of compressed gas; and f) an actuation assembly including a pivotable link, said link being movable to cause said valve member to move relative to said canister to effect communication therebetween and cause gas to be expelled from said canister to actuate said fastener ejection means.

6. A surgical apparatus as recited in claim 5, wherein said canister of compressed gas is oriented within said frame portion in such a manner so that the axial centerline thereof is angled with respect to the longitudinal axis of said frame portion.

7. A surgical apparatus as recited in claim 5, wherein said canister of compressed gas is oriented within said frame portion in such a manner so that the axial centerline thereof is parallel to the longitudinal axis of said frame portion.

8. A surgical apparatus as recited in claim 5, wherein said actuation assembly further includes a latch member, said latch member being operatively associated with said pivotable link to retain said canister and valve member in communication to cause gas to be expelled from the canister.

9. A surgical apparatus as recited in claim 8, wherein said pneumatic actuation system includes a piston.

10. A surgical apparatus as recited in claim 9, further including a release member, said release member being operatively associated with the latch member to release said canister and valve member from communication.

11. A surgical apparatus as recited in claim 10, wherein said release member is supported on said piston.

* * * * *